(12) United States Patent
Pieczykolan et al.

(10) Patent No.: US 9,175,059 B2
(45) Date of Patent: Nov. 3, 2015

(54) ANTICANCER FUSION PROTEIN COMPRISING TRAIL AND A GROWTH FACTOR RECEPTOR INHIBITOR

(75) Inventors: Jerzy Szczepan Pieczykolan, Radecznica (PL); Sebastian Dominik Pawlak, Warsaw (PL); Bartlomiej Maciej Żerek, Dabrowa (PL); Piotr Kamil Rózga, Skierniewice (PL)

(73) Assignee: Adamed Sp. z o.o., Czosnów k/Warszawy (PL)

( * ) Notice: Subject to any disclaimer, the term of this patent is extended or adjusted under 35 U.S.C. 154(b) by 106 days.

(21) Appl. No.: 13/978,090

(22) PCT Filed: Jan. 5, 2012

(86) PCT No.: PCT/EP2012/050145
§ 371 (c)(1),
(2), (4) Date: Jul. 2, 2013

(87) PCT Pub. No.: WO2012/093158
PCT Pub. Date: Jul. 12, 2012

(65) Prior Publication Data
US 2013/0288963 A1    Oct. 31, 2013

(30) Foreign Application Priority Data
Jan. 5, 2011 (PL) ......................................... 393578

(51) Int. Cl.
| | |
|---|---|
| *C07K 14/47* | (2006.01) |
| *C07K 14/52* | (2006.01) |
| *C07K 14/475* | (2006.01) |
| *C07K 14/485* | (2006.01) |
| *C07K 14/49* | (2006.01) |
| *C07K 7/06* | (2006.01) |
| *C07K 7/08* | (2006.01) |
| *C07K 19/00* | (2006.01) |
| *A61K 38/17* | (2006.01) |
| *A61K 38/18* | (2006.01) |
| *C07K 14/705* | (2006.01) |
| *C07K 14/515* | (2006.01) |

(52) U.S. Cl.
CPC ................. *C07K 14/52* (2013.01); *A61K 38/17* (2013.01); *A61K 38/18* (2013.01); *C07K 14/475* (2013.01); *C07K 14/485* (2013.01); *C07K 14/49* (2013.01); *C07K 14/515* (2013.01); *C07K 14/70575* (2013.01); *A61K 38/1808* (2013.01); *A61K 38/1858* (2013.01); *C07K 7/06* (2013.01); *C07K 7/08* (2013.01); *C07K 14/4747* (2013.01); *C07K 2319/00* (2013.01); *C07K 2319/33* (2013.01); *C07K 2319/50* (2013.01)

(58) Field of Classification Search
None
See application file for complete search history.

(56) References Cited

U.S. PATENT DOCUMENTS

2005/0244370 A1* 11/2005 Pfizenmaier et al. ........ 424/85.1

FOREIGN PATENT DOCUMENTS

| CN | 1 546 528 A | 11/2004 |
|---|---|---|
| CN | 1 609 124 A | 4/2005 |
| WO | WO 2004/035794 A1 | 4/2004 |
| WO | WO 2009/140469 A2 | 1/2009 |
| WO | WO 2010/005519 A1 | 1/2010 |
| WO | WO 2011/161260 A1 | 12/2011 |

OTHER PUBLICATIONS

Abdulghani et al. TRAIL receptor signaling and therapeutics. Expert Opin Ther Targets 14(10): 1091-1108, 2010.*
Ashkenazi et al. Ligand-based targeting of apoptosis in cancer: the potential of recombinant human apoptosis ligand 2/tumor necrosis factor-related apoptosis-inducing ligand (rhApo2L/TRAIL). J Clin Oncol 26(21): 3621-3630, 2008.*
Pieczykolan et al. Preclinical evaluation of anticancer potential of AD-051.4-novel fusion molecule with dual antiangiogenic and anti-cancer potential. Eur J Cancer Suppl2 49: S127, #606, Sep. 2013.*
Pieczykolan et al. Preclinical evaluation of the novel fusion molecule with high dual antiangiogenic and anticancer potential. Cancer Res 74: #2600, Oct. 2014.*
Rozga et al. Induction of apoptosis and inhibition by novel fusion protein-ADO54.9 as a new preclinical strategy in cancer treatment. Eur J Cancer Suppl6 50: 118, #367, Nov. 2014.*
Rozga et al. Inhibition of PDGF pathway by dual antiangiogenic and propapoptotic fusion molecule is a new preclinical strategy to treat cancer. Eur J Cancer Suppl2 49: S127, #605, Sep. 2013.*
Rozga et al. Induction of apoptosis and inhibition of angiogenesis by novel fusion protein-AD-O54.9 as a new preclinical strategy in cancer treatment. Cancer Res 74: #2276, Oct. 2014.*
Yang et al. AD-KDRscFv:sTRAIL displays a synergistic antitumor effect without obvious cytotoxicity to normal tissues. Int Immunopharmacol 13: 37-45, 2012.*
English language abstract of Chinese Patent No. CN 1 546 528 A (Univ Pla 2$^{nd}$ Military Medical [CN]), issued Nov. 17, 2004.
English language abstract of Chinese Patent No. CN 1 609 124 A (Shanghai Qiaer Biotechnology Co Ltd), issued Apr. 27, 2005.
Ren N. et al.: "Expression of Tumstatin 193-230-TRAIL fusion protein and identification of its biological functions", Academic Journal of Second Military Medical University 200805 on LNKD-DOI:10. 3724/SP.J.1008.2008.00474, vol. 29, No. 5, May 2008, pp. 474-478.
International Search Report issued by the International Searching Authority (ISA/O.E.P.M.) on Apr. 26, 2012 in connection with International Application No. PCT/EP2012/050145.
Written Opinion of the International Searching Authority issued on Apr. 26, 2012 in connection with International Application No. PCT/EP2012/050145.

* cited by examiner

*Primary Examiner* — Bridget E Bunner
(74) *Attorney, Agent, or Firm* — Gary J. Gershik; Cooper & Dunham LLP

(57) ABSTRACT

A fusion protein comprising domain (a) which is a functional fragment of hTRAIL protein sequence, which fragment begins with an amino acid at a position not lower than hTRAIL95, or a homolog of said functional fragment having at least 70% sequence identity; and domain (b) which is a sequence of an anti-angiogenic effector peptide, wherein the sequence of domain (b) is attached at the C-terminus or N-terminus of domain (a). The fusion protein can be used for the treatment of cancer diseases.

14 Claims, 22 Drawing Sheets

Ex. 7

Ex. 8

Ex. 9

Ex. 10

Ex. 11

Ex. 12

Ex. 13

Ex. 14

Ex. 15

Ex. 1

Ex. 4

Ex. 5

Ex. 9 rhTRAIL 114-281

Ex. 14

SEQUENCE LISTING

<160> NUMBER OF SEQ ID NOS: 59

<210> SEQ ID NO 1
<211> LENGTH: 173
<212> TYPE: PRT
<213> ORGANISM: Artificial Sequence
<220> FEATURE:
<223> OTHER INFORMATION: synthesized, a fusion protein comprising: a fragment of TRAIL protein, a heptapeptide derived from VEGF and flexible glycine steric linker.

<400> SEQUENCE: 1

Arg Lys Arg Lys Lys Ser Arg Gly Gly Gly Gly Gly Arg Val Ala Ala
1               5                   10                  15

His Ile Thr Gly Thr Arg Gly Arg Ser Asn Thr Leu Ser Ser Pro Asn
            20                  25                  30

Ser Lys Asn Glu Lys Ala Leu Gly Arg Lys Ile Asn Ser Trp Glu Ser
        35                  40                  45

Ser Arg Ser Gly His Ser Phe Leu Ser Asn Leu His Leu Arg Asn Gly
    50                  55                  60

Glu Leu Val Ile His Glu Lys Gly Phe Tyr Tyr Ile Tyr Ser Gln Thr
65                  70                  75                  80

```
Tyr Phe Arg Phe Gln Glu Glu Ile Lys Glu Asn Thr Lys Asn Asp Lys
                85                  90                  95

Gln Met Val Gln Tyr Ile Tyr Lys Tyr Thr Ser Tyr Pro Asp Pro Ile
            100                 105                 110

Leu Leu Met Lys Ser Ala Arg Asn Ser Cys Trp Ser Lys Asp Ala Glu
            115                 120                 125

Tyr Gly Leu Tyr Ser Ile Tyr Gln Gly Gly Ile Phe Glu Leu Lys Glu
            130                 135                 140

Asn Asp Arg Ile Phe Val Ser Val Thr Asn Glu His Leu Ile Asp Met
145                 150                 155                 160

Asp His Glu Ala Ser Phe Phe Gly Ala Phe Leu Val Gly
                165                 170

<210> SEQ ID NO 2
<211> LENGTH: 199
<212> TYPE: PRT
<213> ORGANISM: Artificial Sequence
<220> FEATURE:
<223> OTHER INFORMATION: synthesized, a fusion protein comprising: a
      fragment of TRAIL protein, a heptapeptide derived from VEGF and
      flexible glycine steric linker.

<400> SEQUENCE: 2

Arg Lys Arg Lys Lys Ser Arg Gly Gly Gly Gly Thr Ser Glu Glu
1               5                   10                  15

Thr Ile Ser Thr Val Gln Glu Lys Gln Gln Asn Ile Ser Pro Leu Val
            20                  25                  30

Arg Glu Arg Gly Pro Gln Arg Val Ala Ala His Ile Thr Gly Thr Arg
        35                  40                  45

Gly Arg Ser Asn Thr Leu Ser Ser Pro Asn Ser Lys Asn Glu Lys Ala
    50                  55                  60

Leu Gly Arg Lys Ile Asn Ser Trp Glu Ser Ser Arg Ser Gly His Ser
65                  70                  75                  80

Phe Leu Ser Asn Leu His Leu Arg Asn Gly Glu Leu Val Ile His Glu
                85                  90                  95

Lys Gly Phe Tyr Tyr Ile Tyr Ser Gln Thr Tyr Phe Arg Phe Gln Glu
            100                 105                 110

Glu Ile Lys Glu Asn Thr Lys Asn Asp Lys Gln Met Val Gln Tyr Ile
            115                 120                 125

Tyr Lys Tyr Thr Ser Tyr Pro Asp Pro Ile Leu Leu Met Lys Ser Ala
            130                 135                 140

Arg Asn Ser Cys Trp Ser Lys Asp Ala Glu Tyr Gly Leu Tyr Ser Ile
145                 150                 155                 160

Tyr Gln Gly Gly Ile Phe Glu Leu Lys Glu Asn Asp Arg Ile Phe Val
                165                 170                 175

Ser Val Thr Asn Glu His Leu Ile Asp Met Asp His Glu Ala Ser Phe
            180                 185                 190

Phe Gly Ala Phe Leu Val Gly
            195

<210> SEQ ID NO 3
<211> LENGTH: 230
<212> TYPE: PRT
<213> ORGANISM: Artificial Sequence
<220> FEATURE:
<223> OTHER INFORMATION: synthesized, a fusion protein comprising: a
      fragment of TRAIL protein, a heptapeptide derived from VEGF,
      fragments of tumstatin, a steric glycine linker and sequences of
      cleavage sites recognized by MMP and uPA.
```

```
<400> SEQUENCE: 3

Arg Lys Arg Lys Ser Arg Gly Gly Gly Gly Arg Val Ala Ala
1               5                   10                  15

His Ile Thr Gly Thr Arg Gly Arg Ser Asn Thr Leu Ser Ser Pro Asn
            20                  25                  30

Ser Lys Asn Glu Lys Ala Leu Gly Arg Lys Ile Asn Ser Trp Glu Ser
            35                  40                  45

Ser Arg Ser Gly His Ser Phe Leu Ser Asn Leu His Leu Arg Asn Gly
50                  55                  60

Glu Leu Val Ile His Glu Lys Gly Phe Tyr Tyr Ile Tyr Ser Gln Thr
65                  70                  75                  80

Tyr Phe Arg Phe Gln Glu Glu Ile Lys Glu Asn Thr Lys Asn Asp Lys
                85                  90                  95

Gln Met Val Gln Tyr Ile Tyr Lys Tyr Thr Ser Tyr Pro Asp Pro Ile
            100                 105                 110

Leu Leu Met Lys Ser Ala Arg Asn Ser Cys Trp Ser Lys Asp Ala Glu
            115                 120                 125

Tyr Gly Leu Tyr Ser Ile Tyr Gln Gly Gly Ile Phe Glu Leu Lys Glu
130                 135                 140

Asn Asp Arg Ile Phe Val Ser Val Thr Asn Glu His Leu Ile Asp Met
145                 150                 155                 160

Asp His Glu Ala Ser Phe Phe Gly Ala Phe Leu Val Gly Gly Gly
                165                 170                 175

Pro Leu Gly Leu Ala Gly Arg Val Val Arg Thr Met Pro Phe Leu Phe
            180                 185                 190

Cys Asn Val Asn Asp Val Cys Asn Phe Ala Ser Arg Asn Asp Tyr Ser
            195                 200                 205

Tyr Trp Leu Cys Asn Tyr Tyr Ser Asn Ser Tyr Ser Phe Trp Leu Ala
210                 215                 220

Ser Leu Asn Pro Glu Arg
225                 230

<210> SEQ ID NO 4
<211> LENGTH: 187
<212> TYPE: PRT
<213> ORGANISM: Artificial Sequence
<220> FEATURE:
<223> OTHER INFORMATION: synthesized, a fusion protein comprising: a
      fragment of TRAIL protein, two sequences of heptapeptide derived
      from VEGF, a steric glycine linker and a sequence of cleavage site
      recognized by MMP.

<400> SEQUENCE: 4

Arg Lys Arg Lys Ser Arg Pro Leu Gly Leu Ala Gly Glu Arg Lys
1               5                   10                  15

Arg Lys Lys Ser Arg Gly Gly Gly Gly Arg Val Ala Ala His Ile
            20                  25                  30

Thr Gly Thr Arg Gly Arg Ser Asn Thr Leu Ser Ser Pro Asn Ser Lys
            35                  40                  45

Asn Glu Lys Ala Leu Gly Arg Lys Ile Asn Ser Trp Glu Ser Ser Arg
50                  55                  60

Ser Gly His Ser Phe Leu Ser Asn Leu His Leu Arg Asn Gly Glu Leu
65                  70                  75                  80

Val Ile His Glu Lys Gly Phe Tyr Tyr Ile Tyr Ser Gln Thr Tyr Phe
                85                  90                  95
```

```
Arg Phe Gln Glu Glu Ile Lys Glu Asn Thr Lys Asn Asp Lys Gln Met
                100                 105                 110

Val Gln Tyr Ile Tyr Lys Tyr Thr Ser Tyr Pro Asp Pro Ile Leu Leu
            115                 120                 125

Met Lys Ser Ala Arg Asn Ser Cys Trp Ser Lys Asp Ala Glu Tyr Gly
        130                 135                 140

Leu Tyr Ser Ile Tyr Gln Gly Gly Ile Phe Glu Leu Lys Glu Asn Asp
145                 150                 155                 160

Arg Ile Phe Val Ser Val Thr Asn Glu His Leu Ile Asp Met Asp His
                165                 170                 175

Glu Ala Ser Phe Phe Gly Ala Phe Leu Val Gly
            180                 185

<210> SEQ ID NO 5
<211> LENGTH: 187
<212> TYPE: PRT
<213> ORGANISM: Artificial Sequence
<220> FEATURE:
<223> OTHER INFORMATION: synthesized, a fusion protein comprising: a
      fragment of TRAIL protein, two sequences of heptapeptide derived
      from VEGF, sequences of cleavage sites recognized by MMP and uPa
      and single glutamic acid and glycine residues.

<400> SEQUENCE: 5

Arg Lys Arg Lys Lys Ser Arg Val Val Arg Pro Leu Gly Leu Ala Gly
1               5                   10                  15

Glu Arg Lys Arg Lys Lys Ser Arg Gly Gly Arg Val Ala Ala His Ile
            20                  25                  30

Thr Gly Thr Arg Gly Arg Ser Asn Thr Leu Ser Ser Pro Asn Ser Lys
        35                  40                  45

Asn Glu Lys Ala Leu Gly Arg Lys Ile Asn Ser Trp Glu Ser Ser Arg
50                  55                  60

Ser Gly His Ser Phe Leu Ser Asn Leu His Leu Arg Asn Gly Glu Leu
65                  70                  75                  80

Val Ile His Glu Lys Gly Phe Tyr Tyr Ile Tyr Ser Gln Thr Tyr Phe
                85                  90                  95

Arg Phe Gln Glu Glu Ile Lys Glu Asn Thr Lys Asn Asp Lys Gln Met
                100                 105                 110

Val Gln Tyr Ile Tyr Lys Tyr Thr Ser Tyr Pro Asp Pro Ile Leu Leu
            115                 120                 125

Met Lys Ser Ala Arg Asn Ser Cys Trp Ser Lys Asp Ala Glu Tyr Gly
        130                 135                 140

Leu Tyr Ser Ile Tyr Gln Gly Gly Ile Phe Glu Leu Lys Glu Asn Asp
145                 150                 155                 160

Arg Ile Phe Val Ser Val Thr Asn Glu His Leu Ile Asp Met Asp His
                165                 170                 175

Glu Ala Ser Phe Phe Gly Ala Phe Leu Val Gly
            180                 185

<210> SEQ ID NO 6
<211> LENGTH: 222
<212> TYPE: PRT
<213> ORGANISM: Artificial Sequence
<220> FEATURE:
<223> OTHER INFORMATION: synthesized, a fusion protein comprising: a
      fragment of TRAIL protein, two sequences of heptapeptide derived
      from VEGF, sequences of cleavage sites recognized by MMP and uPa
      and cysteine flexible steric linker.

<400> SEQUENCE: 6
```

```
Arg Lys Arg Lys Lys Ser Arg Val Val Arg Pro Leu Gly Ile Ala Gly
 1               5                  10                  15

Glu Arg Lys Arg Lys Lys Ser Arg Gly Gly Cys Ala Ala Ala Cys
                20                  25                  30

Ala Ala Cys Thr Ser Glu Glu Thr Ile Ser Thr Val Gln Glu Lys Gln
            35                  40                  45

Gln Asn Ile Ser Pro Leu Val Arg Glu Arg Gly Pro Gln Arg Val Ala
        50                  55                  60

Ala His Ile Thr Gly Thr Arg Gly Arg Ser Asn Thr Leu Ser Ser Pro
 65                  70                  75                  80

Asn Ser Lys Asn Glu Lys Ala Leu Gly Arg Lys Ile Asn Ser Trp Glu
                85                  90                  95

Ser Ser Arg Ser Gly His Ser Phe Leu Ser Asn Leu His Leu Arg Asn
                100                 105                 110

Gly Glu Leu Val Ile His Glu Lys Gly Phe Tyr Tyr Ile Tyr Ser Gln
                115                 120                 125

Thr Tyr Phe Arg Phe Gln Glu Glu Ile Lys Glu Asn Thr Lys Asn Asp
        130                 135                 140

Lys Gln Met Val Gln Tyr Ile Tyr Lys Tyr Thr Ser Tyr Pro Asp Pro
145                 150                 155                 160

Ile Leu Leu Met Lys Ser Ala Arg Asn Ser Cys Trp Ser Lys Asp Ala
                165                 170                 175

Glu Tyr Gly Leu Tyr Ser Ile Tyr Gln Gly Gly Ile Phe Glu Leu Lys
                180                 185                 190

Glu Asn Asp Arg Ile Phe Val Ser Val Thr Asn Glu His Leu Ile Asp
            195                 200                 205

Met Asp His Glu Ala Ser Phe Phe Gly Ala Phe Leu Val Gly
        210                 215                 220

<210> SEQ ID NO 7
<211> LENGTH: 168
<212> TYPE: PRT
<213> ORGANISM: Artificial Sequence
<220> FEATURE:
<223> OTHER INFORMATION: synthesized, a fusion protein comprising: a
      fragment of TRAIL and a sequence being a ligand of CD13

<400> SEQUENCE: 7

Cys Asn Gly Arg Cys Pro Gln Arg Val Ala Ala His Ile Thr Gly Thr
 1               5                  10                  15

Arg Gly Arg Ser Asn Thr Leu Ser Ser Pro Asn Ser Lys Asn Glu Lys
                20                  25                  30

Ala Leu Gly Arg Lys Ile Asn Ser Trp Glu Ser Ser Arg Ser Gly His
            35                  40                  45

Ser Phe Leu Ser Asn Leu His Leu Arg Asn Gly Glu Leu Val Ile His
 50                  55                  60

Glu Lys Gly Phe Tyr Tyr Ile Tyr Ser Gln Thr Tyr Phe Arg Phe Gln
 65                  70                  75                  80

Glu Glu Ile Lys Glu Asn Thr Lys Asn Asp Lys Gln Met Val Gln Tyr
                85                  90                  95

Ile Tyr Lys Tyr Thr Ser Tyr Pro Asp Pro Ile Leu Leu Met Lys Ser
                100                 105                 110

Ala Arg Asn Ser Cys Trp Ser Lys Asp Ala Glu Tyr Gly Leu Tyr Ser
                115                 120                 125

Ile Tyr Gln Gly Gly Ile Phe Glu Leu Lys Glu Asn Asp Arg Ile Phe
```

```
                130                 135                 140
Val Ser Val Thr Asn Glu His Leu Ile Asp Met Asp His Glu Ala Ser
145                 150                 155                 160

Phe Phe Gly Ala Phe Leu Val Gly
                165
```

<210> SEQ ID NO 8
<211> LENGTH: 201
<212> TYPE: PRT
<213> ORGANISM: Artificial Sequence
<220> FEATURE:
<223> OTHER INFORMATION: synthesized, a fusion protein comprising: a
      fragment of TRAIL, a sequence being a ligand of CD13 and a
      sequence of flexible glycine-serine linker.

<400> SEQUENCE: 8

```
Cys Asp Cys Arg Gly Asp Cys Phe Cys Gly Gly Gly Gly Ser Thr Ser
1               5                   10                  15

Glu Glu Thr Ile Ser Thr Val Gln Glu Lys Gln Gln Asn Ile Ser Pro
                20                  25                  30

Leu Val Arg Glu Arg Gly Pro Gln Arg Val Ala Ala His Ile Thr Gly
            35                  40                  45

Thr Arg Gly Arg Ser Asn Thr Leu Ser Ser Pro Asn Ser Lys Asn Glu
        50                  55                  60

Lys Ala Leu Gly Arg Lys Ile Asn Ser Trp Glu Ser Ser Arg Ser Gly
65                  70                  75                  80

His Ser Phe Leu Ser Asn Leu His Leu Arg Asn Gly Glu Leu Val Ile
                85                  90                  95

His Glu Lys Gly Phe Tyr Tyr Ile Tyr Ser Gln Thr Tyr Phe Arg Phe
            100                 105                 110

Gln Glu Glu Ile Lys Glu Asn Thr Lys Asn Asp Lys Gln Met Val Gln
        115                 120                 125

Tyr Ile Tyr Lys Tyr Thr Ser Tyr Pro Asp Pro Ile Leu Leu Met Lys
130                 135                 140

Ser Ala Arg Asn Ser Cys Trp Ser Lys Asp Ala Glu Tyr Gly Leu Tyr
145                 150                 155                 160

Ser Ile Tyr Gln Gly Gly Ile Phe Glu Leu Lys Glu Asn Asp Arg Ile
                165                 170                 175

Phe Val Ser Val Thr Asn Glu His Leu Ile Asp Met Asp His Glu Ala
            180                 185                 190

Ser Phe Phe Gly Ala Phe Leu Val Gly
        195                 200
```

<210> SEQ ID NO 9
<211> LENGTH: 192
<212> TYPE: PRT
<213> ORGANISM: Artificial Sequence
<220> FEATURE:
<223> OTHER INFORMATION: synthesized, a fusion protein comprising: a
      fragment of TRAIL, a sequence of PDGF fragment and sequences of
      cleavage sites recognized by urokinase uPA and metalloprotease
      MMP.

<400> SEQUENCE: 9

```
Tyr Gly Arg Pro Arg Gln Ser Gly Lys Lys Arg Lys Arg Lys Arg Leu
1               5                   10                  15

Lys Pro Thr Arg Val Val Arg Pro Leu Gly Leu Ala Gly Pro Gln Arg
                20                  25                  30

Val Ala Ala His Ile Thr Gly Thr Arg Gly Arg Ser Asn Thr Leu Ser
```

```
                35                  40                  45
Ser Pro Asn Ser Lys Asn Glu Lys Ala Leu Gly Arg Lys Ile Asn Ser
     50                  55                  60

Trp Glu Ser Ser Arg Ser Gly His Ser Phe Leu Ser Asn Leu His Leu
 65                  70                  75                  80

Arg Asn Gly Glu Leu Val Ile His Glu Lys Gly Phe Tyr Tyr Ile Tyr
                 85                  90                  95

Ser Gln Thr Tyr Phe Arg Phe Gln Glu Glu Ile Lys Glu Asn Thr Lys
            100                 105                 110

Asn Asp Lys Gln Met Val Gln Tyr Ile Tyr Lys Tyr Thr Ser Tyr Pro
        115                 120                 125

Asp Pro Ile Leu Leu Met Lys Ser Ala Arg Asn Ser Cys Trp Ser Lys
    130                 135                 140

Asp Ala Glu Tyr Gly Leu Tyr Ser Ile Tyr Gln Gly Gly Ile Phe Glu
145                 150                 155                 160

Leu Lys Glu Asn Asp Arg Ile Phe Val Ser Val Thr Asn Glu His Leu
                165                 170                 175

Ile Asp Met Asp His Glu Ala Ser Phe Phe Gly Ala Phe Leu Val Gly
            180                 185                 190

<210> SEQ ID NO 10
<211> LENGTH: 216
<212> TYPE: PRT
<213> ORGANISM: Artificial Sequence
<220> FEATURE:
<223> OTHER INFORMATION: synthesized, a fusion protein comprising: a
      fragment of TRAIL, a fragment of PDGF and sequences of cleavage
      sites recognized by urokinase uPA and metalloprotease MMP.

<400> SEQUENCE: 10

Tyr Gly Arg Pro Arg Gln Ser Gly Lys Lys Arg Lys Arg Lys Arg Leu
 1               5                  10                  15

Lys Pro Thr Arg Val Val Arg Pro Leu Gly Leu Ala Gly Thr Ser Glu
             20                  25                  30

Glu Thr Ile Ser Thr Val Gln Glu Lys Gln Gln Asn Ile Ser Pro Leu
         35                  40                  45

Val Arg Glu Arg Gly Pro Gln Arg Val Ala Ala His Ile Thr Gly Thr
     50                  55                  60

Arg Gly Arg Ser Asn Thr Leu Ser Ser Pro Asn Ser Lys Asn Glu Lys
 65                  70                  75                  80

Ala Leu Gly Arg Lys Ile Asn Ser Trp Glu Ser Ser Arg Ser Gly His
                 85                  90                  95

Ser Phe Leu Ser Asn Leu His Leu Arg Asn Gly Glu Leu Val Ile His
            100                 105                 110

Glu Lys Gly Phe Tyr Tyr Ile Tyr Ser Gln Thr Tyr Phe Arg Phe Gln
        115                 120                 125

Glu Glu Ile Lys Glu Asn Thr Lys Asn Asp Lys Gln Met Val Gln Tyr
    130                 135                 140

Ile Tyr Lys Tyr Thr Ser Tyr Pro Asp Pro Ile Leu Leu Met Lys Ser
145                 150                 155                 160

Ala Arg Asn Ser Cys Trp Ser Lys Asp Ala Glu Tyr Gly Leu Tyr Ser
                165                 170                 175

Ile Tyr Gln Gly Gly Ile Phe Glu Leu Lys Glu Asn Asp Arg Ile Phe
            180                 185                 190

Val Ser Val Thr Asn Glu His Leu Ile Asp Met Asp His Glu Ala Ser
        195                 200                 205
```

```
Phe Phe Gly Ala Phe Leu Val Gly
    210             215
```

<210> SEQ ID NO 11
<211> LENGTH: 226
<212> TYPE: PRT
<213> ORGANISM: Artificial Sequence
<220> FEATURE:
<223> OTHER INFORMATION: synthesized, a fusion protein comprising: a
      fragment of TRAIL, a PDGF fragment, sequences of cleavage sites
      recognized by urokinase uPA and metalloprotease MMP and a flexible
      glycine-cysteine-alanine linker.

<400> SEQUENCE: 11

```
Tyr Gly Arg Pro Arg Gln Ser Gly Lys Lys Arg Lys Arg Lys Arg Leu
1               5                   10                  15

Lys Pro Thr Arg Val Val Arg Pro Leu Gly Leu Ala Gly Gly Gly Cys
            20                  25                  30

Ala Ala Ala Cys Ala Ala Cys Thr Ser Glu Glu Thr Ile Ser Thr Val
        35                  40                  45

Gln Glu Lys Gln Gln Asn Ile Ser Pro Leu Val Arg Glu Arg Gly Pro
    50                  55                  60

Gln Arg Val Ala Ala His Ile Thr Gly Thr Arg Gly Arg Ser Asn Thr
65                  70                  75                  80

Leu Ser Ser Pro Asn Ser Lys Asn Glu Lys Ala Leu Gly Arg Lys Ile
                85                  90                  95

Asn Ser Trp Glu Ser Ser Arg Ser Gly His Ser Phe Leu Ser Asn Leu
            100                 105                 110

His Leu Arg Asn Gly Glu Leu Val Ile His Glu Lys Gly Phe Tyr Tyr
        115                 120                 125

Ile Tyr Ser Gln Thr Tyr Phe Arg Phe Gln Glu Glu Ile Lys Glu Asn
    130                 135                 140

Thr Lys Asn Asp Lys Gln Met Val Gln Tyr Ile Tyr Lys Tyr Thr Ser
145                 150                 155                 160

Tyr Pro Asp Pro Ile Leu Leu Met Lys Ser Ala Arg Asn Ser Cys Trp
                165                 170                 175

Ser Lys Asp Ala Glu Tyr Gly Leu Tyr Ser Ile Tyr Gln Gly Gly Ile
            180                 185                 190

Phe Glu Leu Lys Glu Asn Asp Arg Ile Phe Val Ser Val Thr Asn Glu
        195                 200                 205

His Leu Ile Asp Met Asp His Glu Ala Ser Phe Phe Gly Ala Phe Leu
    210                 215                 220

Val Gly
225
```

<210> SEQ ID NO 12
<211> LENGTH: 217
<212> TYPE: PRT
<213> ORGANISM: Artificial Sequence
<220> FEATURE:
<223> OTHER INFORMATION: synthesized, a fusion protein comprising: a
      fragment of TRAIL, fragments of tumstatine, sequences of cleavage
      sites recognized by urokinase uPA and metalloprotease MMP and a
      flexible linker consisting of 3 glycine residues.

<400> SEQUENCE: 12

```
Thr Met Pro Phe Leu Phe Cys Asn Val Asn Asp Val Cys Asn Phe Ala
1               5                   10                  15

Ser Arg Asn Asp Tyr Ser Tyr Trp Leu Cys Asn Tyr Tyr Ser Asn Ser
```

```
                    20                  25                  30
Tyr Ser Phe Trp Leu Ala Ser Leu Asn Pro Glu Arg Val Val Arg Pro
                35                  40                  45

Leu Gly Leu Ala Gly Gly Gly Arg Val Ala Ala His Ile Thr Gly
     50                  55                  60

Thr Arg Gly Arg Ser Asn Thr Leu Ser Ser Pro Asn Ser Lys Asn Glu
65                  70                  75                  80

Lys Ala Leu Gly Arg Lys Ile Asn Ser Trp Glu Ser Ser Arg Ser Gly
                 85                  90                  95

His Ser Phe Leu Ser Asn Leu His Leu Arg Asn Gly Glu Leu Val Ile
            100                 105                 110

His Glu Lys Gly Phe Tyr Tyr Ile Tyr Ser Gln Thr Tyr Phe Arg Phe
        115                 120                 125

Gln Glu Glu Ile Lys Glu Asn Thr Lys Asn Asp Lys Gln Met Val Gln
    130                 135                 140

Tyr Ile Tyr Lys Tyr Thr Ser Tyr Pro Asp Pro Ile Leu Leu Met Lys
145                 150                 155                 160

Ser Ala Arg Asn Ser Cys Trp Ser Lys Asp Ala Glu Tyr Gly Leu Tyr
                165                 170                 175

Ser Ile Tyr Gln Gly Gly Ile Phe Glu Leu Lys Glu Asn Asp Arg Ile
            180                 185                 190

Phe Val Ser Val Thr Asn Glu His Leu Ile Asp Met Asp His Glu Ala
        195                 200                 205

Ser Phe Phe Gly Ala Phe Leu Val Gly
    210                 215

<210> SEQ ID NO 13
<211> LENGTH: 220
<212> TYPE: PRT
<213> ORGANISM: Artificial Sequence
<220> FEATURE:
<223> OTHER INFORMATION: synthesized, a fusion protein comprising: a
      fragment of TRAIL, fragments of tumstatin, cleavage sites
      recognized by urokinase uPA and metalloprotease MMP and flexible
      glycine linkers.

<400> SEQUENCE: 13

Cys Asn Tyr Tyr Ser Asn Ser Tyr Ser Phe Trp Leu Ala Ser Leu Asn
1               5                  10                  15

Pro Glu Arg Val Val Arg Pro Leu Gly Leu Ala Gly Gly Gly Gly Arg
                20                  25                  30

Val Ala Ala His Ile Thr Gly Thr Arg Gly Arg Ser Asn Thr Leu Ser
            35                  40                  45

Ser Pro Asn Ser Lys Asn Glu Lys Ala Leu Gly Arg Lys Ile Asn Ser
        50                  55                  60

Trp Glu Ser Ser Arg Ser Gly His Ser Phe Leu Ser Asn Leu His Leu
65                  70                  75                  80

Arg Asn Gly Glu Leu Val Ile His Glu Lys Gly Phe Tyr Tyr Ile Tyr
                85                  90                  95

Ser Gln Thr Tyr Phe Arg Phe Gln Glu Glu Ile Lys Glu Asn Thr Lys
            100                 105                 110

Asn Asp Lys Gln Met Val Gln Tyr Ile Tyr Lys Tyr Thr Ser Tyr Pro
        115                 120                 125

Asp Pro Ile Leu Leu Met Lys Ser Ala Arg Asn Ser Cys Trp Ser Lys
    130                 135                 140

Asp Ala Glu Tyr Gly Leu Tyr Ser Ile Tyr Gln Gly Gly Ile Phe Glu
```

```
145                 150                 155                 160
Leu Lys Glu Asn Asp Arg Ile Phe Val Ser Val Thr Asn Glu His Leu
                165                 170                 175

Ile Asp Met Asp His Glu Ala Ser Phe Phe Gly Ala Phe Leu Val Gly
            180                 185                 190

Gly Gly Gly Thr Met Pro Phe Leu Phe Cys Asn Val Asn Asp Val Cys
        195                 200                 205

Asn Phe Ala Ser Arg Asn Asp Tyr Ser Tyr Trp Leu
    210                 215                 220

<210> SEQ ID NO 14
<211> LENGTH: 181
<212> TYPE: PRT
<213> ORGANISM: Artificial Sequence
<220> FEATURE:
<223> OTHER INFORMATION: synthesized, a fusion protein comprising: a
      fragment of TRAIL, a fragment of EGF and sequences of cleavage
      sites recognized by urokinase uPA and metalloprotease MMP.

<400> SEQUENCE: 14

Leu Gly Leu Arg Ser Leu Arg Glu Arg Val Val Arg Pro Leu Gly Leu
1               5                   10                  15

Ala Gly Pro Gln Arg Val Ala Ala His Ile Thr Gly Thr Arg Gly Arg
            20                  25                  30

Ser Asn Thr Leu Ser Ser Pro Asn Ser Lys Asn Glu Lys Ala Leu Gly
        35                  40                  45

Arg Lys Ile Asn Ser Trp Glu Ser Ser Arg Ser Gly His Ser Phe Leu
    50                  55                  60

Ser Asn Leu His Leu Arg Asn Gly Glu Leu Val Ile His Glu Lys Gly
65                  70                  75                  80

Phe Tyr Tyr Ile Tyr Ser Gln Thr Tyr Phe Arg Phe Gln Glu Glu Ile
                85                  90                  95

Lys Glu Asn Thr Lys Asn Asp Lys Gln Met Val Gln Tyr Ile Tyr Lys
            100                 105                 110

Tyr Thr Ser Tyr Pro Asp Pro Ile Leu Leu Met Lys Ser Ala Arg Asn
        115                 120                 125

Ser Cys Trp Ser Lys Asp Ala Glu Tyr Gly Leu Tyr Ser Ile Tyr Gln
    130                 135                 140

Gly Gly Ile Phe Glu Leu Lys Glu Asn Asp Arg Ile Phe Val Ser Val
145                 150                 155                 160

Thr Asn Glu His Leu Ile Asp Met Asp His Glu Ala Ser Phe Phe Gly
                165                 170                 175

Ala Phe Leu Val Gly
            180

<210> SEQ ID NO 15
<211> LENGTH: 217
<212> TYPE: PRT
<213> ORGANISM: Artificial Sequence
<220> FEATURE:
<223> OTHER INFORMATION: synthesized, a fusion protein comprising: a
      fragment of TRAIL, a fragment of EGF, cleavage sites recognized by
      urokinase uPA and metalloprotease MMP and flexible glycine-
      cysteine-alanine linker.

<400> SEQUENCE: 15

Leu Gly Leu Arg Ser Leu Arg Glu Arg Val Val Arg Pro Leu Gly Leu
1               5                   10                  15

Ala Gly Pro Gly Gly Gly Cys Ala Ala Ala Cys Ala Ala Cys Thr Ser
```

```
                    20                  25                  30
Glu Glu Thr Ile Ser Thr Val Gln Glu Lys Gln Gln Asn Ile Ser Pro
                35                  40                  45

Leu Val Arg Glu Arg Gly Pro Gln Arg Val Ala Ala His Ile Thr Gly
            50                  55                  60

Thr Arg Gly Arg Ser Asn Thr Leu Ser Ser Pro Asn Ser Lys Asn Glu
 65                  70                  75                  80

Lys Ala Leu Gly Arg Lys Ile Asn Ser Trp Glu Ser Ser Arg Ser Gly
                    85                  90                  95

His Ser Phe Leu Ser Asn Leu His Leu Arg Asn Gly Glu Leu Val Ile
            100                 105                 110

His Glu Lys Gly Phe Tyr Tyr Ile Tyr Ser Gln Thr Tyr Phe Arg Phe
        115                 120                 125

Gln Glu Glu Ile Lys Glu Asn Thr Lys Asn Asp Lys Gln Met Val Gln
        130                 135                 140

Tyr Ile Tyr Lys Tyr Thr Ser Tyr Pro Asp Pro Ile Leu Leu Met Lys
145                 150                 155                 160

Ser Ala Arg Asn Ser Cys Trp Ser Lys Asp Ala Glu Tyr Gly Leu Tyr
                165                 170                 175

Ser Ile Tyr Gln Gly Gly Ile Phe Glu Leu Lys Glu Asn Asp Arg Ile
            180                 185                 190

Phe Val Ser Val Thr Asn Glu His Leu Ile Asp Met Asp His Glu Ala
        195                 200                 205

Ser Phe Phe Gly Ala Phe Leu Val Gly
        210                 215

<210> SEQ ID NO 16
<211> LENGTH: 281
<212> TYPE: PRT
<213> ORGANISM: Homo sapiens
<300> PUBLICATION INFORMATION:
<308> DATABASE ACCESSION NUMBER: GenBank/P50591
<309> DATABASE ENTRY DATE: 1996-10-01
<313> RELEVANT RESIDUES IN SEQ ID NO: (1)..(281)

<400> SEQUENCE: 16

Met Ala Met Met Glu Val Gln Gly Gly Pro Ser Leu Gly Gln Thr Cys
 1               5                  10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
        50                  55                  60

Trp Asp Pro Asn Asp Glu Ser Met Asn Ser Pro Cys Trp Gln Val
 65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160
```

```
His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
            245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 17
<211> LENGTH: 7
<212> TYPE: PRT
<213> ORGANISM: Homo sapiens
<300> PUBLICATION INFORMATION:
<308> DATABASE ACCESSION NUMBER: GenBank/AAI72307.1
<309> DATABASE ENTRY DATE: 2009-03-16
<313> RELEVANT RESIDUES IN SEQ ID NO: (333)..(339)

<400> SEQUENCE: 17

Arg Lys Arg Lys Lys Ser Arg
1               5

<210> SEQ ID NO 18
<211> LENGTH: 25
<212> TYPE: PRT
<213> ORGANISM: Homo sapiens
<300> PUBLICATION INFORMATION:
<308> DATABASE ACCESSION NUMBER: GenBank/AAF72632.1
<309> DATABASE ENTRY DATE: 2000-05-30
<313> RELEVANT RESIDUES IN SEQ ID NO: (74)..(98)

<400> SEQUENCE: 18

Thr Met Pro Phe Leu Phe Cys Asn Val Asn Asp Val Cys Asn Phe Ala
1               5                   10                  15

Ser Arg Asn Asp Tyr Ser Tyr Trp Leu
            20                  25

<210> SEQ ID NO 19
<211> LENGTH: 18
<212> TYPE: PRT
<213> ORGANISM: Homo sapiens
<300> PUBLICATION INFORMATION:
<308> DATABASE ACCESSION NUMBER: GenBank/AAF72632.1
<309> DATABASE ENTRY DATE: 2000-05-30
<313> RELEVANT RESIDUES IN SEQ ID NO: (197)..(214)

<400> SEQUENCE: 19

Cys Asn Tyr Tyr Ser Asn Ser Tyr Ser Phe Trp Leu Ala Ser Leu Asn
1               5                   10                  15

Pro Glu

<210> SEQ ID NO 20
<211> LENGTH: 5
<212> TYPE: PRT
```

-continued

```
<213> ORGANISM: Artificial Sequence
<220> FEATURE:
<223> OTHER INFORMATION: synthetic peptide
<300> PUBLICATION INFORMATION:
<301> AUTHORS: Arap W., Pasqualini R., Ruoslahti E.
<302> TITLE: Cancer treatment by targeted drug delivery to tumor
       vasculature
<303> JOURNAL: Science (Washington DC)
<304> VOLUME: 279
<305> ISSUE: 5349
<306> PAGES: 377-380
<307> DATE: 1998-01-16
<313> RELEVANT RESIDUES IN SEQ ID NO: (1)..(5)

<400> SEQUENCE: 20

Cys Asn Gly Arg Cys
1               5

<210> SEQ ID NO 21
<211> LENGTH: 9
<212> TYPE: PRT
<213> ORGANISM: Artificial Sequence
<220> FEATURE:
<223> OTHER INFORMATION: synthetic construct
<300> PUBLICATION INFORMATION:
<308> DATABASE ACCESSION NUMBER: PDB/1FUL_A
<309> DATABASE ENTRY DATE: 2009-07-10
<313> RELEVANT RESIDUES IN SEQ ID NO: (2)..(10)

<400> SEQUENCE: 21

Cys Asp Cys Arg Gly Asp Cys Phe Cys
1               5

<210> SEQ ID NO 22
<211> LENGTH: 19
<212> TYPE: PRT
<213> ORGANISM: Homo sapiens
<300> PUBLICATION INFORMATION:
<301> AUTHORS: Khachigian LM, Owensby DA, Chesterman CN.
<302> TITLE: A tyrosinated peptide representing the alternatively
       spliced exon of the platelet-derived growth factor A-chain binds
       specifically to cultured cells and interferes with binding of
       several growth factors.
<303> JOURNAL: Journal of Biological Chemistry
<304> VOLUME: 25
<305> ISSUE: 267
<306> PAGES: 1660-1666
<307> DATE: 1992-01-25
<300> PUBLICATION INFORMATION:
<301> AUTHORS: Khachigian LM, Field SL, Crouch R, Chesterman CN
<302> TITLE: Platelet-derived growth factor A-chain synthetic peptide
       inhibits human glioma xenograft proliferation in nude mice.
<303> JOURNAL: Anticancer Res
<304> VOLUME: 15
<305> ISSUE: 2
<306> PAGES: 337-41
<307> DATE: 1995-04-05

<400> SEQUENCE: 22

Tyr Gly Arg Pro Arg Gln Ser Gly Lys Lys Arg Lys Arg Lys Arg Leu
1               5                   10                  15

Lys Pro Thr

<210> SEQ ID NO 23
<211> LENGTH: 8
<212> TYPE: PRT
<213> ORGANISM: Homo sapiens
<300> PUBLICATION INFORMATION:
<308> DATABASE ACCESSION NUMBER: GenBank/AAI67147.1
<309> DATABASE ENTRY DATE: 2008-05-05
<313> RELEVANT RESIDUES IN SEQ ID NO: (453)..(460)
```

```
<400> SEQUENCE: 23

Leu Gly Leu Arg Ser Leu Arg Glu
1               5

<210> SEQ ID NO 24
<211> LENGTH: 6
<212> TYPE: PRT
<213> ORGANISM: Artificial Sequence
<220> FEATURE:
<223> OTHER INFORMATION: synthesized, a protease cutting sequence

<400> SEQUENCE: 24

Pro Leu Gly Leu Ala Gly
1               5

<210> SEQ ID NO 25
<211> LENGTH: 4
<212> TYPE: PRT
<213> ORGANISM: Artificial Sequence
<220> FEATURE:
<223> OTHER INFORMATION: synthesized, protease cutting sequence

<400> SEQUENCE: 25

Arg Val Val Arg
1

<210> SEQ ID NO 26
<211> LENGTH: 11
<212> TYPE: PRT
<213> ORGANISM: Artificial Sequence
<220> FEATURE:
<223> OTHER INFORMATION: synthesized, an artificial sequence of a steric
      linker

<400> SEQUENCE: 26

Gly Gly Gly Cys Ala Ala Ala Cys Ala Ala Cys
1               5                   10

<210> SEQ ID NO 27
<211> LENGTH: 10
<212> TYPE: PRT
<213> ORGANISM: Artificial Sequence
<220> FEATURE:
<223> OTHER INFORMATION: synthesized, an artificial sequence of a steric
      linker

<400> SEQUENCE: 27

Gly Gly Cys Ala Ala Ala Cys Ala Ala Cys
1               5                   10

<210> SEQ ID NO 28
<211> LENGTH: 5
<212> TYPE: PRT
<213> ORGANISM: Artificial Sequence
<220> FEATURE:
<223> OTHER INFORMATION: synthesized, an artificial sequence of a steric
      linker

<400> SEQUENCE: 28

Gly Gly Gly Gly Gly
1               5

<210> SEQ ID NO 29
<211> LENGTH: 4
<212> TYPE: PRT
<213> ORGANISM: Mus musculus
<300> PUBLICATION INFORMATION:
```

```
<308> DATABASE ACCESSION NUMBER: GenBank/CAA94521.1
<309> DATABASE ENTRY DATE: 1996-06-13
<313> RELEVANT RESIDUES IN SEQ ID NO: (122)..(124)

<400> SEQUENCE: 29

Gly Gly Gly Gly
1

<210> SEQ ID NO 30
<211> LENGTH: 5
<212> TYPE: PRT
<213> ORGANISM: Mus musculus
<300> PUBLICATION INFORMATION:
<308> DATABASE ACCESSION NUMBER: GenBank/CAA94521.1
<309> DATABASE ENTRY DATE: 1996-06-13
<313> RELEVANT RESIDUES IN SEQ ID NO: (122)..(126)

<400> SEQUENCE: 30

Gly Gly Gly Gly Ser
1               5

<210> SEQ ID NO 31
<211> LENGTH: 519
<212> TYPE: DNA
<213> ORGANISM: Artificial Sequence
<220> FEATURE:
<223> OTHER INFORMATION: synthesized, encoding a fusion protein
      comprising: a fragment of TRAIL protein, a heptapeptide derived
      from VEGF and flexible glycine steric linker.

<400> SEQUENCE: 31
cgtaaacgca aaaaaagtcg tggtggtggt ggtggccgcg ttgcggcaca tattacgggt      60
acccgtggcc gcagcaacac gctgagctct ccgaattcga aaaatgaaaa agcactgggc     120
cgcaaaatta actcgtggga aagcagtcgt tctggtcaca gctttctgtc gaatctgcac     180
ctgcgcaatg gtgaactggt gattcatgaa aaaggctttt actatatcta ttctcagacg     240
tattttcgtt ttcaggaaga aattaaagaa acaccaaaaa tgacaaaca gatggtgcag      300 tacatttaca atacaccag ttacccggac ccgattctgc tgatgaaaag cgcccgtaac      360
tcatgctgga gcaaagacgc tgaatatggc ctgtattcta tttatcaggg tggcatcttc     420
gaactgaaag aaaacgatcg tatttttgtt tcggtgacca cgaacacct gattgatatg      480 gatcatgaag catcgttttt cggcgcgttt ctggtcggc                           519

<210> SEQ ID NO 32
<211> LENGTH: 597
<212> TYPE: DNA
<213> ORGANISM: Artificial Sequence
<220> FEATURE:
<223> OTHER INFORMATION: synthesized, encoding a fusion protein
      comprising: a fragment of TRAIL protein, a heptapeptide derived
      from VEGF and flexible glycine steric linker.

<400> SEQUENCE: 32
cgcaaacgta aaaaaagccg tggtggtggc ggtggcacca gcaagaaac cattagcacc       60 gttcaggaaa acagcagaa tattagtccg ctggttcgtg aacgtggtcc gcagcgtgtt     120
gcagcacata ttaccggcac ccgtggtcgt agcaataccc tgagcagccc gaatagcaaa     180
aatgaaaaag cactgggtcg caaaattaat agctgggaaa gcagccgtag cggtcatagc     240
tttctgagca atctgcatct gcgtaatggt gaactggtga ttcatgaaaa aggcttttat     300
tatatttata gccagaccta ttttcgcttt caggaagaaa ttaaagaaaa taccaaaaat     360
gataaacaaa tggtgcagta tatctataaa tacaccagct atccggatcc gattctgctg     420
```

```
atgaaaagcg cacgtaatag ctgttggagc aaagatgcag aatatggtct gtatagcatt    480
tatcagggtg gcattttttga actgaaagaa aatgatcgca tttttgtgag cgtgaccaat    540
gaacatctga ttgatatgga tcatgaagcc agctttttgg gtgcatttct ggtgggt       597
```

```
<210> SEQ ID NO 33
<211> LENGTH: 690
<212> TYPE: DNA
<213> ORGANISM: Artificial Sequence
<220> FEATURE:
<223> OTHER INFORMATION: synthesized, encoding a fusion protein
      comprising: a fragment of TRAIL protein, a heptapeptide derived
      from VEGF, fragments of tumstatin, a steric glycine linker and
      sequences of cleavage sites recognized by MMP and uPA.

<400> SEQUENCE: 33
cgtaaacgta aaaaagccg tggtggtggt ggcggtcgtg ttgcagcaca tattaccggc     60
acccgtggtc gtagcaatac cctgagcagc ccgaatagca aaaatgaaaa agcactgggt   120
cgcaaaatta atagctggga aagcagccgt agcggtcata gctttctgag caatctgcat   180
ctgcgtaatg gtgaactggt gattcatgaa aaaggctttt attatattta tagccagacc   240
tattttcgct tcaggaaga aattaaagaa ataccaaaa atgataaaca aatggtgcag     300
tacatttaca aatataccag ctatccggat ccgattctgc tgatgaaaag cgcacgtaat   360
agctgttgga gcaaagatgc agaatatggt ctgtatagca tttatcaggg tggcattttt   420
gaactgaaag aaaatgatcg cattttttgtg agcgtgacca atgaacatct gattgatatg   480
gatcatgaag ccagcttttt tggtgcattt ctggttggtg gcggtggtcc gctgggtctg   540
gcaggtcgtg ttgttcgtac catgccgttt ctgttttgca atgttaatga tgtgtgcaat   600
tttgccagcc gcaatgatta tagctattgg ctgtgcaatt attatagcaa tagctatagc   660
ttttggctgg ctagtctgaa tccggaacgt                                    690
```

```
<210> SEQ ID NO 34
<211> LENGTH: 561
<212> TYPE: DNA
<213> ORGANISM: Artificial Sequence
<220> FEATURE:
<223> OTHER INFORMATION: synthesized, encoding a fusion protein
      comprising: a fragment of TRAIL protein, two sequences of
      heptapeptide derived from VEGF, a steric glycine linker and a
      sequence of cleavage site recognized by MMP.

<400> SEQUENCE: 34
cgcaaacgta aaaaagccg tccgctgggt attgccggtg aacgtaaacg caaaaaatct     60
cgtggtggtg gtggcggtcg tgttgcagca catattaccg gcacccgtgg tcgtagcaat   120
accctgagca gccgaatag caaaaatgaa aaagccctgg tcgcaaaat taatagctgg    180 gaaagcagcc gtagcggtca tagctttctg agcaatctgc atctgcgtaa tggtgaactg   240
gtgattcatg aaaaaggctt ttattatatt tatagccaga cctatttttcg ctttcaggaa   300 gaaattaaag aaaacaccaa aaatgataaa caaatggtgc agtatatcta taaatacacc   360
agctatccgg atccgattct gctgatgaaa agcgcacgta atagctgttg gagcaaagat   420
gcagaatatg gcctgtatag catttatcag ggtggcattt ttgaactgaa agaaaatgat   480 cgcattttttg tgagcgtgac caatgaacat ctgattgata tggatcatga agccagcttt   540
tttggtgcat ttctggtggg t                                             561
```

```
<210> SEQ ID NO 35
```

<211> LENGTH: 561
<212> TYPE: DNA
<213> ORGANISM: Artificial Sequence
<220> FEATURE:
<223> OTHER INFORMATION: synthesized, encoding a fusion protein
comprising: a fragment of TRAIL protein, two sequences of
heptapeptide derived from VEGF, sequences of cleavage sites
recognized by MMP and uPa and single glutamic acid and glycine
residues.

<400> SEQUENCE: 35

```
cgtaaacgta aaaaagccg tgttgttcgt ccgctgggta ttgccggtga acgtaaacgc    60
aaaaaatcac gtggtggtcg tgttgcagca catattaccg gcacccgtgg tcgtagcaat   120
accctgagca gcccgaatag caaaaatgaa aaagcactgg gtcgcaaaat taatagctgg   180
gaaagcagcc gtagcggtca tagctttctg agcaatctgc atctgcgtaa tggtgaactg   240
gtgattcatg aaaaaggctt ttattatatt tatagccaga cctatttccg ctttcaggaa   300
gaaattaaag aaaataccaa aaatgataaa caaatggtgc agtacattta caaatatacc   360
agctatccgg atccgattct gctgatgaaa agcgcacgta atagctgttg gagcaaagat   420
gcagaatatg gtctgtatag catttatcag ggtggcattt ttgaactgaa agaaaatgat   480
cgcattttg tgagcgtgac caatgaacat ctgattgata tggatcatga agccagcttt   540
tttggtgcat ttctggttgg t                                             561
```

<210> SEQ ID NO 36
<211> LENGTH: 666
<212> TYPE: DNA
<213> ORGANISM: Artificial Sequence
<220> FEATURE:
<223> OTHER INFORMATION: synthesized, encoding a fusion protein
comprising: a fragment of TRAIL protein, two sequences of
heptapeptide derived from VEGF, sequences of cleavage sites
recognized by MMP and uPa and cysteine flexible steric linker.

<400> SEQUENCE: 36

```
cgtaaacgta aaaaagccg tgttgttcgt ccgctgggta ttgcaggtga acgtaaacgt    60
aaaaaaagcc gtggtggtgg ttgtgcagca gcatgtgcag catgtaccag cgaagaaacc   120
attagcaccg ttcaggaaaa acagcagaat attagcccgc tggttcgtga acgtggtccg   180
cagcgtgttg cagcacatat taccggtacc cgtggtcgta gcaataccct gagcagcccg   240
aatagcaaaa atgaaaaagc actgggtcgt aaaattaata gctgggaaag cagccgtagc   300
ggtcatagct ttctgagcaa tctgcatctg cgtaatggtg aactggttat tcatgaaaaa   360
ggttttttatt atatttatag ccagacctat tttcgttttc aggaagaaat taagaaaat    420
accaaaaatg ataaacagat ggttcagtat atttataaat ataccagcta tccggatccg   480
attctgctga tgaaaagcgc acgtaatagc tgttggagca agatgcaga atatggtctg   540
tatagcattt atcagggtgg tatttttgaa ctgaaagaaa tgatcgtat tttgttagc    600
gttaccaatg aacatctgat tgatatggat catgaagcaa gctttttggg tgcatttctg   660
gttggt                                                              666
```

<210> SEQ ID NO 37
<211> LENGTH: 505
<212> TYPE: DNA
<213> ORGANISM: Artificial Sequence
<220> FEATURE:
<223> OTHER INFORMATION: synthesized, encoding a fusion protein
comprising: a fragment of TRAIL and a sequence being a ligand of
CD13.

<400> SEQUENCE: 37

```
tgtaatggtc gttgtccgca gcgtgttgca gcacatatta ccggcacccg tggtcgtagc    60
aatacgctga gcagcccgaa tagcaaaaat gaaaaagccc tgggtcgcaa aattaatagc   120
tgggaaagca gccgtagcgg tcatagcttt ctgagcaatc tgcatctgcg taatggtgaa   180
ctggtgattc atgaaaaagg cttttattat atttatagcc agacctattt tcgctttcag   240
gaagaaatta agaaaacac caaaaatgat aaacaaatgg tgcagtatat ctataaatac   300
accagctatc cggatccgat tctgctgatg aaaagcgcac gtaatagctg ttggagcaaa   360
gatgcagaat atggcctgta tagcatttat cagggtggca tttttgaact gaaagaaaat   420
gatcgcattt ttgtgagcgt gaccaatgaa catctgattg atatggatca tgaaagccag   480
ctttttttggt gcatttctgg tgggt                                         505
```

<210> SEQ ID NO 38
<211> LENGTH: 600
<212> TYPE: DNA
<213> ORGANISM: Artificial Sequence
<220> FEATURE:
<223> OTHER INFORMATION: synthesized, encoding a fusion protein
  comprising: a fragment of TRAIL, a sequence being a ligand of CD13
  and a sequence of flexible glycine-serine linker.

<400> SEQUENCE: 38

```
tgtgaatgtg gcggtgaatg tttttgtggt ggcggtagca ccagtgaaga aaccattagc    60
accgttcaag aaaaacagca gaatattagt ccgctggttc gtgaacgtgg tccgcagcgt   120
gttgcagcac atattaccgg cacccgtggt cgtagcaata ccctgagcag cccgaatagc   180
aaaaatgaaa aagcactggg tcgcaaaatc aatagctggg aaagcagccg tagcggtcat   240
agctttctga gcaatctgca tctgcgtaat ggtgaactgg tgattcatga aaaaggcttc   300
tactatatct acagccagac ctatttttcgc ttccaagaag aaatcaaaga gaacaccaaa   360
aacgacaaac aaatggtgca gtacatctac aaatatacca gctatccgga tccgattctg   420
ctgatgaaaa gcgcacgtaa tagctgttgg agcaaagatg cagaatatgg tctgtatagc   480
atttatcagg gtggcatctt tgagctgaaa gaaaatgatc gcatctttgt tagcgtgacc   540
aacgaacatc tgatcgatat ggatcatgaa gccagctttt ttggtgcatt tctggtgggt   600
```

<210> SEQ ID NO 39
<211> LENGTH: 576
<212> TYPE: DNA
<213> ORGANISM: Artificial Sequence
<220> FEATURE:
<223> OTHER INFORMATION: synthesized, encoding a fusion protein
  comprising: a fragment of TRAIL, a sequence of PDGF fragment and
  sequences of cleavage sites recognized by urokinase uPA and
  metalloprotease MMP.

<400> SEQUENCE: 39

```
tatggtcgtc cgcgtcagag cggtaaaaaa cgtaaacgta aacgcctgaa accgacccgt    60
gttgttcgtc cgctgggtct ggcaggtccg cagcgtgttg cagcacatat taccggcacc   120
cgtggtcgta gcaatacccct gagcagcccg aatagcaaaa atgaaaaagc cctgggtcgt   180
aaaattaata gctgggaaag cagccgtagc ggtcatagct ttctgagcaa tctgcatctg   240
cgtaatggcg aactggtgat tcatgaaaaa ggcttttatt atatttatag ccagacctat   300
tttcgctttc aggaagaaat taagaaaat ccaaaaatg ataaacaaat ggtgcagtat   360
atctataaat ataccagcta tccggatccg attctgctga tgaaaagcgc acgtaatagc   420
```

```
tgttggagca aagatgccga atatggtctg tatagcattt atcagggtgg cattttttgaa    480 ctgaaagaaa atgatcgcat ttttgtgagc gtgaccaatg aacatctgat tgatatggat    540
catgaagcca gcttttttgg tgcatttctg gttggt                              576
```

<210> SEQ ID NO 40
<211> LENGTH: 648
<212> TYPE: DNA
<213> ORGANISM: Artificial Sequence
<220> FEATURE:
<223> OTHER INFORMATION: synthesized, encoding a fusion protein
      comprising: a fragment of TRAIL, a fragment of PDGF and sequences
      of cleavage sites recognized by urokinase uPA and metalloprotease
      MMP.

<400> SEQUENCE: 40

```
tatggtcgtc cgcgtcagag cggtaaaaaa cgtaaacgta aacgcctgaa accgacccgt    60
gttgttcgtc cgctgggtct ggcaggcacc agcgaagaaa ccattagcac cgttcaggaa    120
aaacagcaga atattagtcc gctggttcgt gaacgtggtc cgcagcgtgt tgcagcacat    180
attaccggca cccgtggtcg tagcaatacc ctgagcagcc cgaatagcaa aaatgaaaaa    240
gcactgggtc gcaaaattaa tagctgggaa agcagccgta gcggtcatag ctttctgagc    300
aatctgcatc tgcgtaatgg tgaactggtg attcatgaaa aaggctttta ttatatttat    360
agccagacct attttcgctt tcaggaagaa attaagaaa ataccaaaaa tgataaacaa    420
atggtgcagt atatctataa atacaccagc tatccggatc cgattctgct gatgaaaagc    480
gcacgtaata gctgttggag caaagatgca gaatatggtc tgtatagcat ttatcagggt    540 ggcattttttg aactgaaaga aaatgatcgc attttttgtga gcgtgaccaa tgaacatctg    600
attgatatgg atcatgaagc cagcttttttt ggtgcatttc tggtgggt                648
```

<210> SEQ ID NO 41
<211> LENGTH: 678
<212> TYPE: DNA
<213> ORGANISM: Artificial Sequence
<220> FEATURE:
<223> OTHER INFORMATION: synthesized, encoding a fusion protein
      comprising: a fragment of TRAIL, a PDGF fragment, sequences of
      cleavage sites recognized by urokinase uPA and metalloprotease MMP
      and a flexible glycine-cysteine-alanine linker.

<400> SEQUENCE: 41

```
tatggtcgtc cgcgtcagag cggtaaaaaa cgtaaacgta aacgtctgaa accgacccgt    60
gttgttcgtc cgctgggtct ggcaggtggt ggttgtgcag cagcatgtgc agcatgtacc    120
agcgaagaaa ccattagcac cgttcaggaa aaacagcaga atattagccc gctggttcgt    180
gaacgtggtc cgcagcgtgt tgcagcacat attaccggta cccgtggtcg tagcaatacc    240
ctgagcagcc cgaatagcaa aaatgaaaaa gcactgggtc gtaaaattaa tagctgggaa    300
agcagccgta gcggtcatag ctttctgagc aatctgcatc tgcgtaatgg tgaactggtt    360
attcatgaaa aaggtttttta ttatatttat agccagacct attttcgttt tcaggaagaa    420 attaagaaa ataccaaaaa tgataaacag atggttcagt atatttataa ataccagc      480 tatccggatc cgattctgct gatgaaaagc gcacgtaata gctgttggag caaagatgca    540
gaatatggtc tgtatagcat ttatcagggt ggtattttttg aactgaaaga aaatgatcgt    600 attttttgtta gcgttaccaa tgaacatctg attgatatgg atcatgaagc aagctttttt    660
ggtgcatttc tggttggt                                                  678
```

-continued

<210> SEQ ID NO 42
<211> LENGTH: 651
<212> TYPE: DNA
<213> ORGANISM: Artificial Sequence
<220> FEATURE:
<223> OTHER INFORMATION: synthesized, encoding a fusion protein
      comprising: a fragment of TRAIL, fragments of tumstatine,
      sequences of cleavage sites recognized by urokinase uPA and
      metalloprotease MMP and a flexible linker consisting of 3 glycine
      residues.

<400> SEQUENCE: 42

```
accatgccgt tctgttttg caatgttaat gatgtgtgca attttgccag ccgcaatgat      60
tatagctatt ggctgtgcaa ttattatagc aatagctata gcttttggct ggcttctctg     120
aatccggaac gtgttgttcg tccgctgggt ctggcaggcg gtggtggtcg tgttgcagca    180
catattaccg gcacccgtgg tcgtagcaat accctgagca gcccgaatag caaaaatgaa    240
aaagcactgg gtcgcaaaat taatagctgg gaaagcagcc gtagcggtca tagctttctg    300
agcaatctgc atctgcgtaa tggtgaactg gtgattcatg aaaaaggctt ttattatatt    360
tatagccaga cctatttccg ctttcaggaa gaaattaaag aaaataccaa aatgataaa     420
caaatggtgc agtacattta caaatatacc agctatccgg atccgattct gctgatgaaa    480
agcgcacgta atagctgttg gagcaaagat gcagaatatg gtctgtatag catttatcag    540
ggtggcattt tgaactgaa agaaaatgat cgcattttg tgagcgtgac caatgaacat      600
ctgattgata tggatcatga agccagcttt tttggtgcat ttctggttgg t             651
```

<210> SEQ ID NO 43
<211> LENGTH: 660
<212> TYPE: DNA
<213> ORGANISM: Artificial Sequence
<220> FEATURE:
<223> OTHER INFORMATION: synthesized, encoding a fusion protein
      comprising: a fragment of TRAIL, fragments of tumstatin, cleavage
      sites recognized by urokinase uPA and metalloprotease MMP and
      flexible glycine linkers.

<400> SEQUENCE: 43

```
tgcaattatt atagcaatag ctatagcttt tggctggcaa gcctgaatcc ggaacgtgtt     60
gttcgtccgc tgggtctggc tggggggtggc ggtcgtgttg cagcacatat taccggcacc   120
cgtggtcgta gcaataccct gagcagcccg aatagcaaaa atgaaaaagc actgggtcgc   180
aaaattaata gctgggaaag cagccgtagc ggtcatagct ttctgagcaa tctgcatctg   240
cgtaatggtg aactggtgat tcatgaaaaa ggcttttatt atatttatag ccagacctat    300
tttcgctttc aggaagaaat taagaaaat accaaaaatg ataaacaaat ggtgcagtac    360
atttacaaat ataccagcta tccggatccg attctgctga tgaaaagcgc acgtaatagc    420
tgttggagca aagatgcaga atatggtctg tatagcattt atcagggtgg cattttgaa    480
ctgaaagaaa atgatcgcat ttttgtgagc gtgaccaatg aacatctgat tgatatggat    540
catgaagcca gcttttttgg tgcatttctg gttggtggcg gtggtactat gccgtttctg    600
ttttgcaatg ttaatgatgt gtgcaatttt gccagccgca atgattatag ctattggctg   660
```

<210> SEQ ID NO 44
<211> LENGTH: 543
<212> TYPE: DNA
<213> ORGANISM: Artificial Sequence
<220> FEATURE:
<223> OTHER INFORMATION: synthesized, encoding a fusion protein
      comprising: a fragment of TRAIL, a fragment of EGF and sequences
      of cleavage sites recognized by urokinase uPA and metalloprotease

MMP.

<400> SEQUENCE: 44

```
ctgggtctgc gtagcctgcg tgaacgtgtt gttcgtccgc tgggtctggc aggtccgcag      60
cgtgttgcag cacatattac cggcacccgt ggtcgtagca ataccctgag cagcccgaat     120
agcaaaaatg aaaaagccct gggtcgtaaa attaatagct gggaaagcag ccgtagcggt     180
catagctttc tgagcaatct gcatctgcgt aatggcgaac tggtgattca tgaaaaaggc     240
ttttattata tttatagcca gacctatttt cgctttcagg aagaaattaa agaaaatacc     300
aaaaatgata acaaatggt gcagtatatc tataaatata ccagctatcc ggatccgatt     360
ctgctgatga aaagcgcacg taatagctgt tggagcaaag atgccgaata tggtctgtat     420
agcatttatc agggtggcat ttttgaactg aaagaaaatg atcgcatttt tgtgagcgtg     480
accaatgaac atctgattga tatggatcat gaagccagct tttttggtgc atttctggtt     540
ggt                                                                   543
```

<210> SEQ ID NO 45
<211> LENGTH: 651
<212> TYPE: DNA
<213> ORGANISM: Artificial Sequence
<220> FEATURE:
<223> OTHER INFORMATION: synthesized, encoding a fusion protein
      comprising: a fragment of TRAIL, a fragment of EGF, cleavage sites
      recognized by urokinase uPA and metalloprotease MMP and flexible
      glycine-cysteine-alanine linker.

<400> SEQUENCE: 45

```
ctgggtctgc gtagcctgcg tgaacgtgtt gttcgtccgc tgggtctggc aggtccgggt      60
ggtggttgtg cagcagcatg tgcagcatgt accagcgaag aaaccattag caccgttcag     120
gaaaaacagc agaatattag cccgctggtt cgtgaacgtg gtccgcagcg tgttgcagca     180
catattaccg gtacccgtgg tcgtagcaat accctgagca gcccgaatag caaaaatgaa     240
aaagcactgg gtcgtaaaat taatagctgg gaaagcagcc gtagcggtca tagctttctg     300
agcaatctgc atctgcgtaa tggtgaactg gttattcatg aaaaaggttt ttattatatt     360
tataagccaga cctattttcg ttttcaggaa gaaattaaag aaaataccaa aaatgataaa     420
cagatggttc agtatattta taaatatacc agctatccgg atccgattct gctgatgaaa     480
agcgcacgta atagctgttg gagcaaagat gcagaatatg gtctgtatag catttatcag     540
ggtggtattt ttgaactgaa agaaaatgat cgtatttttg ttagcgttac caatgaacat     600
ctgattgata tggatcatga agcaagcttt tttggtgcat tctggttgg t               651
```

<210> SEQ ID NO 46
<211> LENGTH: 211
<212> TYPE: PRT
<213> ORGANISM: Artificial Sequence
<220> FEATURE:
<223> OTHER INFORMATION: synthesized, a fusion protein comprising: a
      fragment of TRAIL, two heptapeptides derived from VEGF and
      sequences of cleavage sites recognized by urokinase uPA and
      metalloprotease MMP.

<400> SEQUENCE: 46

```
Arg Lys Arg Lys Lys Ser Arg Val Val Arg Pro Leu Gly Ile Ala Gly
1               5                   10                  15

Glu Arg Lys Arg Lys Lys Ser Arg Thr Ser Glu Glu Thr Ile Ser Thr
            20                  25                  30

Val Gln Glu Lys Gln Gln Asn Ile Ser Pro Leu Val Arg Glu Arg Gly
```

```
                35                  40                  45
Pro Gln Arg Val Ala Ala His Ile Thr Gly Thr Arg Gly Arg Ser Asn
    50                  55                  60

Thr Leu Ser Ser Pro Asn Ser Lys Asn Glu Lys Ala Leu Gly Arg Lys
65                  70                  75                  80

Ile Asn Ser Trp Glu Ser Ser Arg Ser Gly His Ser Phe Leu Ser Asn
                85                  90                  95

Leu His Leu Arg Asn Gly Glu Leu Val Ile His Glu Lys Gly Phe Tyr
            100                 105                 110

Tyr Ile Tyr Ser Gln Thr Tyr Phe Arg Phe Gln Glu Glu Ile Lys Glu
        115                 120                 125

Asn Thr Lys Asn Asp Lys Gln Met Val Gln Tyr Ile Tyr Lys Tyr Thr
    130                 135                 140

Ser Tyr Pro Asp Pro Ile Leu Leu Met Lys Ser Ala Arg Asn Ser Cys
145                 150                 155                 160

Trp Ser Lys Asp Ala Glu Tyr Gly Leu Tyr Ser Ile Tyr Gln Gly Gly
                165                 170                 175

Ile Phe Glu Leu Lys Glu Asn Asp Arg Ile Phe Val Ser Val Thr Asn
            180                 185                 190

Glu His Leu Ile Asp Met Asp His Glu Ala Ser Phe Phe Gly Ala Phe
        195                 200                 205

Leu Val Gly
    210

<210> SEQ ID NO 47
<211> LENGTH: 200
<212> TYPE: PRT
<213> ORGANISM: Artificial Sequence
<220> FEATURE:
<223> OTHER INFORMATION: synthesized, a fusion protein comprising: a
      fragment of TRAIL, two heptapeptides derived from VEGF, cleavage
      sites recognized by uPA and MMP, a flexible linker promoting
      trimer formation and flexible glycine-serine linker.

<400> SEQUENCE: 47

Arg Lys Arg Lys Lys Ser Arg Val Val Arg Pro Leu Gly Ile Ala Gly
1               5                   10                  15

Glu Arg Lys Arg Lys Lys Ser Arg Gly Gly Gly Cys Ala Ala Ala Cys
                20                  25                  30

Ala Ala Cys Gly Ser Gly Gln Arg Val Ala Ala His Ile Thr Gly Thr
            35                  40                  45

Arg Gly Arg Ser Asn Thr Leu Ser Ser Pro Asn Ser Lys Asn Glu Lys
        50                  55                  60

Ala Leu Gly Arg Lys Ile Asn Ser Trp Glu Ser Ser Arg Ser Gly His
65                  70                  75                  80

Ser Phe Leu Ser Asn Leu His Leu Arg Asn Gly Glu Leu Val Ile His
                85                  90                  95

Glu Lys Gly Phe Tyr Tyr Ile Tyr Ser Gln Thr Tyr Phe Arg Phe Gln
            100                 105                 110

Glu Glu Ile Lys Glu Asn Thr Lys Asn Asp Lys Gln Met Val Gln Tyr
        115                 120                 125

Ile Tyr Lys Tyr Thr Ser Tyr Pro Asp Pro Ile Leu Leu Met Lys Ser
    130                 135                 140

Ala Arg Asn Ser Cys Trp Ser Lys Asp Ala Glu Tyr Gly Leu Tyr Ser
145                 150                 155                 160

Ile Tyr Gln Gly Gly Ile Phe Glu Leu Lys Glu Asn Asp Arg Ile Phe
```

```
                      165                 170                 175

Val Ser Val Thr Asn Glu His Leu Ile Asp Met Asp His Glu Ala Ser
            180                 185                 190

Phe Phe Gly Ala Phe Leu Val Gly
        195                 200
```

<210> SEQ ID NO 48
<211> LENGTH: 192
<212> TYPE: PRT
<213> ORGANISM: Artificial Sequence
<220> FEATURE:
<223> OTHER INFORMATION: synthesized, a fusion protein comprising: a
      fragment of TRAIL, two heptapeptides derived from VEGF, a sequence
      of cleavage site recognized by urokinase uPA, a flexible linker
      promoting trimer formation and flexible glycine-serine linker.

<400> SEQUENCE: 48

```
Arg Lys Arg Lys Lys Ser Arg Val Val Arg Lys Arg Lys Lys Ser Arg
1               5                   10                  15

Gly Gly Gly Cys Ala Ala Ala Cys Ala Ala Cys Gly Ser Gly Gln Arg
            20                  25                  30

Val Ala Ala His Ile Thr Gly Thr Arg Gly Arg Ser Asn Thr Leu Ser
        35                  40                  45

Ser Pro Asn Ser Lys Asn Glu Lys Ala Leu Gly Arg Lys Ile Asn Ser
    50                  55                  60

Trp Glu Ser Ser Arg Ser Gly His Ser Phe Leu Ser Asn Leu His Leu
65                  70                  75                  80

Arg Asn Gly Glu Leu Val Ile His Glu Lys Gly Phe Tyr Tyr Ile Tyr
                85                  90                  95

Ser Gln Thr Tyr Phe Arg Phe Gln Glu Glu Ile Lys Glu Asn Thr Lys
            100                 105                 110

Asn Asp Lys Gln Met Val Gln Tyr Ile Tyr Lys Tyr Thr Ser Tyr Pro
        115                 120                 125

Asp Pro Ile Leu Leu Met Lys Ser Ala Arg Asn Ser Cys Trp Ser Lys
    130                 135                 140

Asp Ala Glu Tyr Gly Leu Tyr Ser Ile Tyr Gln Gly Gly Ile Phe Glu
145                 150                 155                 160

Leu Lys Glu Asn Asp Arg Ile Phe Val Ser Val Thr Asn Glu His Leu
                165                 170                 175

Ile Asp Met Asp His Glu Ala Ser Phe Phe Gly Ala Phe Leu Val Gly
            180                 185                 190
```

<210> SEQ ID NO 49
<211> LENGTH: 206
<212> TYPE: PRT
<213> ORGANISM: Artificial Sequence
<220> FEATURE:
<223> OTHER INFORMATION: synthesized, a fusion protein comprising: a
      fragment of TRAIL, a PDGF fragment, sequences of cleavage sites
      recognized by uPA and MMP, a flexible glycine-cysteine-alanine
      linker promoting trimer formation and flexible glycine-serine
      linker.

<400> SEQUENCE: 49

```
Tyr Gly Arg Pro Arg Gln Ser Gly Lys Lys Arg Lys Arg Lys Arg Leu
1               5                   10                  15

Lys Pro Thr Arg Val Val Arg Pro Leu Gly Ile Ala Gly Glu Gly Gly
            20                  25                  30

Gly Cys Ala Ala Ala Cys Ala Ala Cys Gly Ser Gly Gln Arg Val Ala
        35                  40                  45
```

Ala His Ile Thr Gly Thr Arg Gly Arg Ser Asn Thr Leu Ser Ser Pro
 50                  55                  60

Asn Ser Lys Asn Glu Lys Ala Leu Gly Arg Lys Ile Asn Ser Trp Glu
 65                  70                  75                  80

Ser Ser Arg Ser Gly His Ser Phe Leu Ser Asn Leu His Leu Arg Asn
                 85                  90                  95

Gly Glu Leu Val Ile His Glu Lys Gly Phe Tyr Tyr Ile Tyr Ser Gln
                100                 105                 110

Thr Tyr Phe Arg Phe Gln Glu Glu Ile Lys Glu Asn Thr Lys Asn Asp
            115                 120                 125

Lys Gln Met Val Gln Tyr Ile Tyr Lys Tyr Thr Ser Tyr Pro Asp Pro
        130                 135                 140

Ile Leu Leu Met Lys Ser Ala Arg Asn Ser Cys Trp Ser Lys Asp Ala
145                 150                 155                 160

Glu Tyr Gly Leu Tyr Ser Ile Tyr Gln Gly Gly Ile Phe Glu Leu Lys
                165                 170                 175

Glu Asn Asp Arg Ile Phe Val Ser Val Thr Asn Glu His Leu Ile Asp
            180                 185                 190

Met Asp His Glu Ala Ser Phe Phe Gly Ala Phe Leu Val Gly
        195                 200                 205

<210> SEQ ID NO 50
<211> LENGTH: 633
<212> TYPE: DNA
<213> ORGANISM: Artificial Sequence
<220> FEATURE:
<223> OTHER INFORMATION: synthesized, encoding a fusion protein
      comprising: a fragment of TRAIL, two heptapeptides derived from
      VEGF and sequences of cleavage sites recognized by urokinase uPA
      and metalloprotease MMP.

<400> SEQUENCE: 50
cgtaaacgta aaaaagccg tgtggtgcgt ccgctgggca ttgcgggcga acgtaaacgt      60
aaaaaaagcc gtaccagcga agaaaccatt agcaccgtgc aggaaaaaca gcagaacatt    120
agcccgctgg tgcgtgaacg tggcccgcag cgtgtggcgg cgcatattac cggcacccgt    180
ggccgtagca acaccctgag cagcccgaac agcaaaaacg aaaaagcgct gggccgtaaa    240
attaacagct gggaaagcag ccgtagcggc catagctttc tgagcaacct gcatctgcgt    300
aacggcgaac tggtgattca tgaaaaaggc ttttattata tttatagcca gacctatttt    360
cgttttcagg aagaaattaa agaaaacacc aaaaacgata acagatggt gcagtatatt     420 tataaatata ccagctatcc ggatccgatt ctgctgatga aaagcgcgcg taacagctgc    480
tggagcaaag atgcggaata tggcctgtat agcatttatc agggcggcat ttttgaactg    540
aaagaaaacg atcgtatttt tgtgagcgtg accaacgaac atctgattga tatggatcat    600
gaagcgagct ttttggcgc gtttctggtg ggc                                 633

<210> SEQ ID NO 51
<211> LENGTH: 600
<212> TYPE: DNA
<213> ORGANISM: Artificial Sequence
<220> FEATURE:
<223> OTHER INFORMATION: synthesized, encoding a fusion protein
      comprising: a fragment of TRAIL, two heptapeptides derived from
      VEGF, cleavage sites recognized by uPA and MMP, a flexible linker
      promoting trimer formation and flexible glycine-serine linker.

<400> SEQUENCE: 51

```
cgtaaacgta aaaaaagccg tgttgttcgt ccgctgggta ttgccggtga acgtaaacgc    60
aaaaaatcac gtggtggtgg ttgtgcagca gcatgtgcag cctgtggtag cggtcagcgt   120
gttgcagcac atattaccgg cacccgtggt cgtagcaata ccctgagcag cccgaatagc   180
aaaaatgaaa aagcactggg tcgcaaaatt aacagctggg aaagcagccg tagcggtcat   240
agctttctga gcaatctgca tctgcgtaat ggtgaactgg tgattcatga aaaaggcttt   300
tactacatct acagccagac ctatttccgc tttcaagaag agattaaaga aaataccaaa   360
aatgataaac aaatggtgca gtatatttac aaatatacca gctatccgga tccgatcctg   420
ctgatgaaaa gcgcacgtaa tagctgttgg agcaaagatg cagaatatgg cctgtatagc   480
atttatcagg gtggcatctt tgaactgaaa gaaaacgatc gtattttcgt gagcgtgacc   540
aatgaacatc tgatcgatat ggatcatgaa gccagctttt ttggtgcatt tctggtgggt   600
```

<210> SEQ ID NO 52
<211> LENGTH: 576
<212> TYPE: DNA
<213> ORGANISM: Artificial Sequence
<220> FEATURE:
<223> OTHER INFORMATION: synthesized, encoding a fusion protein
      comprising: a fragment of TRAIL, two heptapeptides derived from
      VEGF, a sequence of cleavage site recognized by urokinase uPA, a
      flexible linker promoting trimer formation and flexible
      glycine-serine linker.

<400> SEQUENCE: 52

```
cgtaaacgta aaaaaagccg tgttgtgcgc aaacgcaaaa aatcacgtgg tggtggttgt    60
gcagcagcat gtgcagcctg tggtagcggt cagcgtgttg cagcacatat taccggcacc   120
cgtggtcgta gcaataccct gagcagcccg aatagcaaaa atgaaaaagc actgggtcgc   180
aaaattaaca gctgggaaag cagccgtagc ggtcatagct ttctgagcaa tctgcatctg   240
cgtaatggtg aactggtgat tcatgaaaaa ggcttttact acatctacag ccagacctat   300
ttccgctttc aagaagagat taagaaaat accaaaaatg ataaacaaat ggtgcagtat   360
atttacaaat ataccagcta tccggatccg atcctgctga tgaaaagcgc acgtaatagc   420
tgttggagca aagatgcaga atatggcctg tatagcattt atcagggtgg catctttgaa   480
ctgaaagaaa acgatcgtat tttcgtgagc gtgaccaatg aacatctgat cgatatggat   540
catgaagcca gctttttggg tgcatttctg gtgggt                             576
```

<210> SEQ ID NO 53
<211> LENGTH: 676
<212> TYPE: DNA
<213> ORGANISM: Artificial Sequence
<220> FEATURE:
<223> OTHER INFORMATION: synthesized, encoding a fusion protein
      comprising: a fragment of TRAIL, a PDGF fragment, sequences of
      cleavage sites recognized by uPA and MMP, a flexible
      glycine-cysteine-alanine linker promoting trimer formation and
      flexible glycine-serine linker.

<400> SEQUENCE: 53

```
tatggtcgtc cgcgtcagag cggtaaaaaa cgtaaacgta aacgcctgaa accgacccgt    60
gttgttcgtc cgctgggtat tgccggtgaa ggtggtggtt gtgcagcagc atgtgcagcc   120
tgtggtagcg gtcagcgtgt tgcagcacat attaccggca cccgtggtcg tagcaatacc   180
ctgagcagcc cgaatagcaa aaatgaaaaa gcactgggtc gcaaaatcaa cagctgggaa   240
agcagccgta gcggtcatag ctttctgagc aatctgcatc tgcgtaatgg tgaactggtg   300
attcatgaaa aaggctttta ttacatttat agccagacct atttccgctt tcaagaagaa   360
```

```
attaaagaaa ataccaaaaa tgataaacaa atggtgcagt atatttacaa atataccagc    420
tatccggatc cgattctgct gatgaaaagc gcacgtaata gctgttggag caaagatgca    480
gaatatggtc tgtatagcat ttatcagggt ggcattttg aactgaaaga aaatgatcgc    540
atttttgtga gcgtgaccaa tgaacatctg attgatatgg atcatgaagc cagctttttt    600
ggtgcatttc tggtgggtta ataactcgag ggtacctgga gcacaagact ggcctcatgg    660
gccttccgct cactgc                                                    676
```

\<210\> SEQ ID NO 54  
\<211\> LENGTH: 4  
\<212\> TYPE: PRT  
\<213\> ORGANISM: Artificial Sequence  
\<220\> FEATURE:  
\<223\> OTHER INFORMATION: synthesized, a flexible linker

\<400\> SEQUENCE: 54

Cys Gly Ser Gly  
1

\<210\> SEQ ID NO 55  
\<211\> LENGTH: 7  
\<212\> TYPE: PRT  
\<213\> ORGANISM: Artificial Sequence  
\<220\> FEATURE:  
\<223\> OTHER INFORMATION: synthesized, sequence recognized by  
      metalloprotease MMP

\<400\> SEQUENCE: 55

Pro Leu Gly Ile Ala Gly Glu  
1               5

\<210\> SEQ ID NO 56  
\<211\> LENGTH: 8  
\<212\> TYPE: PRT  
\<213\> ORGANISM: Artificial Sequence  
\<220\> FEATURE:  
\<223\> OTHER INFORMATION: synthesized, sequence recognized by  
      metalloprotease MMP

\<400\> SEQUENCE: 56

Pro Leu Gly Leu Ala Gly Glu Pro  
1               5

\<210\> SEQ ID NO 57  
\<211\> LENGTH: 19  
\<212\> TYPE: DNA  
\<213\> ORGANISM: Artificial Sequence  
\<220\> FEATURE:  
\<223\> OTHER INFORMATION: primer complementary to T7 promotor

\<400\> SEQUENCE: 57 taatacgact cactatagg                                                  19

\<210\> SEQ ID NO 58  
\<211\> LENGTH: 19  
\<212\> TYPE: DNA  
\<213\> ORGANISM: Artificial Sequence  
\<220\> FEATURE:  
\<223\> OTHER INFORMATION: primer complementary to T7 terminator

\<400\> SEQUENCE: 58 gctagttatt gctcagcgg                                                  19

```
<210> SEQ ID NO 59
<211> LENGTH: 8
<212> TYPE: PRT
<213> ORGANISM: Artificial Sequence
<220> FEATURE:
<223> OTHER INFORMATION: glycine-rich linker for linking fusion proteins
      domains
<300> PUBLICATION INFORMATION:
<301> AUTHORS: Feng Feng-Yi
<302> TITLE: Phase and Clinical Trial of Rh-Apo2L and Apo2L-Related
      Experimental Study
<307> DATE: 2006-10-01

<400> SEQUENCE: 59

Gly Gly Gly Ser Gly Gly Ser Gly
1               5
```

ANTICANCER FUSION PROTEIN COMPRISING TRAIL AND A GROWTH FACTOR RECEPTOR INHIBITOR

RELATED APPLICATIONS

This application is a §371 national stage of PCT International Application No. PCT/EP2012/050145, filed Jan. 5, 2012, claims priority Polish Patent Application PL393578, filed Jan. 5, 2011, the contents of each of which are hereby incorporated by reference into this application.

REFERENCE TO SEQUENCE LISTING

This application incorporates-by-reference nucleotide and/or amino acid sequences which are present in the file named "150702_1947_85140_Substitute_Sequence_Listing_AWG.txt", which is 67.0 kilobytes in size, and which was created Jul. 2, 2015 in the IBM-PC machine format, having an operating system compatibility with MS-Windows, which is contained in the text file filed Jul. 2, 2015 as part of this application.

The invention relates to the field of therapeutic fusion proteins, in particular recombinant fusion proteins. More particularly, the invention relates to fusion proteins containing the fragment of a sequence of the soluble human TRAIL protein in combination with a sequence of an antiangiogenic peptide, pharmaceutical compositions containing them, their use in therapy, particularly as anticancer agents, and to polynucleotide sequences encoding the fusion proteins, expression vectors containing the polynucleotide sequences, and host cells containing these expression vectors.

TRAIL protein belonging to the cytokines family (Tumor Necrosis Factor-Related Apoptosis Inducing Ligand), also known as Apo2L (Apo2-ligand), is a potent activator of apoptosis in tumor cells and in cells infected by viruses. TRAIL is a ligand naturally occurring in the body. TRAIL protein, its amino acid sequence, coding DNA sequences and protein expression systems were disclosed for the first time in EP0835305A1.

TRAIL protein exerts its anticancer activity by binding to pro-apoptotic TRAIL surface receptors 1 and 2 (TRAIL-R1/R2) and subsequent activation of these receptors. These receptors, also known as DR4 and DR5 (death receptor 4 and death receptor 5), belong to the TNF receptor family and are overexpressed by different types of cancer cells. Activation of these receptors can induce external signaling pathway of suppressor gene p53-independent apoptosis, which by activated caspase-8 leads to the activation of executive caspases and thereby degradation of nucleic acids. Caspase-8 released upon TRAIL activation may also cause the release of Bid protein and thereby indirect activation of mitochondrial pathway, Bid protein being translocated to mitochondria, where it stimulates the release of cytochrome c, thus indirectly amplifying the apoptotic signal from death receptors.

TRAIL acts selectively on tumor cells essentially without inducing apoptosis in healthy cells which are resistant to this protein. Therefore, the enormous potential of TRAIL was recognized as an anticancer agent which acts on a wide range of different types of tumor cells, including hematologic malignancies and solid tumors, while sparing normal cells and exerting potentially relatively small side effects.

TRAIL protein is a type II membrane protein having the length of 281 amino acids, and its extracellular region comprising amino acid residues 114-281 upon cleavage by proteases forms soluble sTRAIL molecule of 20 kDa size, which is also biologically active. Both TRAIL and sTRAIL forms are capable of triggering apoptosis via interaction with TRAIL receptors present on target cells. Strong antitumour activity and very low systemic toxicity of soluble part of TRAIL molecule was demonstrated using cell lines tests.

Also, human clinical studies with recombinant human soluble TRAIL (rhTRAIL) having amino acid sequence corresponding to amino acids 114-281 of hTRAIL, known under the INN dulanermin, showed its good tolerance and absence of dose limiting toxicity.

Fragment of TRAIL shorter than 114-281 is also able to bind with membrane death receptors and induce apoptosis via these receptors, as recently reported for recombinant circularly permuted mutant of 122-281hTRAIL for example in EP 1 688 498.

Toxic effects of recombinant TRAIL protein on liver cells reported up to now appear to be associated with the presence of modification, i.e. polyhistidine tags, while untagged TRAIL showed no systemic toxicity.

However, in the course of further research and development it appeared that many cancer cells showed primary or acquired resistance to TRAIL (see for example WO2007/022214). Although the mechanism of resistance to TRAIL has not been fully understood, it is believed that it may manifest itself at different levels of TRAIL-induced apoptosis pathway, ranging from the level of cell surface receptors to the executive caspases within the signaling pathway. This resistance limits the usefulness of TRAIL as an anticancer agent.

Furthermore, in clinical trials on patients the actual effectiveness of TRAIL as a monotherapy proved to be low. To overcome this low efficiency and the resistance of tumors to TRAIL, various combination therapies with radio- and chemotherapeutic agents were designed, which resulted in synergistic apoptotic effect (WO2009/002947; A. Almasan and A. Ashkenazi, Cytokine Growth Factor Reviews 14 (2003) 337-348; R K Srivastava, Neoplasis, Vol 3, No 6, 2001, 535-546, Soria J C et al., J. Clin. Oncology, Vol 28, No 9 (2010), p. 1527-1533). The use of rhTRAIL for cancer treatment in combination with selected conventional chemotherapeutic agents (paclitaxel, carboplatin) and monoclonal anti-VEGF antibodies are described in WO2009/140469. However, such a combination necessarily implies well-known deficiencies of conventional chemotherapy or radiotherapy.

Moreover, the problem connected with TRAIL therapy has proved to be its low stability and rapid elimination from the body after administration.

One of the targets in cancer therapy is also the inhibition of tumor angiogenesis. Angiogenesis (neouvascularisation) is a pathological, time-unlimited process of developing new blood vessels that supply tumors with oxygen and nutrients. Angiogenesis is indispensable for the growth and expansion of the tumor and promoting its metastasis.

Beneficial effect of inhibition of tumor angiogenesis in cancer therapy is known. Attempts were made to the clinical use of substances that inhibit or regulate the process of angiogenesis, both as a cancer therapy and a complementary cancer therapy.

Inhibitors of angiogenesis are known, both endogenous ones naturally present in the human body and numerous exogenous antiangiogenic substances. Among them there are known proteinaceous inhibitors of angiogenesis, including proteolytic fragments of endogenous proteins. As examples, the protein inhibitors of angiogenesis such as angiostatin (a fragment of plasminogen), endostatin (C-terminal fragment of collagen XVIII), calreticulin, vasostatin—a calreticulin fragment, a fragment of prolactin, a fragment of metalloproteinase 2, or tumstatin—a fragment of collagen IV, can be mentioned (Cao Y. Angiogenesis modulates adipogenesis and obesity. *J Clin Invest.* 2007; 117(9):2362-2368, Folkman J. Angiogenesis: an organizing principle for drug discovery? *Nat Rev Drug Discov.* 2007; 6:273-286).

For example, tumstatin is a peptide of the size of 28 kDa—a fragment of collagen type IV, capable of binding to integrin $\alpha_v\beta_3$ and preventing angiogenesis by inhibition of endothelial cells proliferation. Moreover, tumstatin independently inhibits activation of Focal Adhesion Kinase (FAK) and phosphatidylinositol 3-kinase PI3 and protein kinase PKB/Akt.

Antiangiogenic activity may be also exerted by inhibition of pro-angiogenic proteins, such as Vascular Endothelial Growth Factor (VEGF), which acts through receptors located on vascular endothelium and which is the main stimulator of neoangiogenesis.

In clinical treatment, including cancer therapy, have already been used as antiangiogenic factors certain substances directed against VEGF, such as monoclonal antibodies bevacizumab and ranibizumab. Other proangiogenic factors stimulating the proliferation and migration of endothelial cells independently of receptors located on the endothelium are also known, which include for example, cytokines such as Platelet-Derived Growth Factors PDGF and epidermal growth factor EGF, TNF, and angiopoietin.

In the process of angiogenesis there is also involved the enzyme aminopeptidase N (APN/CD13), which is a transmembrane metalloprotease. It is known that inhibition of this enzyme may lead to inhibition of neoplastic processes. A number natural and synthetic inhibitors of aminopeptidase N are known. (Bayou's B., Dauzonne D., Aminopeptidase-N/CD13 (EC 3.4.11.2) inhibitors: chemistry, biological evaluations, and therapeutic prospects. Medical Research Review, 2006, 26, (1), 88-130).

Natural inhibitors of APN/CD13 include mainly substances produced by microorganisms. As an representative, among others bestatin, curcumin, and apigenin may be mentioned. It was also found that a short peptide containing CNGRC motif is able to efficiently bind to CD13 (Arap et al., Science, 279:377-380, 1998).

Many of the antiangiogenic substances are currently at different stages of investigations, including clinical trials. However, known therapies aimed at inhibiting angiogenesis have many well-known disadvantages. For example, the benefits of therapeutic monoclonal antibody bevacizumab in the treatment of breast cancer have been recently questioned. Many antiangiogenic drugs show, for example, a very short half-life, low solubility, poor bioavailability and toxic side effects.

Safety of anti-angiogenic drugs is of special importance because of prolonged use and lack of selectivity of therapy. Strong need for an effective therapeutic and the nature of oncological diseases necessitate a simplified registration procedure for such group of drugs, therefore it is impossible to know all the side effects and drawbacks of the drug. Although, contrary to the chemiotherapeutics, which are directed to all fast proliferating cells, antiangiogenic drugs are directed at different stages of the formation of blood vessels, which results in reduction of the toxicity of therapy. However, there is still a need of anticancer therapy which is aimed at inhibiting angiogenesis while ensuring selectivity against tumor cells. There is therefore a need for new antiangiogenic anticancer therapies with improved toxicological characteristics.

Constructed fusion protein containing sequences of an angiogenesis inhibitor vasostatin and TRAIL114-281 linked with a metalloprotease cleavage site linker was described as exhibiting apoptosis-inducing effect in tumor cells by A. I. Guo et al in Chinese Journal of Biochemistry and Molecular Biology 2008, vol. 24(10), 925-930.

Constructed fusion protein containing sequences of an angiogenesis inhibitor calreticulin and TRAIL114-281 was described as exhibiting apoptosis-inducing effect in tumor cells in CN1609124A.

CN 1256347C discloses fusion protein composed of kininogen D5 60-148 and TRAIL 114-281.

Constructed fusion protein containing sequences of an angiogenesis inhibitor kininostatin, vasostatin and canstatin attached to N- or C-terminus of TRAIL114-281 linked with linker encoding GGGSGGSG (SEQ ID NO: 59) are mentioned in Feng Feng-Yi "Phase and Clinical Trial of Rh-Apo2L and Apo2L-Related Experimental Study", Ph.D. degree thesis, Chinese Peking Union Medical, 2006-10-01; www.lw23.com/lunwen__957708432.

Constructed fusion protein containing sequences Tumstatin 183-230 of an angiogenesis inhibitor tumstatin and TRAIL114-281 was described as exhibiting Induction of apoptosis of pancreatic cancer cells by N. Ren et al in Academic Journal of Second Military Medical University 2008, vol. 28(5), 676-478.

US2005/244370 and corresponding WO2004/035794 disclose the construct of TRAIL95-281 as an effector domain linked by a peptide linker with extracellular part of another member of TNF family ligands CD40 as a cell surface binding domain. It is stated that activation of the construct is via binding of its CD40 part.

The present invention provides a solution of this problem by providing novel fusion proteins that comprise a domain derived from TRAIL and a short effector peptide domain having the antiangiogenic activity and not including TRAIL fragments, wherein the effector peptide potentiates or complements the action of TRAIL.

Proteins according to the invention are directed selectively to cancer cells, where the individual elements of the protein exert their effects, in particular the effector peptides inhibit tumor angiogenesis. Delivery of the proteins of the invention into the tumour environment allows to minimize the toxicity against healthy cells in the body as well as the side effects and to reduce the frequency of administration. In addition, targeted therapy with the use of proteins according to the invention allows to avoid the problem of low efficiency of previously known nonspecific antiangiogenic therapies caused by low permeability of blood vessels.

Moreover, it turned out that in many cases the fusion proteins of the invention are more potent than soluble TRAIL and its variants including a fragment of the sequence. Until now, known effector peptides used in the fusion protein of the invention were not used in medicine as such because of unfavorable kinetics, rapid degradation by nonspecific proteases or accumulation in the body caused by lack of proper sequence of activation of pathways which are necessary to enable the proper action of the efector peptide at target site. Incorporation of the effector peptide into the fusion protein allows their selective delivery to the site where their action is desirable. Furthermore, the attachment of efector peptide increases the mass of protein, resulting in prolonged half-life and increased retention of protein in the tumour and its enhanced efficiency. Additionally, in many cases, novel fusion proteins also overcome resistance to TRAIL.

DESCRIPTION OF FIGURES

The invention will now be described in detail with reference to the Figures of the drawing.

DETAILED DESCRIPTION OF THE INVENTION

Figure 1:
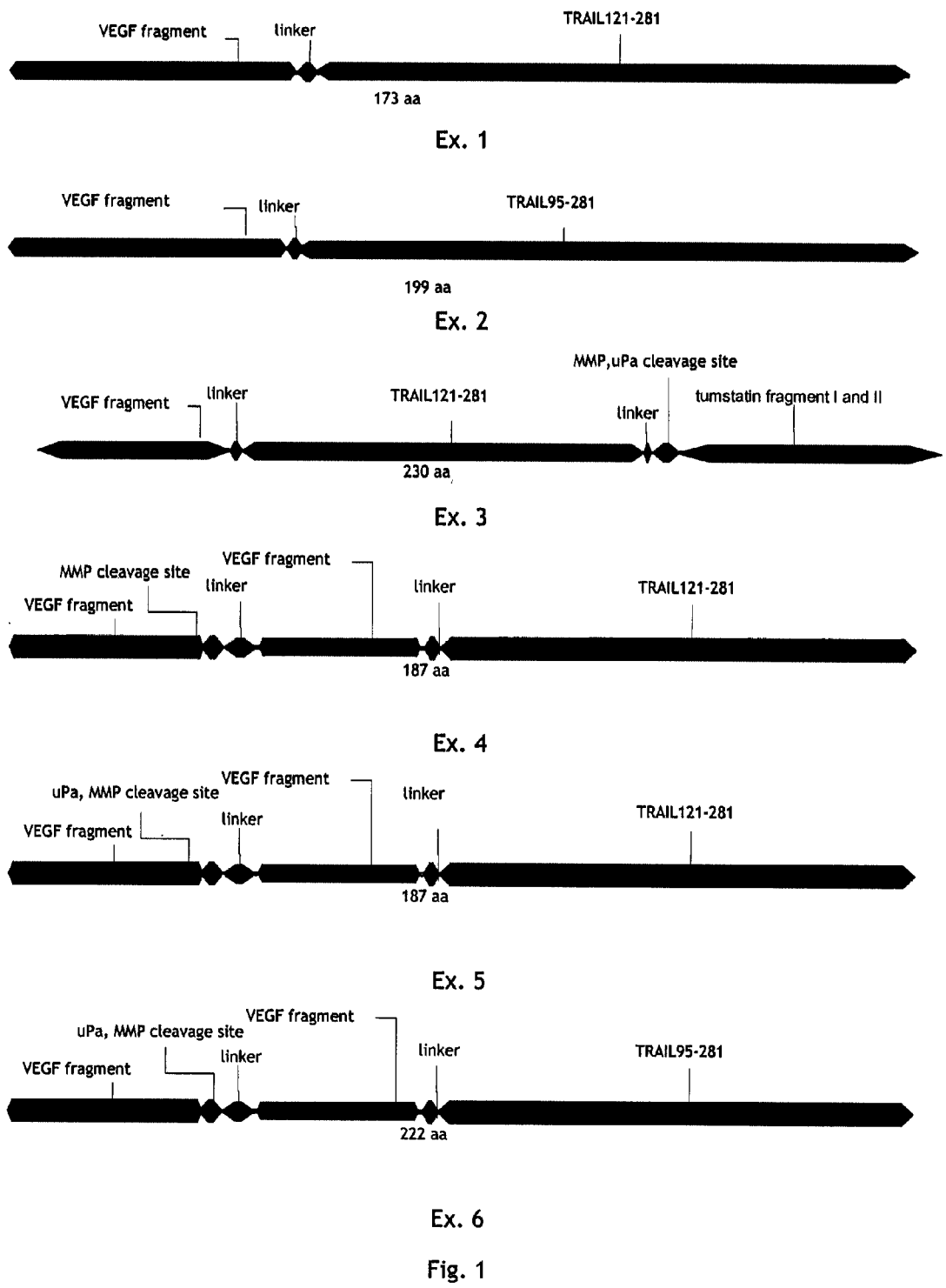
FIG. 1 presents a schematic structure of fusion proteins of the invention according to Ex. 1, Ex. 2, Ex. 3, Ex. 4, Ex. 5 and Ex. 6.

The invention relates to a fusion protein comprising:
domain (a) which is the functional fragment of a sequence of soluble hTRAIL protein, which fragment begins with an amino acid at a position not lower than hTRAIL95 or a homolog of said functional fragment having at least 70% sequence identity, and
domain (b) which is a sequence of a antiangiogenic effector peptide,
wherein the sequence of the domain (b) is attached at the C-terminus and/or N-terminus of domain (a);
with the proviso that fusion proteins are excluded wherein effector peptide is selected from the group consisting of calreticulin, tumstatin 183-230, kininogen D5, vasostatin, kininostatin and canstatin.

The term "the functional soluble fragment of a sequence of soluble hTRAIL" should be understood as denoting any such fragment of soluble hTRAIL that is capable of inducing apoptotic signal in mammalian cells upon binding to its receptors on the surface of the cells.

It will be also appreciated by a skilled person that the existence of at least 70% homology of the TRAIL sequence is known in the art.

It should be understood that domain (b) of the effector peptide in the fusion protein of the invention is neither hTRAIL protein nor a part or fragment of hTRAIL protein.

The term "peptide" in accordance with the invention should be understood as a molecule built from plurality of amino acids linked together by means of a peptide bond. Thus, the term "peptide" according to the invention includes oligopeptides, polypeptides and proteins.

In the present invention the aminoacid sequences of peptides will be presented in a conventional manner adopted in the art in the direction from N-terminus (N-end) of the peptide towards its C-terminus (C-end). Any sequence will thus have its N-terminus on the left side and C-terminus on the right side of its linear presentation.

The fusion protein of the invention incorporates at least one domain (b) of the effector peptide, attached at the C-terminus or N-terminus of domain (a).

In a particular embodiment, the domain (a) is a fragment of hTRAIL sequence, beginning with an amino acid from the range of hTRAIL95 to hTRAIL121, inclusive, and ending with the amino acid hTRAIL 281.

In particular, domain (a) may be selected from the group consisting of sequences corresponding to hTRAIL95-281, hTRAIL119-281, hTRAIL120-281 and hTRAIL121-281. It will be evident to those skilled in the art that hTRAIL95-281, hTRAIL119-281, hTRAIL120-281 and hTRAIL121-281 represent a fragment of human TRAIL protein starting with amino acid marked with the number 95, 119, 120 and 121, respectively, in the known sequence of hTRAIL (SEQ. No. 16) published in GenBank under Accession No P50591.

In another particular embodiment, the domain (a) is a homolog of functional fragment of soluble hTRAIL protein sequence beginning at amino acid position not lower than hTRAIL95 and ending at amino acid hTRAIL281, the sequence of which is at least in 70%, preferably in 85%, identical to original sequence.

In specific variants of this embodiment the domain (a) is a homolog of a fragment selected from the group consisting of sequences corresponding to hTRAIL95-281, hTRAIL114-281, hTRAIL116-281, hTRAIL120-281, hTRAIL121-281 and hTRAIL122-281.

It should be understood that a homolog of a hTRAIL fragment is a variation/modification of the amino acid sequence of this fragment, wherein at least one amino acid is changed, including 1 amino acid, 2 amino acids, 3 amino acids, 4 amino acids, 5 amino acids, 6 amino acids, and not more than 15% of amino acids, and wherein a fragment of the modified sequence has preserved functionality of the hTRAIL sequence, i.e. the ability of binding to cell surface death receptors and inducing apoptosis in mammalian cells. Modification of the amino acid sequence may include, for example, substitution, deletion and/or addition of amino acids.

Preferably, the homolog of hTRAIL fragment having modified sequence shows a modified affinity to the death receptors DR4 (TRAIL-R1) or DR5 (TRAIL-R2) in comparison with the native fragment of hTRAIL.

The term "modified affinity" refers to an increased affinity and/or affinity with altered receptor selectivity.

Preferably, the homolog of the fragment of hTRAIL having modified sequence shows increased affinity to the death receptors DR4 and DR5 compared to native fragment of hTRAIL.

Particularly preferably, the homolog of fragment of hTRAIL having modified sequence shows increased affinity to the death receptor DR5 in comparison with the death receptor DR4, i.e. an increased selectivity DR5/DR4.

Also preferably, the homolog of fragment of hTRAIL having modified sequence shows an increased selectivity towards the death receptors DR4 and/or DR5 in relation to the affinity towards the receptors DR1 (TRAIL-R3) and/or DR2 (TRAIL-R4).

Modifications of hTRAIL resulting in increased affinity and/or selectivity towards the death receptors DR4 and DR5 are known to those skilled in the art, for example from the publication Tur V, van der Sloot A M, Reis C R, Szegezdi E, Cool R H, Samali A, Serrano L, Quax W J. DR4-selective tumor necrosis factor-related apoptosis-inducing ligand (TRAIL) variants obtained by structure-based design. J. Biol. Chem. 2008 Jul. 18; 283(29):20560-8, which describes the D218H mutation having increased selectivity towards DR4, or Gasparian M E, Chemyak B V, Dolgikh D A, Yagolovich A V, Popova E N, Sycheva A M, Moshkovskii S A, Kirpichnikov M P. Generation of new TRAIL mutants DR5-A and DR5-B with improved selectivity to death receptor 5, Apoptosis. 2009 June; 14(6):778-87, which describes the D269H mutation having a reduced affinity towards DR4. hTRAIL mutants resulting in increased affinity towards one receptor selected from the DR4 and DR5 comparing with DR1 and DR2 receptors and increased affinity towards the receptor DR5 comparing with DR4 are also described in WO2009077857 and WO2009066174.

Suitable mutations are one or more mutations in the positions of native hTRAL selected from the group consisting of 131, 149, 159, 193, 199, 201, 204, 204, 212, 215, 218 and 251, in particular, mutations involving the substitution of an amino acid with a basic amino acid such as lysine, histidine or arginine, or amino acid such as glutamic acid or aspargic acid. Particularly one or more mutations selected from the group consisting of G131R, G131K, R149I, R149M, R149N, R149K, S159R, Q193H, Q193K, N199H, N199R, K201H, K201R, K204E, K204D, K204L, K204Y, K212R, S215E, S215H, S215K, S215D, D218Y, D218H, K251D, K251E and K251Q, as described in WO2009066174, may be specified.

Suitable mutations are also one or more mutations in the positions of native hTRAL selected from the group consisting of 195, 269 and 214, particularly mutations involving the substitution of an amino acid with a basic amino acid such as lysine, histidine or arginine. Particularly one or more mutations selected from the group consisting of D269H, E195R, and T214R, as described in WO2009077857, may be specified.

In a particular embodiment, the domain (a) which is a homolog of the fragment of hTRAIL is selected from D218H mutant of the native TRAIL sequence, as described in WO2009066174, or the Y189N-R191K-Q193R-H264R-I266R-D269H mutant of the native TRAIL sequence, as described in Gasparian M E, Chemyak B V, Dolgikh D A, Yagolovich A V, Popova E N, Sycheva A M, Moshkovskii S A, Kirpichnikov M P. Generation of new TRAIL mutants DR5-A and DR5-B with improved selectivity to death receptor 5, Apoptosis. 2009 June; 14(6):778-87.

Domain (b) may be in particular selected from the following group:
    inhibitors of receptors for growth factors selected from receptors for VEGF, PDGF and EGF;
    tumstatin or fragments thereof other than fragment 183-230 and
    inhibitors of aminopeptidase N (CD13).

Within the group of inhibitors of receptors for growth factors the effector peptide of domain (b) may be a fragment of human vascular endothelial growth factor VEGF which binds the VEGF receptor competitively to the natural ligand while being itself devoid of angiogenic activity. As a consequence, angiogenic activity of VEGF is blocked, there is no stimulation of new blood vessels formation and tumor growth is inhibited. In particular, the effector peptide of the above group is the peptide that inhibits the VEGF signal pathway and specifically the 7-amino acid fragment of human VEGF presented by SEQ. No. 17 in the attached Sequence Listing.

It is believed that the peptide comprising sequence of VEGF heptapeptide incorporated into the fusion protein of the invention will effectively eliminate cancer cells by inhibition of angiogenesis process.

Also within the group of inhibitors of receptors for growth factors, the effector peptide of domain (b) may be a fragment of Platelet-Derived Growth Factor PDGF, which binds the PDGF receptor competitively to the natural ligand while being itself devoid of angiogenic activity. As a consequence, angiogenic activity of PDGF is blocked, there is no stimulation of new blood vessels formation and tumor growth is inhibited.

In particular, such an effector peptide is a 19-amino acid peptide—a fragment of PDGF ligand, shown by a sequence of SEQ. No. 22 in the attached Sequence Listing.

It is believed that the peptide comprising sequence of Platelet-Derived Growth Factor PDGF protein fragment incorporated into the fusion protein of the invention will effectively eliminate cancer cells by inhibition of angiogenesis process.

Also within the group of inhibitors of receptors for growth factors, the antiangiogenic effector peptide of domain (b) may be a peptide fragment of Epidermal Growth Factor EGF, which binds the EGF receptor competitively to the natural ligand while being itself devoid of angiogenic activity. As a consequence, angiogenic activity of EGF is blocked, there is no stimulation of new blood vessels formation and tumor growth is inhibited. Such blocking peptides Gly Leu Arg Ser Leu Lys Glu and Gly Leu Arg Ser Leu Arg Glu capable to bind to EGF receptor without activation of intracellular kinase and to block EGR activity are known for example from EP0641358. In particular, such an effector peptide—a fragment of EGF ligand, is shown by a sequence of SEQ. No. 23 in the attached Sequence Listing.

It is believed that the peptide comprising sequence of Epidermal Growth Factor EGF incorporated into the fusion protein of the invention will effectively eliminate cancer cells by inhibition of angiogenesis process.

Within the group of tumstatin and its fragments the effector peptide of domain (b) may be a 25-amino acid fragment of tumstatin protein (fragment I), shown by the sequence of SEQ. No. 18 in the attached Sequence Listing. The effector peptide of the above presented group is also another 18-amino acids fragment of tumstatin protein (fragment II), shown by a sequence of SEQ. No. 19 in the attached Sequence Listing. The antiangiogenic effector peptide of domain (b) may be also a combination of tumstatin peptide fragments, in particular fragment I and fragment II located next to each other in any order. In one embodiment, the domain (b) is a combination of fragment I/fragment II (SEQ. No 18/SEQ. No. 19) or a combination of fragment II/fragment I (SEQ. No 19/SEQ. No. 18).

It is believed that the peptide comprising sequence of tumstatin protein fragment I and/or II incorporated into the fusion protein of the invention will effectively eliminate cancer cells by inhibition of angiogenesis process.

The group of inhibitors of the aminopeptidase N/CD13, which bind with enzyme aminopeptidase N/CD13 to inhibit its activity will include short peptides containing motifs NGR or RGD.

Peptides including motives NGR that bind efficiently to aminopeptidase N are described for example by Arap et al., Science, 279:377-380, 1998. On the extracellular domain of aminopeptidase N a fragment exhibiting affinity to RGD motif is also present. Both motifs (RGD and NGR) bind as antagonists with factors involved in the process of neovascularization. Therefore, it is likely that RGD motif resembling NGR motif will bind with aminopeptidase N and consequently act as its inhibitor (Friedlander et al. *Definition of two angiogenic pathways by distinct av integrins. Science* (Washington D.C.), 270: 1500-1502, 1995; Pasqualini et al Aminopeptidase N is a receptor for tumor-homing peptides and a target for inhibiting angiogenesis. Cancer Res. 2000 Feb. 1; 60 (3):722-7).

Within the group of inhibitors of the aminopeptidase N/CD13, the antiangiogenic effector peptide of domain (b) may be a 5-amino acid peptide binding to CD13 shown by SEQ. No. 20 in the attached Sequence Listing. Another effector peptide of this group is also 9-amino acids peptide binding to CD13, shown by SEQ. No. 21 in the attached Sequence Listing.

It is believed that the peptide comprising sequence of the protein fragment binding with aminopeptidase N/CD13 incorporated into the fusion protein of the invention will effectively eliminate cancer cells by inhibition of angiogenesis process.

The fusion proteins of the invention may comprise more than one effector peptide domain (b), in particular two or three domains (b). In one embodiment the fusion protein of the present invention contains two similar or different effector domains (b) selected from SEQ. No. 17, SEQ. No. 18, SEQ. No. 19, SEQ. No. 20, SEQ. No. 21, SEQ. No. 22 and SEQ. No. 23, wherein the effector domains (b) are located next to each other. In other embodiment the fusion protein of the present invention contains two similar or different effector domains (b) selected from SEQ. No. 17, SEQ. No. 18, SEQ. No. 19, SEQ. No. 20, SEQ. No. 21, SEQ. No. 22 and SEQ. No. 23, wherein the effector domains (b) are located at the N-terminus and/or C-terminus of domain (a).

In particular embodiment the fusion protein of the present invention comprises three effector domains.

As an example, the fusion protein comprises the peptide derived from VEGF (SEQ. No. 17) located at the N-terminus of domain (a) and at the C-terminus of domain (a) located next to each other fragment I of tumstatin (SEQ. No. 18) and fragment II of tumstatin (SEQ. No. 19).

In specific embodiments of the fusion protein of the invention, the effector peptide is a peptide having antiangiogenic activity selected from the group consisting of SEQ. No. 17 (heptapeptide derived from VEGF), SEQ. No. 18 (a fragment I (aminoacids 74-98) of tumstatin protein), SEQ. No. 19 (a fragment II (aminoacids 197-214) of tumstatin protein), SEQ. No. 20 (a peptide binding to CD13), SEQ. No. 21 (a peptide binding to CD13), SEQ. No. 22 (a fragment of PDGF) and SEQ. No. 23 (a fragment of EGF).

Upon binding to TRAIL receptors present on the surface of cancer cells, the fusion protein will exert a double effect. Domain (a), that is a functional fragment of TRAIL or its homolog with preserved functionality, will exert its known agonistic activity—i.e. binding to death receptors on the cell surface and activation of the extrinsic pathway of apoptosis. After internalization of the fusion protein comprising antiangiogenic peptide, the domain (b) will be able to potentially exert its action intracellularly in parallel to the activity of TRAIL domain. In this way, anti-cancer activity of TRAIL can be potentiated by activation of other elements and mechanisms—such as steric inhibition of binding site of the natural VEGF, PDGF and EGF ligands, inhibition of angiogenesis and neovascularisation, inhibition of activation of phosphatidylinositol 3-kinase, protein kinase B (PKB/Akt) or indirect stimulation of TRAIL overexpression by kinase Akt and NFk pathway.

In one of the embodiments of the invention, domain (a) and domain (b) are linked by at least one domain (c) comprising the sequence of a cleavage site recognized by proteases present in the cell environment, especially in the tumor cell environment. The linkage of the domain (a) with the domain (b) by at least one domain (c) means that between domains (a) and (b) more than one domain (c) may be present, in particular one or two domains (c).

A protease cleavage site can be selected from:
a sequence recognized by metalloprotease MMP, in particular (Pro Leu Gly Leu Ala Gly Glu Pro/PLGLAGEP) designated as SEQ. No. 24, or (Pro Leu Gly Ile Ala Gly Glu/PLGIAGE) designated as SEQ. No. 55, or (Pro Leu Gly Leu Ala Gly GluPro/PLGLAGEP) designated as SEQ. No. 56;
a sequence recognized by urokinase uPA, in particular Arg Val Val Arg (RVVR in one-letter convention) designated as SEQ. No. 25 or a fragment thereof, which with the last amino acid of the sequence to which is attached, forms SEQ. No. 25,
and their combinations.

In one of the embodiments of the invention, the protease cleavage site is a combination of the sequence recognized by metalloprotease MMP and a sequence recognized by urokinase uPA, located next to each other in any order.

In one embodiment, the domain (c) is a combination of MMP/uPA SEQ. No. 24/SEQ. No. 25 or a combination of uPA/MMP SEQ. No. 25/SEQ. No. 24.

In another embodiment, the domain (c) is a combination of MMP/uPA SEQ. No 55/SEQ. No. 25 or a combination of uPA/MMP SEQ. No. 25/SEQ. No. 55.

In another embodiment, the domain (c) is a combination of MMP/uPA SEQ. No 56/SEQ. No. 25 or a combination of uPA/MMP SEQ. No. 25/SEQ. No. 56.

Proteases metalloprotease MMP and urokinase uPA are overexpressed in the tumour environment. The presence of the sequence recognized by the protease enables the cleavage of the domain (a) from the domain (b), i.e. the release of the functional domain (b) and thus its activation.

The presence of the protease cleavage site, by allowing quick release of the effector peptide, increases the chances of transporting the peptide to the place of its action before random degradation of the fusion protein by proteases present in the cell occurs.

Apart from the main functional elements of the fusion protein, the cleavage site domain(s), the fusion proteins of the invention may contain a neutral sequence/sequences of a flexible steric glycine-cysteine-alanine linker (spacer). Such linkers/spacers are well known and described in the literature. Their incorporation into the sequence of the fusion protein is intended to provide the correct folding of proteins produced by the process of its overexpression in the host cells.

In particular, the flexible steric linker may be selected from the group consisting of SEQ. No. 26 and SEQ. No. 27, which are combinations of glycine, cysteine and alanine residues. In another embodiment the flexible steric linker may be selected from the group consisting of SEQ. No. 28, SEQ. No. 29, SEQ. No. 30 and SEQ. No. 54, consisting of glycine and serine residues. Additionally, the flexible steric linker may be any fragment of SEQ. No. 28, SEQ. No. 29 SEQ. No. 30 and SEQ. No. 54, acting as a flexible steric linker, for example a fragment Gly Gly Gly/GGG or a fragment Gly Gly/GG.

In one embodiment, the flexible steric linker may be also selected from single amino acid residue such as single glutamic acid residue, cysteine, serine, proline or glycine residue.

In other embodiment, the flexible steric linker may be any combination of linkers consisting of SEQ. No. 26, SEQ. No. 27 SEQ. No. 28, SEQ. No. 29, SEQ. No. 30, SEQ. No. 54 and single amino acids residues of glutamic acid residue, cysteine, serine, proline or glycine.

Particular embodiments of the fusion protein of the invention are fusion proteins comprising an antiangiogenic peptide selected from the group consisting of the proteins represented by SEQ. No. 1, SEQ. No. 2, SEQ. No. 4, SEQ. No. 5, SEQ. No. 6 and SEQ. No. 46, SEQ. No. 47 and SEQ. No. 48, comprising as an effector peptide a heptapeptide derived from VEGF.

Other specific embodiment of the fusion protein of the invention is fusion protein comprising an antiangiogenic peptide selected from the group consisting of the proteins represented by SEQ. No. 7 and SEQ. No. 8, comprising as an effector peptide sequences binding to CD13.

Other specific embodiment of the fusion protein of the invention is fusion protein comprising an antiangiogenic peptide selected from the group consisting of the proteins represented by SEQ. No. 9, SEQ. No. 10, SEQ. No. 11 and SEQ. No. 49 comprising as an effector peptide a fragment of PDGF.

Other specific embodiment of the fusion protein of the invention is fusion protein comprising an antiangiogenic peptide selected from the group consisting of the proteins represented by No. SEQ. No. 12 and SEQ. No. 13, comprising as an effector peptide tumstatin and II fragments.

Other specific embodiment of the fusion protein of the invention is fusion protein comprising an antiangiogenic peptide selected from the group consisting of the proteins represented by SEQ. No. 14 and SEQ. No. 15, comprising as an effector peptide a fragment of EGF.

Particular embodiments of the fusion protein of the invention are fusion proteins comprising an antiangiogenic peptide selected from the group consisting of the proteins represented SEQ. No. 3, comprising as an effector peptide a heptapeptide derived from VEGF, fragment I of tumstatin peptide and fragment II of tumastin peptide.

A detailed description of the structure of representative fusion proteins mentioned above are shown in FIGS. 1 to 3 and in FIG. 9, and in the Examples presented herein below.

In accordance with the present invention, by the fusion protein it is meant a single protein molecule containing two or more proteins or fragments thereof, covalently linked via peptide bond within their respective peptide chains, without additional chemical linkers.

The fusion protein can also be alternatively described as a protein construct or a chimeric protein. According to the present invention, the terms "construct" or "chimeric protein", if used, should be understood as referring to the fusion protein as defined above.

For a person skilled in the art it will be apparent that the fusion protein thus defined can be synthesized by known methods of chemical synthesis of peptides and proteins.

The fusion protein can be synthesized by methods of chemical peptide synthesis, especially using the techniques of peptide synthesis in solid phase using suitable resins as carriers. Such techniques are conventional and known in the art, and described inter alia in the monographs, such as for example Bodanszky and Bodanszky, The Practice of Peptide Synthesis, 1984, Springer-Verlag, New York, Stewart et al., Solid Phase Peptide Synthesis, 2nd Edition, 1984, Pierce Chemical Company.

The fusion protein can be synthesized by the methods of chemical synthesis of peptides as a continuous protein. Alternatively, the individual fragments (domains) of protein may be synthesized separately and then combined together in one continuous peptide via a peptide bond, by condensation of the amino terminus of one peptide fragment from the carboxyl terminus of the second peptide. Such techniques are conventional and well known.

For verification of the structure of the resulting peptide known methods of the analysis of amino acid composition of peptides may be used, such as high resolution mass spectrometry technique to determine the molecular weight of the peptide. To confirm the peptide sequence protein sequencers can also be used, which sequentially degrade the peptide and identify the sequence of amino acids.

Preferably, however, the fusion protein of the invention is a recombinant protein, generated by methods of gene expression of a polynucleotide sequence encoding the fusion protein in host cells.

A further aspect of the invention is the polynucleotide sequence, particularly DNA sequence encoding a fusion protein as defined above.

Preferably, the polynucleotide sequence, particularly DNA, according to the invention, encoding the fusion protein as defined above, is a sequence optimized for expression in *E. coli*.

Another aspect of the invention is also an expression vector containing the polynucleotide sequence, particularly DNA sequence of the invention as defined above.

Another aspect of the invention is also a host cell comprising an expression vector as defined above.

A preferred host cell for expression of fusion proteins of the invention is an *E. coli* cell.

Methods for generation of recombinant proteins, including fusion proteins, are well known. In brief, this technique consists in generation of polynucleotide molecule, for example DNA molecule encoding the amino acid sequence of the target protein and directing the expression of the target protein in the host. Then, the target protein encoding polynucleotide molecule is incorporated into an appropriate expression vector, which ensures an efficient expression of the polypeptide. Recombinant expression vector is then introduced into host cells for transfection/transformation, and as a result a transformed host cell is produced. This is followed by a culture of transformed cells to overexpress the target protein, purification of obtained proteins, and optionally cutting off by cleavage the tag sequences used for expression or purification of the protein.

Suitable techniques of expression and purification are described, for example in the monograph Goeddel, Gene Expression Technology, Methods in Enzymology 185, Academic Press, San Diego, Calif. (1990), and A. Staron et al., Advances Mikrobiol., 2008, 47, 2, 1983-1995.

Cosmids, plasmids or modified viruses can be used as expression vectors for the introduction and replication of DNA sequences in host cells. Typically plasmids are used as expression vectors. Suitable plasmids are well known and commercially available.

Expression vector of the invention comprises a polynucleotide molecule encoding the fusion protein of the invention and the necessary regulatory sequences for transcription and translation of the coding sequence incorporated into a suitable host cell. Selection of regulatory sequences is dependent on the type of host cells and can be easily carried out by a person skilled in the art. Examples of such regulatory sequences are transcriptional promoter and enhancer or RNA polymerase binding sequence, ribosome binding sequence, containing the transcription initiation signal, inserted before the coding sequence, and transcription terminator sequence, inserted after the coding sequence. Moreover, depending on the host cell and the vector used, other sequences may be introduced into the expression vector, such as the origin of replication, additional DNA restriction sites, enhancers, and sequences allowing induction of transcription.

The expression vector will also comprise a marker gene sequence, which confers defined phenotype to the transformed cell and enables specific selection of transformed cells. Furthermore, the vector may also contain a second marker sequence which allows to distinguish cells transformed with recombinant plasmid containing inserted coding sequence of the target protein from those which have taken up the plasmid without insert. Most often, typical antibiotic resistance markers are used, however, any other reporter genes known in the field may be used, whose presence in a cell (in vivo) can be easily determined using autoradiography techniques, spectrophotometry or bio- and chemi-luminescence. For example, depending on the host cell, reporter genes such as β-galactosidase, β-glucuronidase, luciferase, chloramphenicol acetyltransferase or green fluorescent protein may be used.

Furthermore, the expression vector may contain signal sequence, transporting proteins to the appropriate cellular compartment, e.g. periplasma, where folding is facilitated. Additionally a sequence encoding a label/tag, such as HisTag attached to the N-terminus or GST attached to the C-terminus, may be present, which facilitates subsequent purification of the protein produced using the principle of affinity, via affinity chromatography on a nickel column. Additional sequences that protect the protein against proteolytic degradation in the host cells, as well as sequences that increase its solubility may also be present.

Auxiliary element attached to the sequence of the target protein may block its activity, or be detrimental for another reason, such as for example due to toxicity. Such element must be removed, which may be accomplished by enzymatic or chemical cleavage. In particular, a six-histidine tag HisTag or other markers of this type attached to allow protein purification by affinity chromatography should be removed, because of its described effect on the liver toxicity of soluble TRAIL protein. Heterologous expression systems based on various well-known host cells may be used, including prokaryotic cells: bacterial, such as *Escherichia coli* or *Bacillus subtilis*, yeasts such as *Saccharomyces cervisiae* or *Pichia pastoris*, and eukaryotic cell lines (insect, mammalian, plant).

Preferably, due to the ease of culturing and genetic manipulation, and a large amount of obtained product, the *E. coli* expression system is used. Accordingly, the polynucleotide sequence containing the target sequence encoding the fusion protein of the invention will be optimized for expression in *E. coli*, i.e. it will contain in the coding sequence codons optimal for expression in *E. coli*, selected from the possible sequence variants known in the state of art. Furthermore, the expression vector will contain the above described elements suitable for *E. coli* attached to the coding sequence.

Accordingly, in a preferred embodiment of the invention a polynucleotide sequence comprising a sequence encoding a fusion protein of the invention, optimized for expression in *E. coli* is selected from the group of polynucleotide sequences consisting of:

SEQ. No. 31; SEQ. No. 32; SEQ. No. 33, SEQ. No. 34; SEQ. No. 35; SEQ. No. 36; SEQ. No. 37; SEQ. No. 38; SEQ. No. 39; SEQ. No. 40; SEQ. No. 41, SEQ. No. 42; SEQ. No. 43 SEQ. No. 44; SEQ. No. 45, SEQ. No. 50, SEQ. No. 51, SEQ. No. 52; SEQ. No. 53; which encode a fusion protein having an amino acid sequence corresponding to amino acid sequences selected from the group consisting of amino acid sequences, respectively:

SEQ. No. 1; SEQ. No. 2; SEQ. No. 3; SEQ. No. 4; SEQ. No. 5; SEQ. No. 6; SEQ. No. 7; SEQ. No. 8; SEQ. No. 9; SEQ. No. 10; SEQ. No. 11, SEQ. No. 12, SEQ. No. 13; SEQ. No. 14 SEQ. No. 15, SEQ. No. 46; SEQ. No. 47; SEQ. No. 48; and SEQ. No. 49.

In a preferred embodiment, the invention provides also an expression vector suitable for transformation of *E. coli*, comprising the polynucleotide sequence selected from the group of polynucleotide sequences SEQ. No. 31 to SEQ. No. 45 and SEQ. No 50 to SEQ. No. 53 indicated above, as well as *E. coli* cell transformed with such an expression vector.

Transformation, i.e. introduction of a DNA sequence into bacterial host cells, particularly *E. coli*, is usually performed on the competent cells, prepared to take up the DNA for example by treatment with calcium ions at low temperature (4° C.), and then subjecting to the heat-shock (at 37-42° C.) or by electroporation. Such techniques are well known and are usually determined by the manufacturer of the expression system or are described in the literature and manuals for laboratory work, such as Maniatis et al., Molecular Cloning. Cold Spring Harbor, N.Y., 1982).

The procedure of overexpression of fusion proteins of the invention in *E. coli* expression system will be further described below.

The invention also provides a pharmaceutical composition containing the fusion protein of the invention as defined above as an active ingredient and a suitable pharmaceutically acceptable carrier, diluent and conventional auxiliary components. The pharmaceutical composition will contain an effective amount of the fusion protein of the invention and pharmaceutically acceptable auxiliary components dissolved or dispersed in a carrier or diluent, and preferably will be in the form of a pharmaceutical composition formulated in a unit dosage form or formulation containing a plurality of doses. Pharmaceutical forms and methods of their formulation as well as other components, carriers and diluents are known to the skilled person and described in the literature. For example, they are described in the monograph Remington's Pharmaceutical Sciences, ed. 20, 2000, Mack Publishing Company, Easton, USA.

The terms "pharmaceutically acceptable carrier, diluent, and auxiliary ingredient" comprise any solvents, dispersion media, surfactants, antioxidants, stabilizers, preservatives (e.g. antibacterial agents, antifungal agents), isotoning agents, known in the art. The pharmaceutical composition of the invention may contain various types of carriers, diluents and excipients, depending on the chosen route of administration and desired dosage form, such as liquid, solid and aerosol forms for oral, parenteral, inhaled, topical, and whether that selected form must be sterile for administration route such as by injection. The preferred route of administration of the pharmaceutical composition according to the invention is parenteral, including injection routes such as intravenous, intramuscular, subcutaneous, intraperitoneal, intratumourous, or by single or continuous intravenous infusions.

In one embodiment, the pharmaceutical composition of the invention may be administered by injection directly to the tumour. In another embodiment, the pharmaceutical composition of the invention may be administered intravenously. In yet another embodiment, the pharmaceutical composition of the invention can be administered subcutaneously or intraperitoneally. A pharmaceutical composition for parenteral administration may be a solution or dispersion in a pharmaceutically acceptable aqueous or non-aqueous medium, buffered to an appropriate pH and isoosmotic with body fluids, if necessary, and may also contain antioxidants, buffers, bacteriostatic agents and soluble substances, which make the composition compatible with the tissues or blood of recipient. Other components, which may included in the composition, are for example water, alcohols such as ethanol, polyols such as glycerol, propylene glycol, liquid polyethylene glycol, lipids such as triglycerides, vegetable oils, liposomes. Proper fluidity and the particles size of the substance may be provided by coating substances, such as lecithin, and surfactants, such as hydroxypropyl celulose polysorbates, and the like.

Suitable isotoning agents for liquid parenteral compositions are, for example, sugars such as glucose, and sodium chloride, and combinations thereof.

Alternatively, the pharmaceutical composition for administration by injection or infusion may be in a powder form, such as a lyophilized powder for reconstitution immediately prior to use in a suitable carrier such as, for example, sterile pyrogen-free water.

The pharmaceutical composition of the invention for parenteral administration may also have the form of nasal administration, including solutions, sprays or aerosols. Preferably, the form for intranasal administration will be an aqueous solution and will be isotonic or buffered to maintain the pH from about 5.5 to about 6.5, so as to maintain a character similar to nasal secretions. Moreover, it will contain preservatives or stabilizers, such as in the well-known intranasal preparations.

The composition may contain various antioxidants which delay oxidation of one or more components. Furthermore, in order to prevent the action of microorganisms, the composition may contain various antibacterial and anti fungal agents, including, for example, and not limited to, parabens, chlorobutanol, himerosal, sorbic acid, and similar known substances of this type. In general, the pharmaceutical composition of the invention can include, for example at least about 0.01 wt % of active ingredient. More particularly, the composition may contain the active ingredient in the amount from 1% to 75% by weight of the composition unit, or for example from 25% to 60% by weight, but not limited to the indicated values. The actual amount of the dose of the composition according to the present invention administered to patients, including man, will be determined by physical and physiological factors, such as body weight, severity of the condition, type of disease being treated, previous or concomitant therapeutic interventions, the patient and the route of administration. A suitable unit dose, the total dose and the concentration of active ingredient in the composition is to be determined by the treating physician.

The composition may for example be administered at a dose of about 1 microgram/kg of body weight to about 1000 mg/kg of body weight of the patient, for example in the range of 5 mg/kg of body weight to 100 mg/kg of body weight or in the range of 5 mg/kg of body weight to 500 mg/kg of body weight. The fusion protein and the compositions containing it exhibit anticancer or antitumor and can be used for the treatment of cancer diseases. The invention also provides the use of the fusion protein of the invention as defined above for treating cancer diseases in mammals, including humans. The invention also provides a method of treating cancer diseases in mammals, including humans, comprising administering to a subject in need of such treatment an anticancer effective amount of the fusion protein of the invention as defined above, optionally in the form of appropriate pharmaceutical composition.

The fusion protein of the invention can be used for the treatment of hematologic malignancies, such as leukaemia, granulomatosis, myeloma and other hematologic malignancies. The fusion protein can also be used for the treatment of solid tumours, such as breast cancer, lung cancer, including non-small cell lung cancer, colon cancer, pancreatic cancer, ovarian cancer, bladder cancer, prostate cancer, kidney cancer, brain cancer, and the like. Appropriate route of administration of the fusion protein in the treatment of cancer will be in particular parenteral route, which consists in administering the fusion protein of the invention in the form of injections or infusions, in the composition and form appropriate for this administration route. The invention will be described in more detail in the following general procedures and examples of specific fusion proteins.

General Procedure for Overexpression of the Fusion Protein
Preparation of a Plasmid Amino acid sequence of the target fusion protein was used as a template to generate a DNA sequence encoding it, comprising codons optimized for expression in *Escherichia coli*. Such a procedure allows to increase the efficiency of a further step of target protein synthesis in *Escherichia coli*. Resulting nucleotide sequence was then automatically synthesized. Additionally, the cleavage sites of restriction enzymes NdeI (at the 5'-end of leading strand) and XhoI (at the 3'-end of leading strand) were added to the resulting gene encoding the target protein. These were used to clone the gene into the vector pET28a (Novagen). They may be also used for cloning the gene encoding the protein to other vectors. Target protein expressed from this construct can be optionally equipped at the N-terminus with a polyhistidine tag (six histidines), preceded by a site recognized by thrombin, which subsequently served to its purification via affinity chromatography. Some target were expressed without any tag, in particular without histidine tag, and those were subsequently purified on SP Sepharose. The correctness of the resulting construct was confirmed firstly by restriction analysis of isolated plasmids using the enzymes NdeI and XhoI, followed by automatic sequencing of the entire reading frame of the target protein. The primers used for sequencing were complementary to the sequences of T7 promoter (5'-TAATACGACTCACTAT-AGG-3') (SEQ ID NO: 57) and T7 terminator (5'-GCTAGT-TATTGCTCAGCGG-3') (SEQ ID NO: 58) present in the vector. Resulting plasmid was used for overexpression of the target fusion protein in a commercial *E. coli* strain, which was transformed according to the manufacturer's recommendations. Colonies obtained on the selection medium (LB agar, kanamycin 50 μg/ml, 1% glucose) were used for preparing an overnight culture in LB liquid medium supplemented with kanamycin (50 μg/ml) and 1% glucose. After about 15 h of growth in shaking incubator, the cultures were used to inoculate the appropriate culture.

Overexpression and Purification of Fusion Proteins—General Procedure A

LB medium with kanamycin (30 μg/ml) and 100 μM zinc sulfate was inoculated with overnight culture. The culture was incubated at 37° C. until the optical density (OD) at 600 nm reached 0.60-0.80. Then IPTG was added to the final concentration in the range of 0.25-1 mM. After incubation (3.5-20 h) with shaking at 25° C. the culture was centrifuged for 25 min at 6,000 g. Bacterial pellets were resuspended in a buffer containing 50 mM $KH_2PO_4$, 0.5 M NaCl, 10 mM imidazole, pH 7.4. The suspension was sonicated on ice for 8 minutes (40% amplitude, 15-second pulse, 10 s interval). The resulting extract was clarified by centrifugation for 40 minutes at 20000 g, 4° C. Ni-Sepharose (GE Healthcare) resin was pre-treated by equilibration with buffer, which was used for preparation of the bacterial cells extract. The resin was then incubated overnight at 4° C. with the supernatant obtained after centrifugation of the extract. Then it was loaded into chromatography column and washed with 15 to 50 volumes of buffer 50 mM $KH_2PO_4$, 0.5 M NaCl, 20 mM imidazole, pH 7.4. The obtained protein was eluted from the column using imidazole gradient in 50 mM $KH_2PO_4$ buffer with 0.5 M NaCl, pH 7.4. Obtained fractions were analyzed by SDS-PAGE. Appropriate fractions were combined and dialyzed overnight at 4'C against 50 mM Tris buffer, pH 7.2, 150 mM NaCl, 500 mM L-arginine, 0.1 mM $ZnSO_4$, 0.01% Tween 20, and at the same time Histag, if present, was cleaved with thrombin (1:50). After the cleavage, thrombin was separated from the target fusion protein expressed with Histag by purification using Benzamidine Sepharose™ resin. Purification of target fusion proteins expressed without Histag was performed on SP Sepharose. The purity of the product was analyzed by SDS-PAGE electrophoresis (Maniatis et al, Molecular Cloning. Cold Spring Harbor, N.Y., 1982).

Overexpression and Purification of Fusion Proteins—General Procedure B

LB medium with kanamycin (30 μg/ml) and 100 μM zinc sulfate was inoculated with overnight culture. Cultures were incubated at 37° C. until optical density (OD) at 600 nm reached 0.60-0.80. Then IPTG was added to the final concentration in the range 0.5-1 mM. After 20 h incubation with shaking at 25° C. the culture was centrifuged for 25 min at 6000 g. Bacterial cells after overexpression were disrupted in a French Press in a buffer containing 50 mM $KH_2PO_4$, 0.5 M NaCl, 10 mM imidazole, 5 mM beta-mercaptoethanol, 0.5 mM PMSF (phenylmethylsulphonyl fluoride), pH 7.8. Resulting extract was clarified by centrifugation for 50 minutes at 8000 g. The Ni-Sepharose resin was incubated overnight with the obtained supernatant. Then the resin with bound protein was packed into the chromatography column. To wash-out the fractions containing non-binding proteins, the column was washed with 15 to 50 volumes of buffer 50 mM $KH_2PO_4$, 0.5 M NaCl, 10 mM imidazole, 5 mM beta-mercaptoethanol, 0.5 mM PMSF (phenylmethylsulphonyl fluoride), pH 7.8. Then, to wash-out the majority of proteins binding specifically with the bed, the column was washed with a buffer containing 50 mM KH2PO4, 0.5 M NaCl, 500 mM imidazole, 10% glycerol, 0.5 mM PMSF, pH 7.5. Obtained fractions were analyzed by SDS-PAGE (Maniatis et al, Molecular Cloning. Cold Spring Harbor, N.Y., 1982). The fractions containing the target protein were combined and, if the protein was expressed with histidine tag, cleaved with thrombin (1 U per 4 mg of protein, 8 h at 16° C.) to remove polyhistidine tag. Then the fractions were dialyzed against formulation buffer (500 mM L-arginine, 50 mM Tris, 2.5 mM ZnSO$_4$, pH 7.4).

Example 1

The Fusion Protein of SEQ. No. 1

The protein of SEQ. No. 1 is a fusion protein having the length of 173 amino acids and the mass of 19.8 kDa, in which at the N-terminus of the sequence TRAIL 121-281 heptapeptide derived from VEGF (SEQ. No. 17) is attached as an effector peptide. Between the effector peptide and the sequence of TRAIL the flexible glycine steric linker (SEQ. No. 28) is incorporated.

Structure of the fusion protein is shown schematically in FIG. 1, and its amino acid sequence and the DNA encoding sequence comprising codons optimized for expression in *E. coli* are, respectively, SEQ. No. 1 and SEQ. No. 31, as shown in the attached Sequence Listing.

The amino acid sequence SEQ. No. 1 of the structure described above was used as a template to generate its coding DNA sequence DNA SEQ. No. 31. A plasmid containing the coding sequence of DNA in two versions, one allowing to express His tag and a site recognized by thrombin and the second without any tag, was generated and overexpression of the fusion proteins was carried out in accordance with the general procedures described above. Overexpression was performed according to the general procedure A, using *E. coli* BL21 (DE3) and Tuner(DE3)pLysS strains, both from Novagen. The proteins were separated by electrophoresis in accordance with the general procedure described above.

Example 2

The Fusion Protein of SEQ. No. 2

The fusion protein of SEQ. No. 2 is a fusion protein having the length of 199 amino acids and the mass of 22.8 kDa, in which at the N-terminus of the sequence TRAIL 95-281 heptapeptide derived from VEGF (SEQ. No. 17) is attached as an effector peptide. Between the effector peptide and the sequence of TRAIL the flexible glycine steric linker (SEQ. No. 28) is incorporated.

Structure of the fusion protein is shown schematically in FIG. 1, and its amino acid sequence and the DNA encoding sequence comprising codons optimized for expression in *E. coli* are, respectively, SEQ. No. 2 and SEQ. No. 32, as shown in the attached Sequence Listing.

The amino acid sequence SEQ. No. 2 was used as a template to generate its coding DNA sequence DNA SEQ. No. 32. A plasmid containing the coding sequence of DNA, with a sequence allowing to express His tag and a site recognized by thrombin, was generated and overexpression of the fusion protein was carried out in accordance with the general procedures described above. Overexpression was performed according to the general procedure A, using *E. coli* BL21 (DE3) strain from Novagen. The protein was separated by electrophoresis in accordance with the general procedure described above.

Example 3

The Fusion Protein of SEQ. No. 3

The fusion protein of SEQ. No. 3 is a fusion protein having the length of 230 amino acids and the mass of 26.3 kDa, in which at the N-terminus of the sequence TRAIL 121-281 heptapeptide derived from VEGF (SEQ. No. 17), and at C-terminus of the sequence TRAIL 121-281 fragments I and II of tumstatin (SEQ. No. 18 and SEQ. No. 19, respectively) are attached as an effector peptide. Between the effector peptide attached at the N-terminus of the sequence TRAIL and the sequence of TRAIL there is incorporated the glycine flexible steric linker (SEQ. No. 28). Between the effector peptide attached at the C-terminus of the sequence TRAIL and the sequence of TRAIL there is incorporated steric linker consisting of 3 glycine residues Gly Gly Gly, and sequences of cleavage sites recognized by metalloprotease MMP (SEQ. No. 24) and urokinase uPA (SEQ. No. 25), due to which the effector peptide will undergo cleavage in the tumour environment.

Structure of the fusion protein is shown schematically in FIG. 1, and its amino acid sequence and the DNA encoding sequence comprising codons optimized for expression in *E. coli* are, respectively, SEQ. No. 3 and SEQ. No. 33, as shown in the attached Sequence Listing.

The amino acid sequence SEQ. No. 3 was used as a template to generate its coding DNA sequence SEQ. No. 33. A plasmid containing the coding sequence of DNA, with a sequence allowing to express His tag and a site recognized by thrombin, was generated and overexpression of the fusion protein was carried out in accordance with the general procedures described above. Overexpression was performed according to the general procedure B, using *E. coli* BL21 (DE3) strain from Novagen. The protein was separated by electrophoresis in accordance with the general procedure described above.

Example 4

The Fusion Protein of SEQ. No. 4

The protein of SEQ. No. 4 is a fusion protein having the length of 187 amino acids and the mass of 21.4 kDa, in which at the N-terminus of the sequence TRAIL 121-281 two sequences of heptapeptide derived from VEGF (SEQ. No. 17) are attached as an effector peptide. Between the two sequences of effector peptide there is incorporated sequence of cleavage site recognized by metalloprotease MMP (SEQ. No. 24), due to which the effector peptide will undergo cleavage in the tumour environment. Between the sequence of MMP cleavage site and the sequence of effector protein there is incorporated a single glutamic acid residue E. Between the effector peptide (SEQ. 17) and the sequence of TRAIL there is incorporated flexible steric glycine linker (SEQ. No. 28).

Structure of the fusion protein is shown schematically in FIG. 1, and its amino acid sequence and the DNA encoding sequence comprising codons optimized for expression in *E. coli* are, respectively, SEQ. No. 4 and SEQ. No. 34, as shown in the attached Sequence Listing.

The amino acid sequence SEQ. No. 4 was used as a template to generate its coding DNA sequence DNA SEQ. No. 34. A plasmid containing the coding sequence of DNA in two versions, one allowing to express His tag and a site recognized by thrombin and the second without any tag, was generated and overexpression of the fusion proteins was carried out in accordance with the general procedures described above. Overexpression was performed according to the general procedure B, using *E. coli* BL21DE3pLysSRIL strain from Stratagene and Tuner (DE3) from Novagen. The proteins were separated by electrophoresis in accordance with the general procedure described above.

Example 5

The Fusion Protein of SEQ. No. 5

The protein of SEQ. No. 5 is a fusion protein having the length of 187 amino acids and the mass of 21.8 kDa, in which at the N-terminus of the sequence TRAIL 121-281 two sequences of heptapeptide derived from VEGF (SEQ. No. 17) are attached as an effector peptide. Between the two sequences of effector peptides the protein contains sequences of cleavage sites recognized by urokinase uPA (SEQ. No. 25) and metalloprotease MMP (SEQ. No. 24), due to which the effector peptide will undergo cleavage in the tumour environment. Between the sequence of MMP cleavage site and the sequence of effector protein there is incorporated single glutamic acid residue E. Additionally at the N-terminus of TRAIL two glycine residues are attached.

Structure of the fusion protein is shown schematically in FIG. 1, and its amino acid sequence and the DNA encoding sequence comprising codons optimized for expression in *E. coli* are, respectively, SEQ. No. 5 and SEQ. No. 35, as shown in the attached Sequence Listing.

The amino acid sequence SEQ. No. 5 was used as a template to generate its coding DNA sequence DNA SEQ. No. 35. A plasmid containing the coding sequence of DNA in two versions, one allowing to express His tag and a site recognized by thrombin and the second without any tag, was generated and overexpression of the fusion proteins was carried out in accordance with the general procedures described above. Overexpression was performed according to the general procedure A, using *E. coli* Tuner (DE3) strain from Novagen. The proteins were separated by electrophoresis in accordance with the general procedure described above.

Example 6

The Fusion Protein of SEQ. No. 6

The protein of SEQ. No. 6 is a fusion protein having the length of 222 amino acids and the mass of 25.3 kDa, in which at the N-terminus of the sequence TRAIL 95-281 two sequences of heptapeptide derived from VEGF (SEQ. No. 17) are attached as an effector peptide. Between the two sequences of effector peptide the protein contains sequences of cleavage sites recognized by uPA (SEQ. No. 25) and metalloprotease MMP (SEQ. No. 55) due to which the effector peptide will undergo cleavage in the tumour environment. Between the effector peptide (SEQ. 17) and the sequence of TRAIL there is incorporated the cysteine flexible steric linker (SEQ. No. 26).

Structure of the fusion protein is shown schematically in FIG. 1, and its amino acid sequence and the DNA encoding sequence comprising codons optimized for expression in *E. coli* are, respectively, SEQ. No. 6 and SEQ. No. 36, as shown in the attached Sequence Listing.

The amino acid sequence SEQ. No. 6 was used as a template to generate its coding DNA sequence DNA SEQ. No. 36 A plasmid containing the coding sequence of DNA, without a sequence allowing to express His tag and a site recognized by thrombin, was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

Example 7

The Fusion Protein of SEQ. No. 7

The protein of SEQ. No. 7 is a fusion protein having the length of 168 amino acids and the mass of 19.4 kDa, in which at the N-terminus of the sequence TRAIL 119-281 a sequence being a ligand of CD13 (SEQ. No. 20) is attached as an effector peptide.

Figure 2:
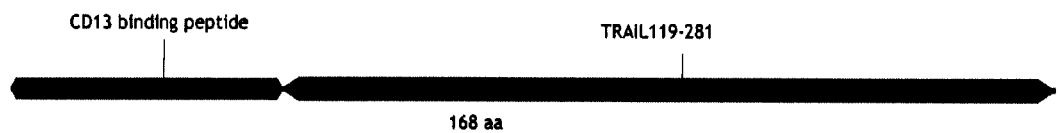
FIG. 2 presents a schematic structure of fusion proteins of the invention according to Ex. 7, Ex. 8, Ex. 9, Ex. 10 and Ex. 11.
Figure 2:
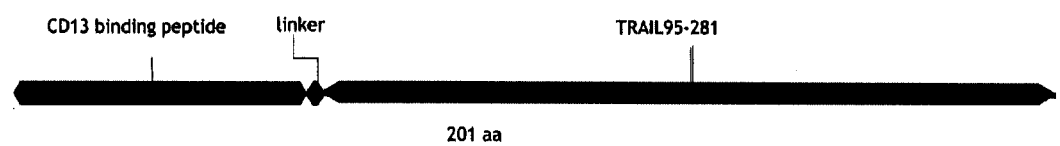
Figure 2:
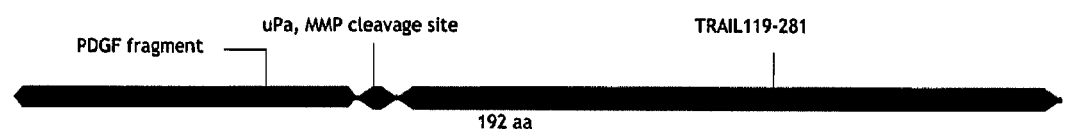
Figure 2:
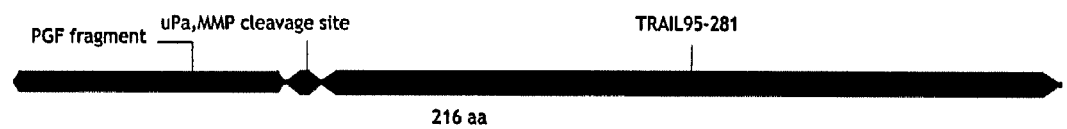
Figure 2:
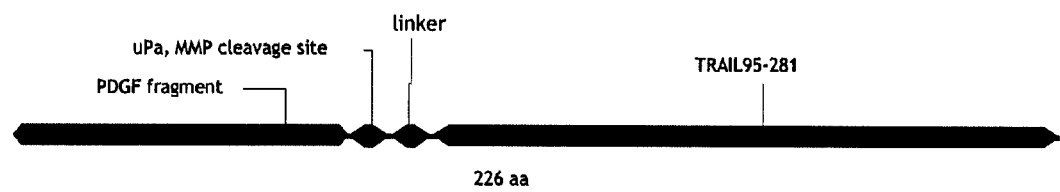

Structure of the fusion protein is shown schematically in FIG. 2, and its amino acid sequence and the DNA encoding sequence comprising codons optimized for expression in *E. coli* are, respectively, SEQ. No. 7 and SEQ. No. 37, as shown in the attached Sequence Listing.

The amino acid sequence SEQ. No. 7 was used as a template to generate its coding DNA sequence DNA SEQ. No. 37. A plasmid containing the coding sequence of DNA in two versions, one allowing to express His tag and a site recognized by thrombin and the second without any tag, was generated and overexpression of the fusion proteins was carried out in accordance with the general procedures described above. Overexpression was performed according to the general procedure A, using *E. coli* Tuner (DE3) strain from Novagen. The proteins were separated by electrophoresis in accordance with the general procedure described above.

Example 8

The Fusion Protein of SEQ. No. 8

The protein of SEQ. No. 8 is a fusion protein having the length of 201 amino acids and the mass of 23.2 kDa, in which at the N-terminus of the sequence TRAIL 95—a sequence being a ligand of CD13 (SEQ. No. 21) is attached as an effector peptide. Between the sequence of TRAIL and the sequence of effector peptide the protein contains a sequence of flexible glycine-serine linker (SEQ. No. 30).

Structure of the fusion protein is shown schematically in FIG. 2, and its amino acid sequence and the DNA encoding sequence comprising codons optimized for expression in *E. coli* are, respectively, SEQ. No. 8 and SEQ. No. 38, as shown in the attached Sequence Listing.

The amino acid sequence SEQ. No. 8 was used as a template to generate its coding DNA sequence DNA SEQ. No. 38. A plasmid containing the coding sequence of DNA, with a sequence allowing to express His tag and a site recognized by thrombin, was generated and overexpression of the fusion protein was carried out in accordance with the general procedures described above. Overexpression was performed according to the general procedure A, using *E. coli* Tuner (DE3) strain from Novagen. The protein was separated by electrophoresis in accordance with the general procedure described above.

Example 9

The Fusion Protein of SEQ. No. 9

The protein of SEQ. No. 9 is a fusion protein having the length of 192 amino acids and the mass of 22.1 kDa, in which at the N-terminus of the sequence TRAIL 119-281 a sequence of PDGF fragment (SEQ. No. 22) is attached as an effector peptide. Between the effector peptide and the sequence of TRAIL the protein contains sequences of cleavage sites recognized by urokinase uPA (SEQ. No. 25) and metalloprotease MMP (SEQ. No. 24). due to which the effector peptide will undergo cleavage in the tumour environment.

Structure of the fusion protein is shown schematically in FIG. 2, and its amino acid sequence and the DNA encoding sequence comprising codons optimized for expression in *E. coli* are, respectively, SEQ. No. 9 and SEQ. No. 39, as shown in the attached Sequence Listing.

The amino acid sequence SEQ. No. 9 was used as a template to generate its coding DNA sequence DNA SEQ. No. 39. A plasmid containing the coding sequence of DNA in two versions, one allowing to express His tag and a site recognized by thrombin and the second without any tag, was generated and overexpression of the fusion proteins was carried out in accordance with the general procedures described above. Overexpression was performed according to the general procedure A, using *E. coli* Rosetta (DE3) strain from Novagen. The proteins were separated by electrophoresis in accordance with the general procedure described above.

Example 10

The Fusion Protein of SEQ. No. 10

The protein of SEQ. No. 10 is a fusion protein having the length of 216 amino acids and the mass of 24.9 kDa, in which at the N-terminus of the sequence TRAIL 95-281 a fragment of PDGF (SEQ. No. 22) is attached as an effector peptide. Between the sequence of effector peptide and the TRAIL domain the protein contains sequences of cleavage sites recognized by uPA (SEQ. No. 25) and metalloprotease MMP (SEQ. No. 24), due to which the effector peptide will undergo cleavage in the tumour environment.

Structure of the fusion protein is shown schematically in FIG. 2, and its amino acid sequence and the DNA encoding sequence comprising codons optimized for expression in *E. coli* are, respectively, SEQ. No. 10 and SEQ. No. 40, as shown in the attached Sequence Listing.

The amino acid sequence SEQ. No. 10 was used as a template to generate its coding DNA sequence DNA SEQ. No. 40. A plasmid containing the coding sequence of DNA, with a sequence allowing to express His tag and a site recognized by thrombin, was generated and overexpression of the fusion protein was carried out in accordance with the general procedures described above. Overexpression was performed according to the general procedure A, using *E. coli* BL21 (DE3) and Tuner(DE3)pLysS strains, both from Novagen. The protein was separated by electrophoresis in accordance with the general procedure described above.

Example 11

The Fusion Protein of SEQ. No. 11

The protein of SEQ. No. 11 is a fusion protein having the length of 226 amino acids and the mass of 25.7 kDa, in which at the N-terminus of the sequence TRAIL95-281 a PDGF fragment (SEQ. No. 22) is attached as an effector peptide.

Between the effector peptide and the sequence of TRAIL the protein contains sequences of cleavage sites recognized by urokinase uPA (SEQ. No. 25) and metalloprotease MMP (SEQ. No. 24). due to which the effector peptide will undergo cleavage in the tumour environment. Between the TRAIL sequence and the sequence of cleavage site recognized by metalloprotease MMP the protein contains also flexible glycine-cysteine-alanine linker (SEQ. No. 27).

Structure of the fusion protein is shown schematically in FIG. 2, and its amino acid sequence and the DNA encoding sequence comprising codons optimized for expression in *E. coli* are, respectively, SEQ. No. 11 and SEQ. No. 41, as shown in the attached Sequence Listing.

The amino acid sequence SEQ. No. 11 was used as a template to generate its coding DNA sequence DNA SEQ. No. 41. A plasmid containing the coding sequence of DNA, without a sequence allowing to express His tag and a site recognized by thrombin, was generated and overexpression of the fusion protein was carried out in accordance with the general procedures described above. Overexpression was performed according to the general procedure A, using *E. coli* BL21 (DE3) and Tuner(DE3)pLysS strains, both from Novagen. The protein was separated by electrophoresis in accordance with the general procedure described above.

Example 12

The Fusion Protein of SEQ. No. 12

The protein of SEQ. No. 12 is a fusion protein having the length of 217 amino acids and the mass of 25 kDa, in which at the N-terminus of the sequence TRAIL 121-281 fragments I and II of tumstatine (SEQ. No. 18 and SEQ. No. 19) are attached as an effector peptide. Between the effector peptide and the sequence of TRAIL the protein contains sequences of cleavage sites recognized by urokinase uPA (SEQ. No. 25) and metalloprotease MMP (SEQ. No. 24), due to which the effector peptide will undergo cleavage in the tumour environment. Between the sequence of TRAIL and the sequence of cleavage site recognized by metalloprotease MMP the protein contains also a flexible linker consisting of 3 glycine residues Gly Gly Gly.

Figure 3:
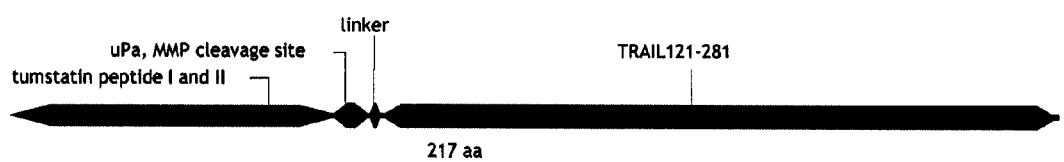
FIG. 3 presents a schematic structure of fusion proteins of the invention according to Ex. 12, Ex. 13, Ex. 14 and Ex. 15.
Figure 3:
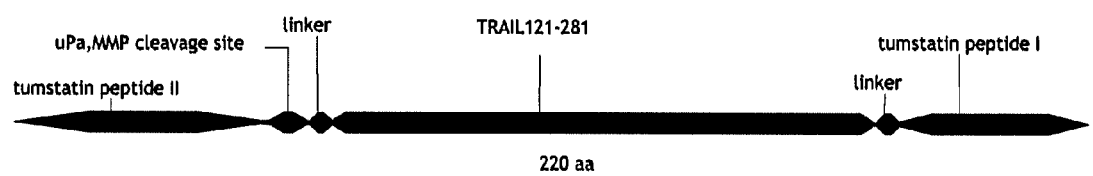
Figure 3:
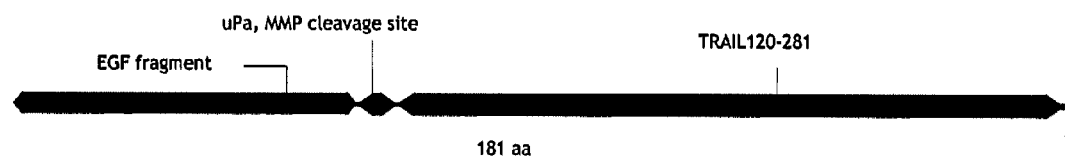
Figure 3:
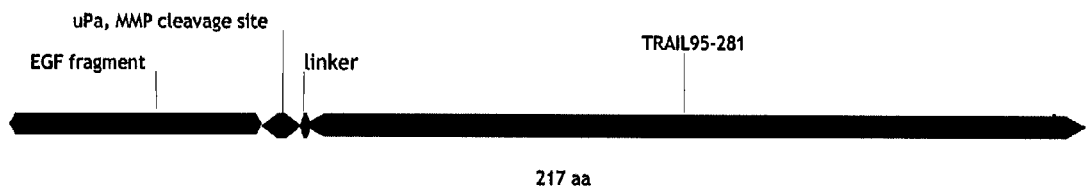
Figure 4A:
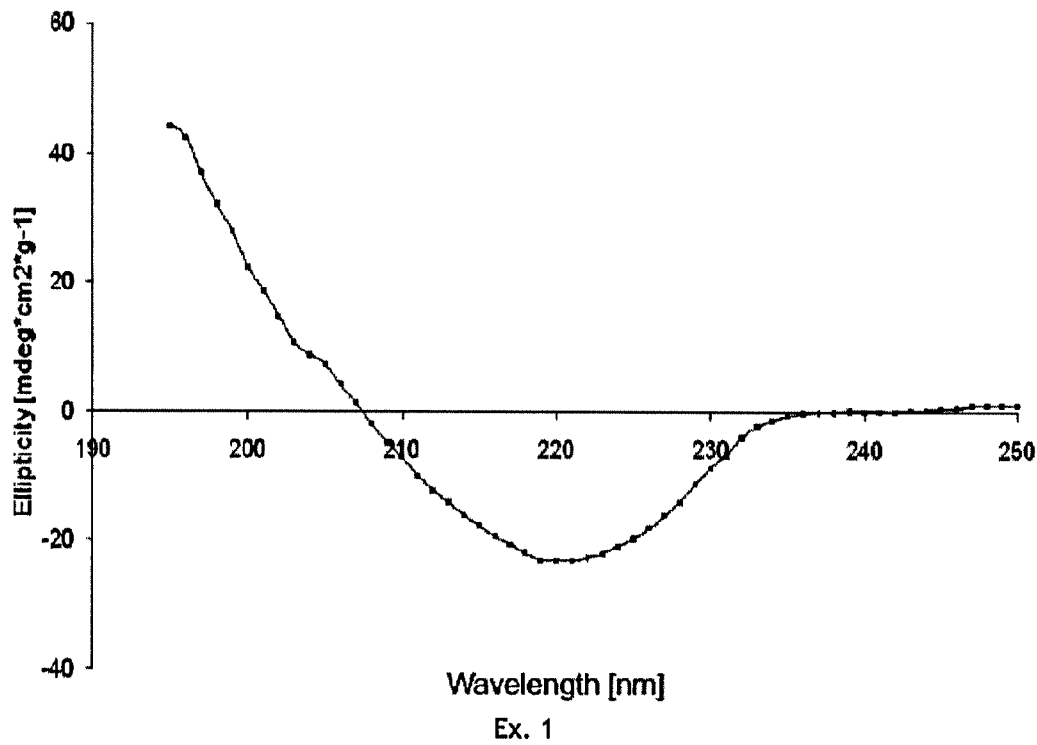
FIGS. 4A-C show circular dichroism spectra for the rhTRAIL95-281 and fusion proteins of Ex. 1, Ex. 4, Ex. 5, Ex. 9 and Ex. 14 expressed in specific ellipticity.
Figure 4A:
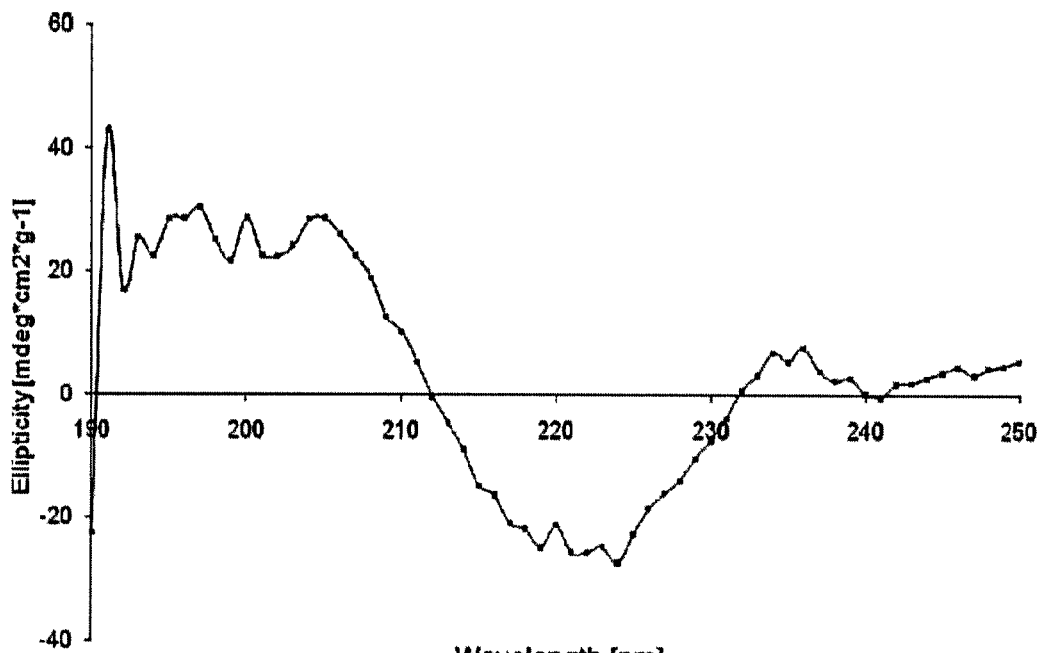
Figure 4B:
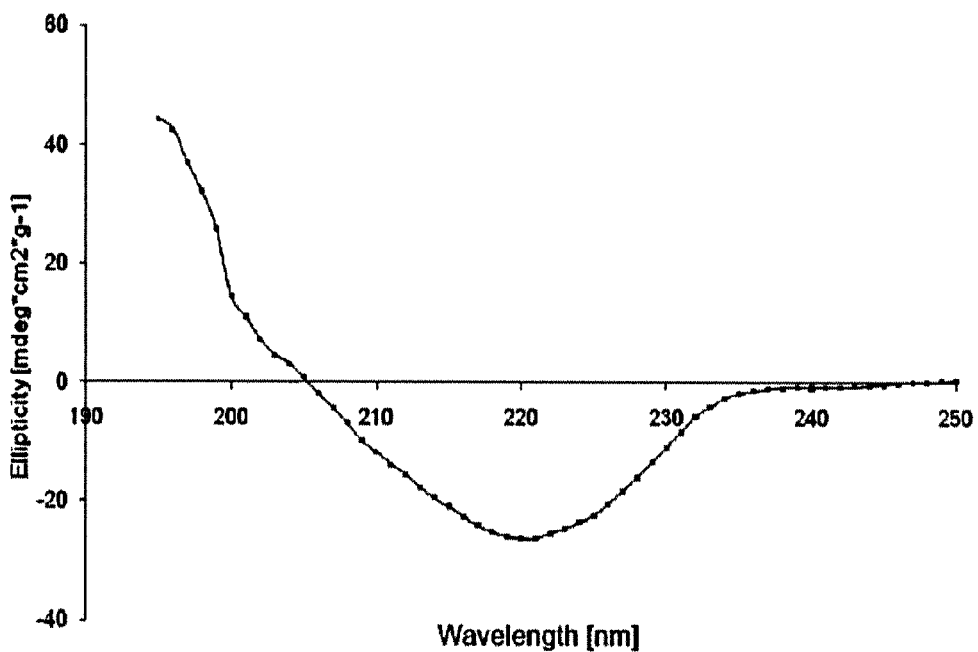
Figure 4B:
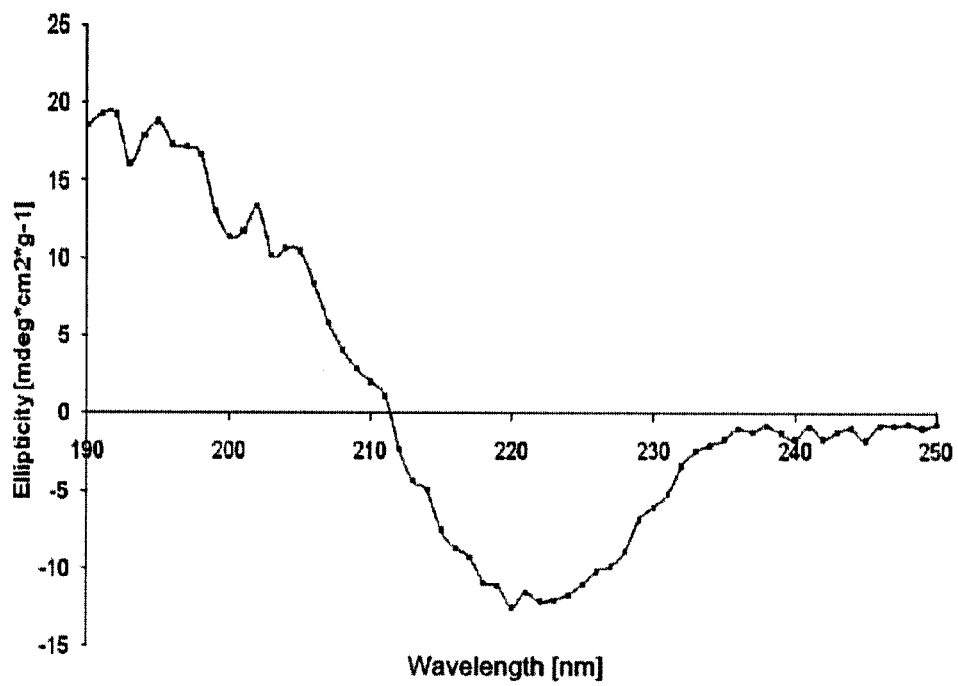
Figure 4C:
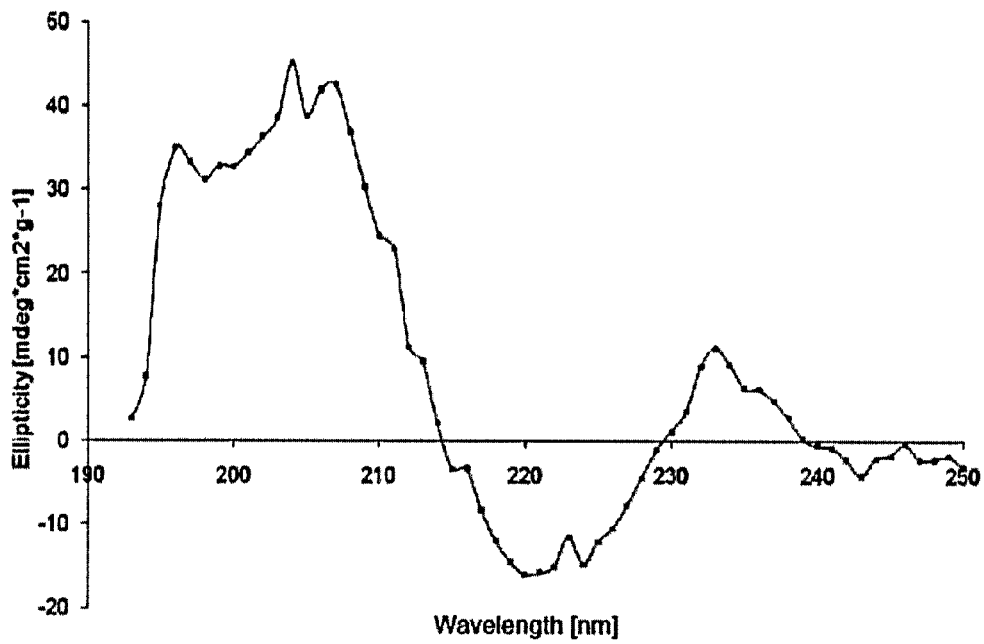
Figure 4C:
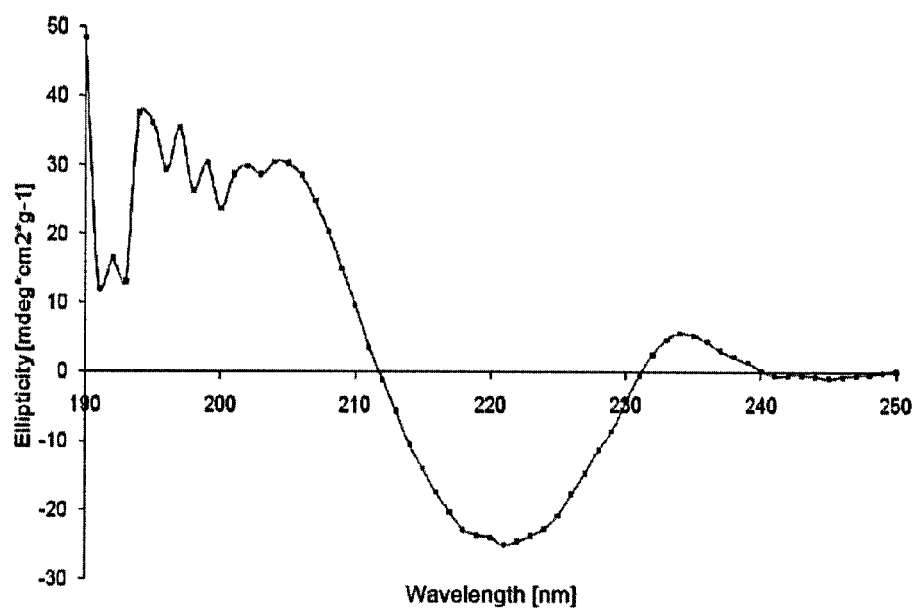

Structure of the fusion protein is shown schematically in FIG. 3, and its amino acid sequence and the DNA encoding sequence comprising codons optimized for expression in *E. coli* are, respectively, SEQ. No. 12 and SEQ. No. 42, as shown in the attached Sequence Listing.

The amino acid sequence SEQ. No. 12 was used as a template to generate its coding DNA sequence DNA SEQ. No. 42. A plasmid containing the coding sequence of DNA, with a sequence allowing to express His tag and a site recognized by thrombin, was generated and overexpression of the fusion protein was carried out in accordance with the general procedures described above. Overexpression was performed according to the general procedure A, using *E. coli* BL21 (DE3) and Tuner(DE3)pLysS strains, both from Novagen. The protein was separated by electrophoresis in accordance with the general procedure described above.

Example 13

The Fusion Protein of SEQ. No. 13

The protein of SEQ. No. 13 is a fusion protein having the length of 220 amino acids and the mass of 25.1 kDa, in which at the N-terminus of the sequence TRAIL 121-281 fragment II of tumstatin (SEQ. No. 19) is attached as an effector peptide, and at the C-terminus of the sequence TRAIL 121-281 fragment I of tumstatin (SEQ. No. 18) is attached as an effector peptide. Between the effector peptide and the sequence of TRAIL the protein contains sequences of cleavage sites recognized by urokinase uPA (SEQ. No. 25) and metalloprotease MMP (SEQ. No. 24), due to which the effector peptide will undergo cleavage in the tumour environment. Between the sequence of cleavage site recognized by metalloprotease MMP and the sequence of TRAIL the protein contains three glycine residues Gly Gly Gly and between the C-terminus of the sequence TRAIL and fragment II of tumstatin a flexible linker consisting of 3 glycine residues Gly Gly Gly.

Structure of the fusion protein is shown schematically in FIG. 3, and its amino acid sequence and the DNA encoding sequence comprising codons optimized for expression in *E. coli* are, respectively, SEQ. No. 13 and SEQ. No. 43, as shown in the attached Sequence Listing.

The amino acid sequence SEQ. No. 13 was used as a template to generate its coding DNA sequence DNA SEQ. No. 43. A plasmid containing the coding sequence of DNA, with a sequence allowing to express His tag and a site recognized by thrombin, was generated and overexpression of the fusion protein was carried out in accordance with the general procedures described above. Overexpression was performed according to the general procedure B, using *E. coli* B.21 (DE3) strain from Novagen and BL21DE3pLysSRIL strain from Stratagene. The protein was separated by electrophoresis in accordance with the general procedure described above.

Example 14

The Fusion Protein of SEQ. No. 14

The protein of SEQ. No. 14 is a fusion protein having the length of 181 amino acids and the mass of 21 kDa, in which at the N-terminus of the sequence TRAIL 120-281 a fragment of EGF (SEQ. No. 23) is attached as an effector peptide. Between the effector peptide and the N-terminus of TRAIL domain the protein contains sequences of cleavage sites recognized by urokinase uPA (SEQ. No. 25) and metalloprotease MMP (SEQ. No. 56), due to which the effector peptide will undergo cleavage in the tumour environment.

Structure of the fusion protein is shown schematically in FIG. 3, and its amino acid sequence and the DNA encoding sequence comprising codons optimized for expression in *E. coli* are, respectively, SEQ. No. 14 and SEQ. No. 44, as shown in the attached Sequence Listing.

The amino acid sequence SEQ. No. 14 was used as a template to generate its coding DNA sequence DNA SEQ. No. 44. A plasmid containing the coding sequence of DNA, with a sequence allowing to express His tag and a site recognized by thrombin, was generated and overexpression of the fusion protein was carried out in accordance with the general procedures described above. Overexpression was performed according to the general procedure B, using *E. coli* BL21 (DE3) strain from Novagen and BL21DE3pLysSRIL strain from Stratagene. The protein was separated by electrophoresis in accordance with the general procedure described above.

Example 15

The Fusion Protein of SEQ. No. 15

The protein of SEQ. No. 15 is a fusion protein having the length of 217 amino acids and the mass of 24.4 kDa, in which at the N-terminus of the sequence hTRAIL95-281 a fragment of EGF (SEQ. No. 23) is attached as an effector peptide. Between the effector peptide and the N-terminus of TRAIL domain the protein contains sequences of cleavage sites recognized by urokinase uPA (SEQ. No. 25) and metalloprotease MMP (SEQ. No. 24), due to which the effector peptide will undergo cleavage in the tumour environment. Between the sequence of cleavage site recognized by metalloprotease MMP and the sequence of TRAIL the protein contains single proline residue followed by the flexible glycine-cysteine-alanine linker (SEQ. No. 26).

Structure of the fusion protein is shown schematically in FIG. 3, and its amino acid sequence and the DNA encoding sequence comprising codons optimized for expression in *E. coli* are, respectively, SEQ. No. 15 and SEQ. No. 45, as shown in the attached Sequence Listing.

The amino acid sequence SEQ. No. 15 was used as a template to generate its coding DNA sequence DNA SEQ. No. 45. A plasmid containing the coding sequence of DNA, with a sequence allowing to express His tag and a site recognized by thrombin, was generated and overexpression of the fusion protein was carried out in accordance with the general procedures described above. Overexpression was performed according to the general procedure B, using *E. coli* BL21 (DE3) strain from Novagen. The protein was separated by electrophoresis in accordance with the general procedure described above.

Example 16

The Fusion Protein of SEQ. No. 46

The fusion protein of SEQ. No. 46 is a fusion protein having the length of 211 amino acids and the mass of 24.4 kDa, in which at the N-terminus of the sequence TRAIL 95-281 two heptapeptides derived from VEGF (SEQ. No. 17) linked to each other are attached as effector peptides. Between the effector peptides the protein contains sequences of cleavage sites recognized by urokinase uPA (SEQ. No. 25) and metalloprotease MMP (SEQ. No. 55), due to which the effector peptide will undergo cleavage in the tumour environment.

Figure 9:
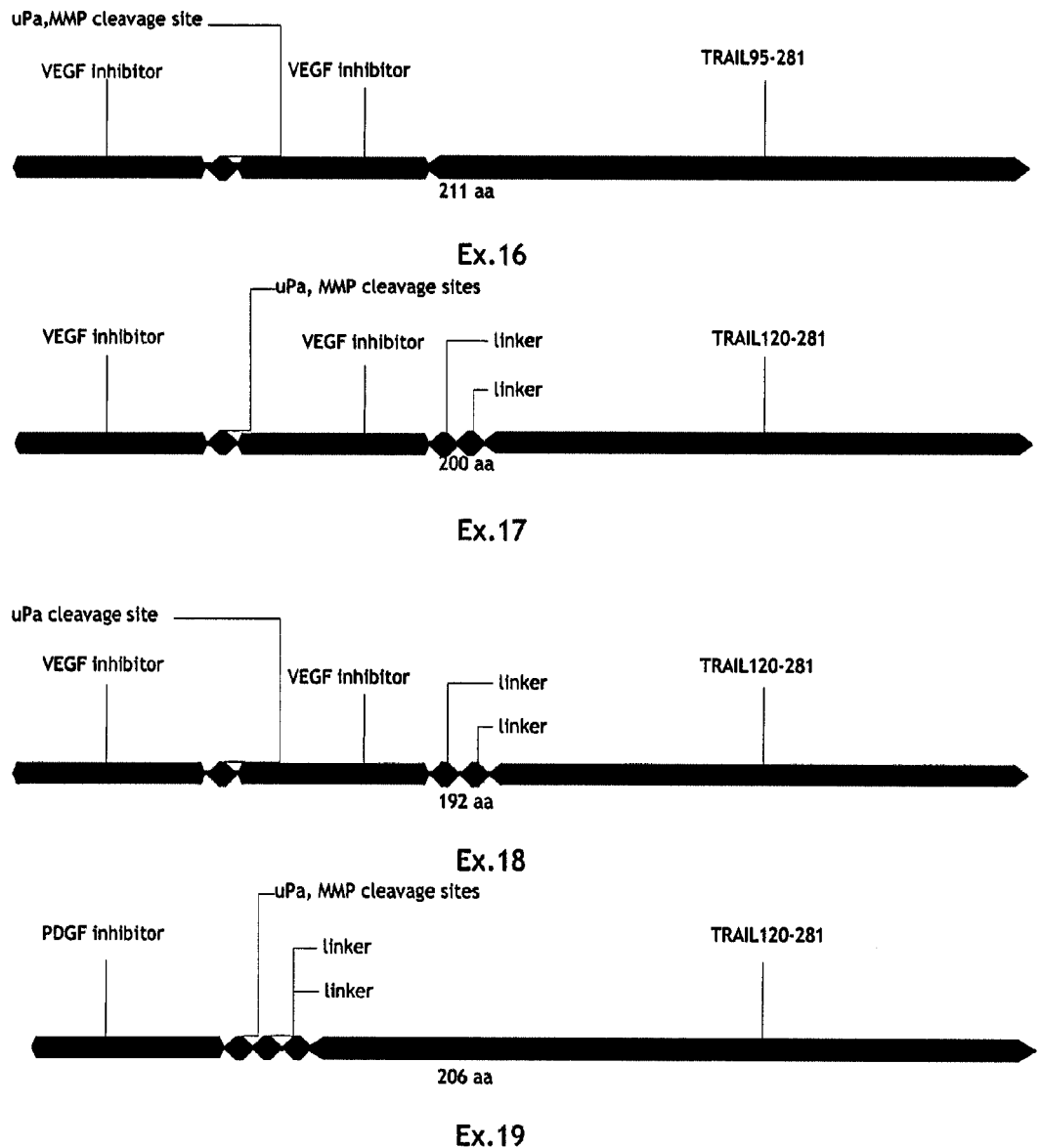
FIG. 9 presents a schematic structure of fusion proteins of the invention according to Ex. 16, Ex. 17, Ex. 18, and Ex. 19.

Structure of the fusion protein is shown schematically in FIG. 9, and its amino acid sequence and the DNA encoding sequence comprising codons optimized for expression in *E. coli* are, respectively, SEQ. No. 46 and SEQ. No. 50, as shown in the attached Sequence Listing.

The amino acid sequence SEQ. No. 46 was used as a template to generate its coding DNA sequence DNA SEQ. No. 50. A plasmid containing the coding sequence of DNA, with a sequence allowing to express His tag and a site recognized by thrombin, was generated and overexpression of the fusion protein was carried out in accordance with the general procedures described above. Overexpression was performed according to the general procedure B, using *E. coli* BL21 (DE3) strain from Novagen. The protein was separated by electrophoresis in accordance with the general procedure described above.

Example 17

The Fusion Protein of SEQ. No. 47

The fusion protein of SEQ. No. 47 is a fusion protein having the length of 200 amino acids and the mass of 22.7 kDa, in which at the N-terminus of the sequence TRAIL 120-281 two heptapeptides derived from VEGF (SEQ. No. 17) linked to each other are attached as effector peptides. Between the effector peptides the protein contains sequences of cleavage sites recognized by urokinase uPA (SEQ. No. 25) and metalloprotease MMP (SEQ. No. 55), due to which the effector peptide will undergo cleavage in the tumour environment. Between the effector protein and the TRAIL domain the protein contains subsequently flexible linker (SEQ. No. 26) promoting trimer formation and flexible glycine-serine linker (SEQ. no. 54).

Structure of the fusion protein is shown schematically in FIG. 9, and its amino acid sequence and the DNA encoding sequence comprising codons optimized for expression in *E. coli* are, respectively, SEQ. No. 47 and SEQ. No. 51, as shown in the attached Sequence Listing.

The amino acid sequence SEQ. No. 47 was used as a template to generate its coding DNA sequence DNA SEQ. No. 51. A plasmid containing the coding sequence of DNA, with a sequence allowing to express His tag and a site recognized by thrombin, was generated and overexpression of the fusion protein was carried out in accordance with the general procedures described above. Overexpression was performed according to the general procedure B, using *E. coli* BL21 (DE3) strain from Novagen. The protein was separated by electrophoresis in accordance with the general procedure described above.

Example 18

The Fusion Protein of SEQ. No. 48

The fusion protein of SEQ. No. 48 is a fusion protein having the length of 192 amino acids and the mass of 21.9 kDa, in which at the N-terminus of the sequence TRAIL 120-281 two heptapeptides derived from VEGF (SEQ. No. 17) linked to each other are attached as effector peptides. Between the effector peptides the protein contains sequence of cleavage site recognized by urokinase uPA (SEQ. No. 25), due to which the effector peptide will undergo cleavage in the tumour environment. Between the effector protein and the TRAIL domain the protein contains subsequently flexible linker (SEQ. No. 26) promoting trimer formation and flexible glycine-serine linker (SEQ. no. 54).

Structure of the fusion protein is shown schematically in FIG. 9, and its amino acid sequence and the DNA encoding sequence comprising codons optimized for expression in *E. coli* are, respectively, SEQ. No. 48 and SEQ. No. 52, as shown in the attached Sequence Listing.

The amino acid sequence SEQ. No. 48 was used as a template to generate its coding DNA sequence DNA SEQ. No. 52. A plasmid containing the coding sequence of DNA, with a sequence allowing to express His tag and a site recognized by thrombin, was generated and overexpression of the fusion protein was carried out in accordance with the general procedures described above. Overexpression was performed according to the general procedure B, using *E. coli* BL21 (DE3) strain from Novagen. The protein was separated by electrophoresis in accordance with the general procedure described above.

Example 19

The Fusion Protein of SEQ. No. 49

The protein of SEQ. No. 49 is a fusion protein having the length of 206 amino acids and the mass of 23.3 kDa, in which at the N-terminus of the sequence TRAIL120-281 a PDGF fragment (SEQ. No. 22) is attached as an effector peptide. Between the effector peptide and the sequence of TRAIL the protein contains sequences of cleavage sites recognized by urokinase uPA (SEQ. No. 25) and metalloprotease MMP (SEQ. No. 55), due to which the effector peptide will undergo cleavage in the tumour environment. Between the TRAIL sequence and the sequence of cleavage site recognized by metalloprotease MMP the protein contains also located subsequently flexible glycine-cysteine-alanine linker (SEQ. No. 26) promoting trimer formation and flexible glycine-serine linker (SEQ. no. 54).

Structure of the fusion protein is shown schematically in FIG. 9, and its amino acid sequence and the DNA encoding sequence comprising codons optimized for expression in *E. coli* are, respectively, SEQ. No. 49 and SEQ. No. 53, as shown in the attached Sequence Listing.

The amino acid sequence SEQ. No. 49 was used as a template to generate its coding DNA sequence DNA SEQ. No. 53. A plasmid containing the coding sequence of DNA, without a sequence allowing to express His tag and a site recognized by thrombin, was generated and overexpression of the fusion protein was carried out in accordance with the general procedures described above. Overexpression was performed according to the general procedure A, using *E. coli* BL21 (DE3) and Tuner(DE3)pLysS strains, both from Novagen. The protein was separated by electrophoresis in accordance with the general procedure described above.

Example 20

Examination of Anti-Tumor Activity of the Fusion Proteins

Examination of anti-tumor activity of the fusion proteins was carried out in vitro in a cytotoxicity assay on tumor cell lines and in vivo in mice. For comparison purposes, rhTRAIL114-281 protein and placebo were used.

1. Measurement of Circular Dichroism Determination of Secondary Structures Content of Obtained Proteins Quality of the preparations of fusion proteins in terms of their structure was determined by circular dichroism (CD) for Ex. 1, Ex. 4, Ex. 5, Ex. 9 and Ex. 14.

Circular dichroism is used for determination of secondary structures and conformation of protein. CD method uses optical activity of the protein structures, manifested in rotating the plane of polarization of light and the appearance of elliptical polarization. CD spectrum of proteins in far ultraviolet (UV) provides precise data on the conformation of the main polypeptide chain.

Dialysis

Samples of the protein to be analysed after formulation into a buffer consisting of 50 mM Tris-HCl pH 8.0, 100 mM NaCl, 10% glycerol, 0.1 mM $ZnCl_2$, 80 mM saccharose, 5 mM DTT, pH 7.4 (or alternatively 5 mM $NaH_2PO_4$, 95 mM $Na_2HPO_4$, 200 mM NaCl, 5 mM glutation, 0.1 mM $ZnCl_2$, 10% glycerol, 80 mM sacharose, pH 8.0 for proteins overexpressed as described above but lacking the His-tag and purified on SP Sepharose—marked in the results Table 5 with asterix *) were dialysed in the dialysis bags (Sigma-Aldrich) with cut off 12 kDa. Dialysis was performed against 100 fold excess (v/v) of buffer comparing to the protein preparations with stirring for several hours at 4° C. After dialysis was completed, each preparation was centrifuged (25 000 rpm., 10 min., 4° C.) and the appropriate supernatants were collected. Protein concentration in the samples thus obtained was determined by Bradford method as an average of triplicates.

Determination of Protein Concentration Using Bradford Method

In assays of protein concentration of the reagent prepared by dissolving 17.5 mg of Coomassie G-250 in a mixture of ethanol (4.8% v/v) phosphoric acid (V) (5.95% v/v) and water. To determine the protein concentration 1-10 ml of sample was added to 800 ml of Bradford reagent. A reference sample containing Bradford reagent and an appropriate volume of buffer in which the dissolved protein was determined. The absorbance was read on a spectrophotometer Cary 300 at a wavelength of 595 nm after at least 5 minutes incubation of the samples at room temperature. The protein concentration was calculated from the standard curve prepared for the BSA in the range of 10 concentrations 1-10 µg/ml. The starting protein concentration was estimated after taking into account the dilution during the preparation of the sample measurement.

Circular Dichroism Measurement

Measurement of circular dichroism for proteins in the concentration range of 0.1-2.7 mg/ml was performed on Jasco J-710 spectropolarimeter, in a quartz cuvette with optical way 0.2 mm or 1 mm. The measurement was performed under the flow of nitrogen at 7 l/min, which allowed to perform of the measurement in the wavelength range from 195 to 250 nm. Parameters of the measurement: spectral resolution of—1 nm; half width of the light beam 1 nm; sensitivity 20 mdeg, the averaging time for one wavelength—8 s, scan speed 10 nm/min, averaging of 3 measurements.

The results were presented as the average of three measurements. Circular dichroism spectra for rhTRAIL114-281 and proteins of Ex. 1, Ex. 4, Ex. 5, Ex. 9 and Ex. 14 are presented in FIG. 4.

Determination of Secondary Structure Content

Obtained spectra were analyzed numerically in the range of 193-250 nm using CDPro software. Points for which the voltage at the photomultiplier exceeded 700 V were omitted, due to too low signal to noise ratio in this wavelength range.

The data obtained served for calculations of particular secondary structures content in the analyzed proteins with use of CDPro software (Table 1).

TABLE 1

Content of secondary structures in the analyzed proteins

| Protein | NRMSD (Exp-Cal) | α-helix | β-sheet | Schift | Disorder |
|---|---|---|---|---|---|
| Ex.4 | 0.319 | 3.7% | 39.4% | 20.7% | 36.2% |
| Ex.1 | 0.093 | 7.8% | 8.6% | 63.1% | 20.5% |
| Ex.5 | 0.04 | 41.3% | 15.0% | 2.5% | 41.2% |
| Ex.9 | 0.112 | 2.9% | 41.0% | 20.7% | 35.4% |
| Ex.14 | 0.244 | 0.2% | 55.3% | 17.1% | 27.4% |
| rhTRAIL* | | 1.94% | 50.97% | 7.74% | 39.35% |
| rhTRAIL 114-281 | 0.389 | 4.9% | 33.7% | 23.1% | 38.3% |

*value obtained on the basis of crystalline structure 1D4V

Controls (rhTRAIL114-281) show CD spectrum characteristic for the proteins with predominantly type β-sheet structures (sharply outlined ellipticity minimum at the wavelength 220 nm). This confirms the calculation of secondary structure components, which suggests a marginal number of α-helix elements. The obtained result is also consistent with data from the crystal structure of hTRAIL protein and characteristic for the proteins of the invention of Ex. 4, Ex. 9 and Ex. 14, wherein beta elements constitute more than 40% of its composition.

In the case of all fused proteins, dichroism spectra are characterized by one minimum at wavelength 220 nm. Small effector proteins molecules attached to TRAIL in the fused proteins constitute the minor part of the protein and do not necessarily create a defined secondary structure, the analyzed proteins should not differ significantly from the initial protein. Significant differences, such as high content of alpha structures in the case of protein according to Ex. 5, or sheets such as observed for proteins from Ex. 1 are possibly due to limited range of CD spectrum subjected to analysis, especially in the region 180-200 nm.

2. In Vitro Cell Line Tests

Cell Lines

TABLE 2

Adherent cells

| Cell line | Cancer type | Medium | number of cells per well (thousands) |
|---|---|---|---|
| Colo 205 ATCC #CCL-222 | human colorectal cancer | RPMI + 10% FBS + penicillin + streptomycin | 5 |
| HT-29 ATCC #CCL-2 | human colorectal cancer | McCoy's + 10% FBS + penicillin + streptomycin | 5 |
| DU-145 ATCC #HTB-81 | human prostate cancer | RPMI + 10% FB5 + penicillin + streptomycin | 3 |
| PC-3 ATCC #CRL-1435 | human prostate cancer | RPMI + 10% FBS + penicillin + streptomycin | 4 |
| MCF-7 ATCC #HTB-22 | human breast cancer | MEM + 10% FBS + penicillin + streptomycin | 4.5 |
| MDA-MB-231 ATCC #HTB-26 | human breast cancer | DMEM + 10% FBS + penicillin + streptomycin | 4.5 |
| UM-UC-3 ATCC #CLR-1749 | human bladder cancer | MEM + 10% FBS + penicillin + streptomycin | 3.5 |
| SW780 ATCC #CRL-2169 | human bladder cancer | DMEM + 10% FBS + penicillin + streptomycin | 3 |
| SW620 ATCC #CCL-227 | human colorectal cancer | DMEM + 10% FBS + penicillin + streptomycin | 5 |
| BxPC-3 ATCC #CRL-1687 | human pancreatic cancer | RPMI + 10% FBS + penicillin + streptomycin | 4.5 |
| NIH: OVCAR-3 ATCC #HTB-161 | human ovarian cancer | RPMI + 20% FBS + 0.01 mg/ml insulin + penicillin + streptomycin | 7 |
| HepG2 ATCC #HB-8065 | human liver hepatoma | MEM + 10% FBS + penicillin + streptomycin | 7 |
| 293 ATCC #CLR-1573 | Human embrional kidney cells | MEM + 10% FBS + penicillin + streptomycin | 4 |
| ACHN ATCC #CCL-222 | human kidney cancer | MEM + 10% FBS + penicillin + streptomycin | 4 |

TABLE 2-continued

Adherent cells

| Cell line | Cancer type | Medium | number of cells per well (thousands) |
|---|---|---|---|
| CAKI 2 ATCC #HTB-47 | human kidney cancer | McCoy's + 10% FBS + penicillin + streptomycin | 3.5 |
| HT144 ATCC #HTB-63 | human melanoma cells | McCoy's + 10% FBS + penicillin + streptomycin | 7 |
| LNCaP ATCC #CRL-1740 | human prostate cancer | RPMI + 10% FBS + penicillin + streptomycin | 4.5 |
| NCI-H69 ATCC #HTB-119 | human small cell lung cancer | RPMI + 10% FBS + penicillin + streptomycin | 22 |
| Jurkat A3 ATCC #CRL-2570 | human leukaemia | RPMI + 10% FBS + penicillin + streptomycin | 10 |
| MES-SA/Dx5 ATCC #CRL-1977 | uterine cancer | McCoy's + 10% FBS + penicillin + streptomycin | 4 |
| SK-MES-1 ATCC #HTB-58 | human lung cancer | MEM + 10% FBS + penicillin + streptomycin | 4 |
| A549 ATCC #CCL-185 | human lung cancer | RPMI + 20% FBS + penicillin + streptomycin | 2.5 |
| HCT116 ATCC #CCL-247 | human colorectal cancer | McCoy's + 10% FBS + penicillin + streptomycin | 3 |
| MCF10A ATCC #CRL-10317 | mammary epithelial cells | DMEM-F12 (1:1) + 5% horse serum + 0.5 µg/ml hydrocortisone + 10 µg/ml insulin + 20 ng/ml EGF | 4.5 |
| MES-SA ATCC #CRL-1976 | uterine cancer | McCoy's + 10% FBS + penicillin + streptomycin | 3.5 |
| PANC-1 CLS #300228 | human pancreatic cancer | DMEM + 10% FBS + penicillin + streptomycin | 5 |

TABLE 3

Nonadherent cells:

| Cell line | Cancer type | Medium | Number of cells per well (thousands) |
|---|---|---|---|
| NCI-H69 ATCC# HTB-119 | human small cell lung cancer | RPMI + 10% FBS + penicillin + streptomycin | 22 |
| Jurkat A3 ATCC#CRL-2570 | human leukaemia | RPMI + 10% FBS + penicillin + streptomycin | 10 |
| HL60 ATCC# CCL-240 | human leukaemia | RPMI + 20% FBS + penicillin + streptomycin | 10 |
| CCRF-CEM ATCC# CCL-119 | human leukaemia | RPMI + 20% FBS + penicillin + streptomycin | 10 |

MTT Cytotoxicity Test

MIT assay is a colorimetric assay used to measure proliferation, viability and cytotoxicity of cells. It consists in decomposition of a yellow tetrazolium salt MTT (4,5-dimethyl-2-thiazolyl)-2,5-diphenyltetrazolium bromide) to the water-insoluble purple dye formazan by mitochondrial enzyme succinate-tetrazolium reductase 1. MTT reduction occurs only in living cells. Data analysis consists in determining $IC_{50}$ concentration of the protein (in ng/ml), at which the 50% reduction in the number of cells occurs in the population treated compared to control cells. Results were analyzed using GraphPad Prism 5.0 software. The test was performed according to the literature descriptions (Celis, J E, (1998). Cell Biology, a Laboratory Handbook, second edition, Academic Press, San Diego; Yang, Y., Koh, L W, Tsai, J H., (2004); Involvement of viral and chemical factors with oral cancer in Taiwan, Jpn J Clin Oncol, 34 (4), 176-183).

Cell culture medium was diluted to a defined density ($10^4$-$10^5$ cells per 100 µl). Then 100 µl of appropriately diluted cell suspension was applied to a 96-well plate in triplicates. Thus prepared cells were incubated for 24 h at 37° C. in 5% or 10% $CO_2$, depending on the medium used, and then to the cells (in 100 µl of medium) further 100 µl of the medium containing various concentrations of tested proteins were added. After incubation of the cells with tested proteins over the period of next 72 hours, which is equivalent to 3-4 times of cell division, the medium with the test protein was added with 20 ml of MTT working solution [5 mg/ml], and incubation was continued for 3 h at 37° C. in 5% $CO_2$. Then the medium with MTT solution was removed, and formazan crystals were dissolved by adding 100 µl of DMSO. After stirring, the absorbance was measured at 570 nm (reference filter 690 nm).

EZ4U Cytotoxicity Test

EZ4U (Biomedica) test was used for testing cytotoxic activity of the proteins in nonadherent cell lines. The test is a modification of the MTT wherein formazan formed in the reduction of tetrazolium salt is water-soluble. Cell viability study was carried out after continuous 72-hour incubation of the cells with protein (seven concentrations of protein, each in triplicates). On this basis $IC_{50}$ values were determined (as an average of two independent experiments) using the GraphPad Prism 5 software.

The results of in vitro cytotoxicity tests are summarized in Table 4 as $IC_{50}$ values (ng/ml), which correspond to a protein concentration at which the cytotoxic effect of fusion proteins is observed at the level of 50% with respect to control cells treated only with solvent.

In Table 4, proteins that were originally expressed with histidine tag that was subsequently removed are designated as a) at the Ex. No. Proteins that were originally expressed without histidine tag are designated as b) at the Ex. No. Each experiment represents the average value of at least two independent experiments performed in triplicates. As a criterion of lack of activity of protein preparations the $IC_{50}$ limit of 2000 ng/ml was adopted. Fusion proteins with an $IC_{50}$ value above 2000 were considered inactive.

Cells for this test were selected so as to include the tumour cell lines naturally resistant to TRAIL protein (the criterion of natural resistance to TRAIL: $IC_{50}$ for TRAIL protein>2000), tumour cell lines sensitive to TRAIL protein and resistant to doxorubicin line MES-SA/DX5 as a cancer line resistant to conventional anticancer medicaments.

Undifferentiated HUVEC cell line was used as a healthy control cell line for assessment of the effect/toxicity of the fusion proteins in non-cancer cells.

The results obtained confirm the possibility of overcoming the resistance of the cell lines to TRAIL by administration of certain fusion proteins of the invention to cells naturally resistant to TRAIL. When fusion proteins of the invention into the cells sensitive to TRAIL were administered, in some cases a clear and strong potentiation of the potency of action was observed, manifesting in reduced $IC_{50}$ values of the fusion protein compared with $IC_{50}$ for the TRAIL alone. Furthermore, cytotoxic activity of the fusion protein of the invention in the cells resistant to classical anti-cancer medicament doxorubicin was obtained, and in some cases was stronger than activity of TRAIL alone.

The $IC_{50}$ values above 2000 obtained for the non-cancer cell lines show the absence of toxic effects associated with the use of proteins of the invention for healthy cells, which indicates potential low systemic toxicity of the protein.

Determination of Cytotoxic Activity of Selected Protein Preparations Against Extended Panel of Tumour Cell Lines Table 5 presents the results of the tests of cytotoxic activity in vitro for selected fusion proteins of the invention against a broad panel of tumour cells from different organs, corresponding to the broad range of most common cancers.

In Table 5, proteins that were originally expressed with histidine tag that was subsequently removed are designated as a) at the Ex. No. Proteins that were originally expressed without histidine tag are designated as b) at the Ex. No.

Obtained $IC_{50}$ values confirm high cytotoxic activity of fusion protein and thus their potential utility in the treatment of cancer.

TABLE 4

Cytotoxic activity of fusion proteins of the invention

Continuous incubation of preparations with cells over 72 h (MTT test, ng/ml)

| | MES-SA | | MES-SA/Dx5 | | HCT116 | | SK-MES-1 | | A549 | | MCF10A | |
|---|---|---|---|---|---|---|---|---|---|---|---|---|
| Protein | $IC_{50}$ | ±SD | $IC_{50}$ | ±SD | $IC_{50}$ | ±SD | $IC_{50}$ | ±SD | $IC_{50}$ | ±SD | $IC_{50}$ | ±SD |
| rhTRAIL114-281 | >2000 | | 32.2 | 2.40 | 173 | 31.3 | 12.2 | 2.33 | >2000 | | >2000 | |
| Ex. 9[a)] | 3.96 | 1.44 | 3.250 | 0.95 | 3.95 | 9.95 | 3.00 | 2.34 | 131.10 | 43.98 | 1420.5 | 451.22 |
| Ex. 14[a)] | 2000 | | 1738.1 | 1.47 | 632.05 | 26.94 | 81.27 | 13.41 | 2000 | | 2000 | |
| Ex. 7[a)] | 2000 | | 6.822 | 2.83 | 38.66 | 11.34 | 5.80 | 1.93 | 2000 | | 2000 | |
| Ex. 1[a)] | 7.96 | 0.72 | 0.743 | 0.15 | 25.23 | 21.98 | 0.64 | 0.12 | 513.10 | 38.33 | 131.90 | 77.92 |
| Ex. 4[a)] | 4.79 | 0.78 | 3.69 | 1.05 | 14.27 | 2.48 | 0.43 | 0.15 | 705.15 | 40.38 | >2000 | |
| Ex. 5[a)] | 1.03 | 0.08 | 0.699 | 0.06 | 2.48 | 2.03 | 0.54 | 0.34 | 9.95 | 0.88 | 13.01 | 2.17 |
| Ex. 13[a)] | 83.03 | 21,.74 | 34.000 | 3.54 | 162.00 | 95.88 | 22.08 | 1.43 | 979.75 | 1.91 | 834.05 | 38.11 |

TABLE 5

Analysis of cytotoxic activity of selected protein preparations against broad panel of tumour cell

| Cell line | COLO 205 | | HT 29 | | SW 620 | | MCF 7 | | MDA-MB-231 | | DU 145 | | LNCaP | | PC 3 | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 | 24.90 | 17.68 | 10000 | 10000 | 10000 | 10000 | 10000 | 1642.60 | 10000 | 10000 | 10000 | 8928.00 | 2052.00 | 792.70 | 10000 | 10000 |
| Ex. 14[a] | 3.19 | 1.68 | | | | | | | | | | | 466.0 | 96.66 | 10000 | 10000 |

| Cell line | SW 780 | | UM-UC-3 | | 293 | | CAKI 2 | | SK-OV-3 | | OV-CAR-3 | | H69AR | | NCI-H69 | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 | 120.00 | 42.43 | 2242 | 1367 | 10000 | 8538 | 1734 | 218.5 | 10000 | 10000 | 93.10 | 8.34 | 10000 | 10000 | 10000 | 10000 |
| Ex. 14[a] | 93.13 | 33.76 | 30.37 | 3.10 | 2068 | | 1130 | 26.16 | 10000 | 10000 | 190.80 | 143.17 | 10000 | 10000 | 10000 | 10000 |

| Cell line | NCI-H460 | | BxPC3 | | HepG2 | | HT 144 | | ACHN | | JURKAT A3 | | HL60 | | CCRF-CEM | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 | 5889 | 111.0 | 64.71 | 31.81 | 10000 | 808.22 | 10000 | 218.5 | 10000 | 10000 | 93.10 | 8.34 | 10000 | 10000 | 10000 | 10000 |
| Ex. 14[a] | 186.80 | 76.72 | 79.60 | 18.81 | 6153 | | 3650 | 26.16 | 10000 | 10000 | 190.80 | 143.17 | 10000 | 10000 | 10000 | 10000 |

| Cell line | COLO 205 | | HT 29 | | SW 620 | | MCF 7 | | MDA-MB-231 | | DU 145 | | LNCaP | | PC 3 | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 | 24.90 | 17.68 | 10000 | 10000 | 10000 | | 10000 | 1642.60 | 10000 | 10000 | 10000 | 64.33 | 2052.00 | 254.00 | 10000 | 980.60 |
| Ex. 1[a] | 0.87 | 0.19 | | | | | | | | | 22.31 | | 466.0 | 4.24 | | |

| Cell line | SW 780 | | UM-UC-3 | | 293 | | CAKI 2 | | SK-OV-3 | | OV-CAR-3 | | H69AR | | NCI-H69 | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 | 120.00 | 42.43 | 2242 | 1367 | 10000 | 128.70 | 1734 | 329.20 | 10000 | 10000 | 93.10 | 8.34 | 10000 | 10000 | 10000 | 10000 |
| Ex. 1[a] | 3.78 | 0.22 | 852.60 | 7.03 | 633 | | 832 | | 23.83 | 0.54 | 64.33 | 22.31 | 1530 | 137 | 1436 | |

| Cell line | NCI-H460 | | BxPC3 | | HepG2 | | HT 144 | | ACHN | | JURKAT A3 | | HL60 | | CCRF-CEM | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 | 5889 | 111.0 | 64.71 | 31.81 | 10000 | 89.73 | 10000 | 61.50 | 10000 | 379 | 10000 | 5.58 | 10000 | 10000 | 10000 | 10000 |
| Ex. 1[a] | 7.71 | 0.09 | 2.57 | 0.43 | 84350 | 3.80 | 230.50 | 1.11 | 2116 | | 5.09 | 2.94 | 1339 | | 1357 | |

| Cell line | COLO 205 | | HT 29 | | SW 620 | | MCF 7 | | MDA-MB-231 | | DU 145 | | LNCaP | | PC 3 | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 | 24.90 | 17.68 | 10000 | 1600 | 10000 | 17.00 | 10000 | 11.17 | 10000 | 8.92 | 10000 | 63.64 | 2052 | 1600 | 10000 | 1056 |
| Ex. 5[a] | 12.24 | 3.65 | | | 1600 | | 684.50 | | 345 | | 473 | | | | | |

TABLE 5-continued

Analysis of cytotoxic activity of selected protein preparations against broad panel of tumour cell

| Cell line | SW 780 | | UM-UC-3 | | 293 | | CAKI 2 | | SK-OV-3 | | OV-CAR-3 | | H69AR | | NCI-H69 | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 | 120.00 | 42.43 | 2242 | 134.80 | 10000 | 1600 | 10000 | 1303 | 10000 | 1600 | 93.10 | 8.34 | 10000 | 1600 | 10000 | 1600 |
| Ex. 5a) | 38.46 | 1.03 | 118.90 | 9.55 | 1315 | 389.62 | 57.44 | 1.89 | 510.00 | 76.37 | 79.25 | 27.93 | 1600 | | 1600 | |

| Cell line | NCI-H460 | | BxPC3 | | HepG2 | | HT 144 | | ACHN | | JURKAT A3 | | HL60 | | CCRF-CEM | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 | 5889 | 111.0 | 64.71 | 31.81 | 10000 | | 1734 | 218.5 | 10000 | | 10000 | 4.00 | 10000 | | 10000 | |
| Ex. 5a) | 118.90 | 28.14 | 93.90 | 1.41 | | | 57.44 | 1.89 | 510.00 | | 30.15 | | 1600 | | 1600 | |

| Cell line | COLO 205 | | HT 29 | | SW 620 | | MCF 7 | | MDA-MB-231 | | DU 145 | | LNCaP | | PC 3 | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 | 24.90 | 17.68 | 10000 | | 10000 | | 10000 | | 10000 | | 10000 | 9.81 | 2052 | 466.0 | 10000 | 463.90 |
| Ex. 9a) | 0.013 | 0.01 | 264.20 | 46.95 | 47.86 | 12.50 | 1025 | 190.10 | 1.276 | 0.40 | 15.77 | | 32.90 | 27.01 | | |

| Cell line | SW 780 | | UM-UC-3 | | 293 | | CAKI 2 | | SK-OV-3 | | OV-CAR-3 | | H69AR | | NCI-H69 | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 | 120.00 | 42.43 | 2242 | 134.80 | 10000 | | 10000 | | 10000 | | 93.10 | 8.34 | 10000 | | 10000 | |
| Ex. 9a) | 1.006 | | 0.136 | 0.07 | 181.60 | 44.50 | 24.42 | | 2500 | | 0.456 | 0.64 | 818.60 | 130.67 | 2500 | |

| Cell line | NCI-H460 | | BxPC3 | | HepG2 | | HT 144 | | ACHN | | JURKAT A3 | | HL60 | | CCRF-CEM | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 | 5889 | 111.0 | 10000 | | 10000 | | 1734 | 218.5 | 10000 | | 10000 | 1.00 | 10000 | | 10000 | |
| Ex. 9a) | 0.004 | 0.01 | 8500 | | 8500 | | 0.845 | 1.20 | 8500 | | 0.615 | | 2500 | | 2500 | |

| Cell line | COLO 205 | | HT 29 | | SW 620 | | MCF 7 | | MDA-MB-231 | | DU 145 | | LNCaP | | PC 3 | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 | 24.90 | 17.68 | 10000 | | 10000 | | 10000 | | 10000 | | 10000 | 1109 | 2052.00 | 466.0 | 10000 | |
| Ex. 7a) | 3.04 | 0.32 | 8500 | | 6767 | 2188 | 8500 | | 58.00 | 2.12 | 4062 | | 3250 | 766.50 | 8500 | |

| Cell line | SW 780 | | UM-UC-3 | | 293 | | CAKI 2 | | SK-OV-3 | | OV-CAR-3 | | H69AR | | NCI-H69 | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 | 120.00 | 42.43 | 2242 | | 10000 | | 10000 | | 10000 | | 93.10 | 8.34 | 10000 | | 10000 | |
| Ex. 7a) | 7.01 | 2.58 | 7.63 | 0.51 | 8500 | 1.31 | 8500 | | 8500 | | 15.14 | 2.62 | 8500 | | 8500 | |

TABLE 5-continued

Analysis of cytotoxic activity of selected protein preparations against broad panel of tumour cell

| Cell line | NCI-H460 | | BxPC3 | | HepG2 | | HT144 | | ACHN | | JURKAT A3 | | HL60 | | CCRF-CEM | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 Ex. 7[a] | 5889 | 111.0 | 64.71 | 31.81 | 10000 | 8500 | 1734 | 218.5 | 10000 | 8500 | 10000 | 8500 | 10000 | 8500 | 10000 | 8500 |
| | 7.11 | 1.52 | 7.94 | 3.19 | | | 92.05 | 40.52 | | | | | | | | |

| Cell line | A549 | | HCT116 | | MCF10A | | MES-SA/Dx5 | | SK-MES-1 | | | | | | | |
|---|---|---|---|---|---|---|---|---|---|---|---|---|---|---|---|---|
| | mean | SD | mean | SD | mean | SD | mean | SD | mean | SD | | | | | | |
| rhTRAIL 95-281 Ex. 9[b] | >10000 | | 7557 | 3454 | >10000 | 1169 | 29.15 | 12.66 | 39.35 | 8.13 | | | | | | |
| | 391.00 | 52.33 | 2473 | 3.44 | | | <0.001 | | 3.58 | 0.81 | | | | | | |

| Cell line | A549 | | HCT116 | | MCF10A | | MES-SA | | MES-SA/Dx5 | | SK-MES-1 | | NCI-H460 | | | |
|---|---|---|---|---|---|---|---|---|---|---|---|---|---|---|---|---|
| | mean | SD | mean | SD | mean | SD | mean | SD | mean | SD | mean | SD | mean | SD | | |
| rhTRAIL 95-281 Ex. 16[a] | >10000 | | 7557 | 3454 | >10000 | | 29.15 | 12.66 | 29.15 | 12.66 | 39.35 | 8.13 | 5889 | 111 | | |
| | 224.84 | 268.26 | 500 | | 99.27 | 51.24 | 0.36 | 0.25 | 0.007 | 0.00 | 5 | | 22.76 | | | |

| Cell line | A549 | | HCT116 | | MCF10A | | MES-SA | | MES-SA/Dx5 | | SK-MES-1 | | HT29 | | NCI-H460 | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 Ex. 6[a] | >10000 | | >10000 | | >10000 | | 29.15 | 12.66 | 29.15 | 12.66 | 39.35 | 8.13 | >10000 | | 5889 | 111 |
| | 422.70 | 102.18 | 147.80 | 3.96 | 129.90 | | 0.01 | | 0.0068 | 0.0043 | 1.41 | | 69.19 | 18.79 | 0.02 | |

| Cell line | PANC1 | | PLC/PRF/5 | | Colo 205 | | HepG2 | | BxPc3 | | SW 620 | | UM-UC-3 | | | |
|---|---|---|---|---|---|---|---|---|---|---|---|---|---|---|---|---|
| | mean | SD | mean | SD | mean | SD | mean | SD | mean | SD | mean | SD | mean | SD | | |
| rhTRAIL 95-281 Ex. 6[a] | >10000 | | >9000 | | >10000 | 17.68 | 24.90 | | >10000 | | >10000 | 80.89 | 293 | | | |
| | 2.15 | 0.79 | 2.35 | | 95.44 | | 0.003 | | 0.062 | | 398.80 | | | | | |

| Cell line | A549 | | MCF10A | | MES-SA/Dx5 | | SK-MES-1 | | PANC1 | | | | | | | |
|---|---|---|---|---|---|---|---|---|---|---|---|---|---|---|---|---|
| | mean | SD | mean | SD | mean | SD | mean | SD | mean | SD | | | | | | |
| rhTRAIL 95-281 Ex. 1[b] | >10000 | | >10000 | | 29.15 | 12.66 | 39.35 | 8.13 | 64.71 | 12.66 | | | | | | |
| | 346.75 | 422.70 | 4.677 | 2.23 | 0.0068 | | 84.50 | 3.82 | 12.38 | 4.20 | | | | | | |

| Cell line | A549 | | HCT116 | | MCF10A | | MES-SA | | MES-SA/Dx5 | | SK-MES-1 | | HT29 | | NCI-H460 | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 Ex. 11[a] | >10000 | | 7557 | 3454 | >10000 | | 29.15 | 8.13 | 29.15 | 12.66 | 39.35 | 8.13 | >10000 | 1367 | 5889 | 111 |
| | 106.66 | 41.49 | 11.50 | 3.42 | 3.50 | | 5.28 | 1.07 | 0.445 | 0.30 | 4.99 | | 911.50 | 282.14 | 9.34 | 5.27 |

TABLE 5-continued

Analysis of cytotoxic activity of selected protein preparations against broad panel of tumour cell

| Cell line | PANC1 mean | SD | PLC/PRF/5 mean | SD |
|---|---|---|---|---|
| rhTRAIL 95-281 Ex. 11[a] | >10000 | 3.07 | >9000 | <0.001 |

| Cell line | A549 mean | SD | HCT116 mean | SD | MCF10A mean | SD | MES-SA mean | SD | MES-SA/Dx5 mean | SD | SK-MES-1 mean | SD | NCI-H460 mean | SD | Colo 205 mean | SD |
|---|---|---|---|---|---|---|---|---|---|---|---|---|---|---|---|---|
| rhTRAIL 95-281 Ex. 19[a] | >10000 | 4.31 | 7557 | <0.001 | >10000 | 0.19 | >10000 | <0.001 | 29.15 | <0.001 | 39.35 | <0.001 | 5889 | <0.001 | 24.90 | 0.004 |

| Cell line | HepG2 mean | SD | BxPc3 mean | SD | HCT116 mean | SD | | | | | | | | | SK-MES-1 mean | SD |
|---|---|---|---|---|---|---|---|---|---|---|---|---|---|---|---|---|
| rhTRAIL 95-281 Ex. 19[a] | >10000 | 0.20 | 64.71 | 0.013 | 7557 3454 | 31.81 | | | | | | | | | 39.35 | 8.13 1.31 |

| Cell line | A549 mean | SD | HCT116 mean | SD | MCF10A mean | SD | MES-SA mean | SD | rhTRAIL 95-281 Ex. 2[a] | | SK-MES-1 mean | SD | HCT116 mean | SD | BxPc3 mean | SD |
|---|---|---|---|---|---|---|---|---|---|---|---|---|---|---|---|---|
| rhTRAIL 95-281 Ex. 13[a] | >10000 | 979.75 1.91 | 7557 3454 | 12.45 | >10000 | 834.05 38.11 | >10000 | 83.03 21.74 | | | 39.35 | 22.08 | 7557 | 275.10 67.46 | 64.71 | 79.6 18.81 |

| Cell line | A549 mean | SD | HCT116 mean | SD | MCF10A mean | SD | MES-SA mean | SD | Cell line | rhTRAIL 95-281 Ex. 14[a] | SK-MES-1 mean | SD | MES-SA/Dx5 mean | SD | | |
|---|---|---|---|---|---|---|---|---|---|---|---|---|---|---|---|---|
| rhTRAIL 95-281 Ex. 17[a] | >10000 | 233.90 15.04 | 7557 3454 | 30.33 2.39 | >10000 | 174.10 | >10000 | 7.4 | | 1.43 | 39.35 | 2.9 | 29.15 | 12.66 0.07 | | |

| Cell line | HCT116 mean | SD | MES-SA mean | SD | MCF10A mean | SD | SK-MES-1 mean | SD | MES-SA/Dx5 mean | SD | SK-MES-1 mean | SD | | | | |
|---|---|---|---|---|---|---|---|---|---|---|---|---|---|---|---|---|
| rhTRAIL 95-281 Ex. 18[a] | >10000 | 34.28 0.01 | >10000 | 11.67 0.005 | >10000 | 19.29 0.004 | 39.35 | 8.13 0.005 | 29.15 | 1.589 0.264 | 39.35 | 8.13 0.615 | | | | |

| Cell line | HCT116 mean | SD | MES-SA mean | SD | HT29 mean | SD | SK-MES-1 mean | SD | NCI-H460 mean | SD | PANC1 mean | SD | PLC/PRF/5 mean | SD | Colo 205 mean | SD |
|---|---|---|---|---|---|---|---|---|---|---|---|---|---|---|---|---|
| rhTRAIL 95-281 Ex. 5[b] | 7557 | 0.036 3454 | >10000 | 0.005 | >10000 | 783.50 34.65 | 39.35 | 1.24 0.97 | 5889 | 0.25 111 | >10000 | 1.05 0.56 | >9000 | 5.54 | 24.90 | 17.68 3.65 |

TABLE 5-continued

Analysis of cytotoxic activity of selected protein preparations against broad panel of tumour cell

| Cell line | HepG2 | | BxPc3 | | ACHN | | OV-CAR-3 | | Colo 205 | | BxPc3 | | DU 145 | | OV-CAR-3 | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 Ex. 5[b] | >10000 | 9.27 | 64.71 | 31.81 0.36 0.44 | >10000 | 0.5 | 963.00 <0.001 | 144.25 0.001 | | | rhTRAIL 95-281 Ex. 7[a] | | >10000 | 1109 4061 | 963 15.14 | 144.25 2.62 |

| Cell line | HCT116 | | MES-SA/Dx5 | | SK-MES-1 | | NCI-H460 | | HT29 | | NCI-H460 | | SW 780 | | UM-UC-3 | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 Ex. 7[b] | 7557 | 3454 7.99 1.20 | 29.15 6.822 | 12.66 2.83 | 39.35 5.80 | 8.13 1.93 | 5889 7.11 | 111 1.52 | 24.90 3.04 | 17.68 0.32 | | | 120 7.01 | 42.43 2.58 | 2242 7.63 | 1367 0.51 |

| Cell line | MCF10A | | MES-SA | | MES-SA/Dx5 | | SK-MES-1 | | PANC1 | | PLC/PRF/5 | | PANC1 | | PLC/PRF/5 | |
|---|---|---|---|---|---|---|---|---|---|---|---|---|---|---|---|---|
| | mean | SD | mean | SD | mean | SD | mean | SD | mean | SD | mean | SD | mean | SD | mean | SD |
| rhTRAIL 95-281 Ex. 9[b] | >10000 | 10.30 4.15 | >10000 | <0.001 | 29.15 0.008 | 12.66 | 39.3 0.02 | 8.1 | >10000 | 264.2 46.9 | | | >10000 | 0.025 0.035 | >9000 | 21.87 3.58 |

| Cell line | ACHN | | SW 780 | | UM-UC-3 | | SK-MES-1 | | PANC1 | | | | NCI-H460 | | PANC1 | |
|---|---|---|---|---|---|---|---|---|---|---|---|---|---|---|---|---|
| | mean | SD | mean | SD | mean | SD | mean | SD | mean | SD | | | mean | SD | mean | SD |
| rhTRAIL 95-281 Ex. 9[a] | >10000 | 4.46 1.98 | 120 <0.001 | 42.43 | 2242 0.14 | 1367 | 39.3 0.43 | 8.13 0.15 | >10000 128.00 | | rhTRAIL 95-281 Ex. 15[a] | 0.07 | >9000 3722 | | 5889 15.20 | 111 128 |

| Cell line | HCT116 | | MES-SA | | MES-SA/Dx5 | | | | PC3 | | | | | | UM-UC-3 | |
|---|---|---|---|---|---|---|---|---|---|---|---|---|---|---|---|---|
| | mean | SD | mean | SD | mean | SD | | | mean | SD | | | | | mean | SD |
| rhTRAIL 95-281 Ex. 4[b] | 7557 | 3454 14.27 2.48 | >10000 4.79 | 0.78 | 29.15 3.69 | 12.66 1.05 | | | >10000 1056 | 180.9 | rhTRAIL 95-281 Ex. 14[a] | | | | 2242 30.37 | 1367 3.10 |

3. Antitumour Effectiveness of Fusion Proteins In Vivo on Xenografts

Antitumour activity of protein preparations was tested in a mouse model of human colon cancer HCT116, Colo205 and SW620 cells, human non-small cell lung cancer A549 and NCI-H460-Luc2 cells, human hepatoma PLC/PRF/5 (CLS) cells, human pancreatic carcinoma PANC-1 cells, human liver carcinoma HepG2 cells, human large-cell lung carcinoma NCI-H460 cells, and human uterine carcinoma MES-SA/Dx5 multidrug resistant cells.

Cells

The HCT116 and A549 (ATCC CCL-185) cells were maintained in RPMI 1640 medium (Hyclone, Logan, Utah, USA) mixed in the ratio of 1:1 with Opti-MEM (Invitrogen, Cat. 22600-134) supplemented with 10% fetal calf serum and 2 mM glutamine. On the day of mice grafting, the cells were detached from the support by washing the cells with trypsin (Invitrogen), then the cells were centrifuged at 1300 rpm, 4'C, 8 min., suspended in HBSS buffer (Hanks medium), counted and diluted to the concentration of $25 \times 10^6$ cells/ml.

The PLC/PRF/5 (CLS), SW620 and PANC-1 cells were maintained in DMEM (HyClone, Logan, Utah, USA) supplemented with 10% fetal calf serum and 2 mM glutamine. On the day of mice grafting, the cells were detached from the support by washing the cells with trypsin (Invitrogen), then the cells were centrifuged at 1300 rpm, 4° C., 8 min., suspended in HBSS buffer (Hanks medium), counted and diluted to the concentration of $25 \times 10^6$ cells/ml.

The HepG2 cells were maintained in MEM (HyClone, Logan, Utah, USA) supplemented with 10% fetal calf serum and 2 mM glutamine. On the day of mice grafting, the cells were detached from the support by washing the cells with trypsin (Invitrogen), then the cells were centrifuged at 1300 rpm, 4° C., 8 min., suspended in HBSS buffer (Hanks medium), counted and diluted to the concentration of $25 \times 10^6$ cells/ml.

The NCI-H460-Luc2, NCI-H460 and Colo205 were maintained in RPMI1640 (HyClone, Logan, Utah, USA) supplemented with 10% fetal calf serum and 2 mM glutamine. On the day of mice grafting, the cells were detached from the support by washing the cells with trypsin (Invitrogen), then the cells were centrifuged at 1300 rpm, 4° C., 8 min., suspended in HBSS buffer (Flanks medium), counted and diluted to the concentration of $25 \times 10^6$ cells/ml. The MES-SA/Dx5 cells were maintained in McCoy's (HyClone, Logan, Utah, USA) supplemented with 10% fetal calf serum and 2 mM glutamine. On the day of mice grafting, the cells were detached from the support by washing the cells with trypsin (Invitrogen), then the cells were centrifuged at 1300 rpm, 4° C., 8 min., suspended in HBSS buffer (Hanks medium), counted and diluted to the concentration of $25 \times 10^6$ cells/ml.

Mice

Examination of antitumor activity of proteins of the invention was conducted on 4-5 week-old or 7-9 week-old CD-nude (Crl:CD1-Foxn1$^{nu}$ 1) or on 4-5 week old Crl:SHO-Prkdc$^{scid}$Hr$^{hr}$ mice obtained from Charles River Germany or 4-5 week-old Cby.Cg-foxn1(nu)/J mice obtained from Centrum Medycyny Doświadczalnej in Bialystok. Mice were kept under specific pathogen-free conditions with free access to food and demineralised water (ad libitum). All experiments on animals were carried in accordance with the guidelines: "Interdisciplinary Principles and Guidelines for the Use of Animals in Research, Marketing and Education" issued by the New York Academy of Sciences' Ad Hoc Committee on Animal Research and were approved by the IV Local Ethics Committee on Animal Experimentation in Warsaw (No. 71/2009).

The Course and Evaluation of the Experiments

Tumor size was measured using an electronic calliper, tumor volume was calculated using the formula: $(a^2 \times b)/2$, where a=shorter diagonal of the 25 tumor (mm) and b=longer diagonal of the tumor (mm). Inhibition of tumor growth was calculated using the formula:

TGI [%] (Tumor growth inhibition)=(WT/WC)×100−100% wherein WT refers to the average tumor volume in the treatment group, WC refers to the average tumor volume in the control group.

The experimental results are presented as a mean value±standard deviation (SD). All calculations and graphs were prepared using the GraphPad Prism 5.0 software.

Human Colon Cancer Model

Mice Crl:CD1-Foxn1$^{nu}$ 1

On day 0 mice Crl:CD1-Foxn1$^{nu}$ 1 were grafted subcutaneously (sc) in the right side with $5 \times 10^6$ of HCT116 cells suspended in 0.2 ml HBSS buffer by means of a syringe with a 0.5×25 mm needle (Bogmark). When tumors reached the size of ~60-90 mm$^3$ (day 14), mice were randomized to obtain the average size of tumors in the group of ~70 mm$^3$ and assigned to treatment groups. The treatment groups were administered with the preparations of fusion proteins of the invention of Ex. 1 (10 mg/kg), Ex. 4 (10 mg/kg), Ex. 5 (10 mg/kg), and Ex. 9 (10 mg/kg), and rhTRAIL114-281 (10 mg/kg) as a comparison. The preparations were administered intravenously (i.v.) daily for ten days. When a therapeutic group reached the average tumor size of ~1000 mm$^3$, mice were sacrificed by disruption of the spinal cord. The control group received rhTRAIL114-281.

Figure 5:
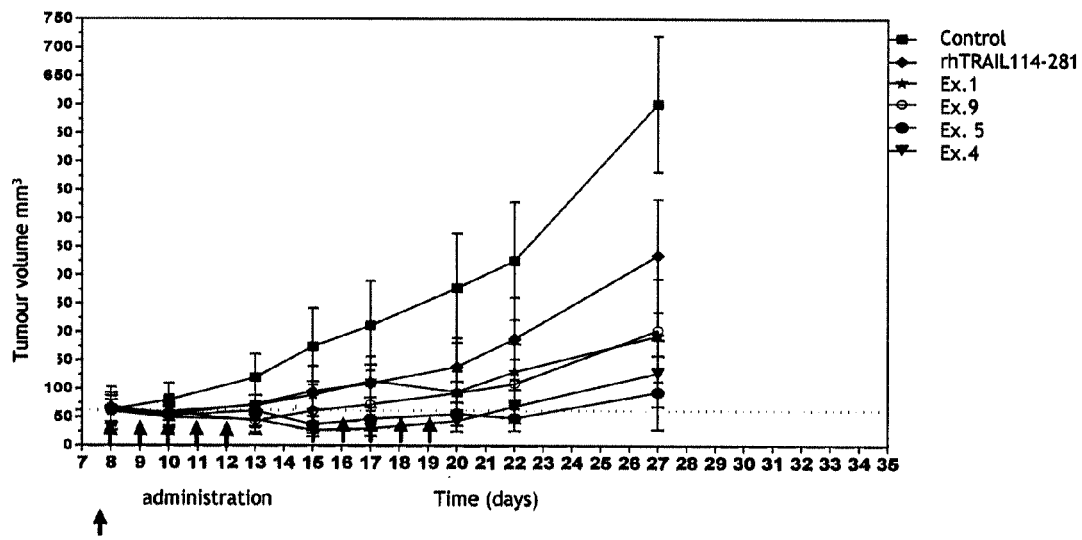
FIG. 5 presents tumor volume changes (% of initial stage) in Crl:CD1-Foxn1nu mice burdened with colon cancer HCT116 treated with fusion proteins of the invention of Ex. 1, Ex. 4, Ex. 5 and Ex. 9 compared to rhTRAIL114-281
Figure 6:
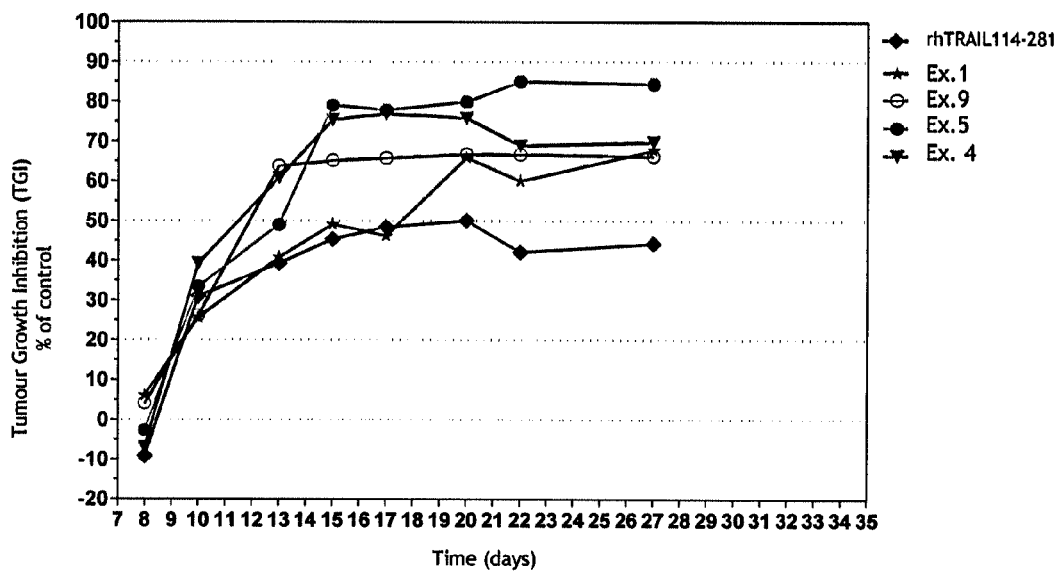
FIG. 6 presents the tumor growth inhibition values (% TGI) in Crl:CD1-Foxn1$^{nu}$ 1 mice burdened with colon cancer HCT116 treated with fusion proteins of the invention of z Ex. 1, Ex. 4, Ex. 5 and Ex. 9 compared to rhTRAIL114-281.

The experimental results obtained in mice Crl:CD1-Foxn1$^{nu}$ burdened with HCT116 colon cancer treated with fusion proteins of the invention of Ex. 1, Ex. 4, Ex. 5 and Ex. 9 and comparatively with rhTRAIL114-281 are shown in FIG. 5 as a diagram of changes of the tumor volume and in FIG. 6 which shows tumor growth inhibition (% TGI) as the percentage of control.

The results of experiments presented in the graphs in FIGS. 5 and 6 show that administration of the fusion proteins of the invention of Ex. 1, Ex. 4, Ex. 5 and Ex. 9 caused tumor HCT116 growth inhibition, with TGI respectively 67.8; 69.8; 84.4 and 66.2% relative to the control on 27$^{th}$ day of the experiment. For rhTRAIL114-281 used as the comparative reference, a slight inhibitory effect on tumor cell growth was obtained relative to the control, with TGI at the level of 44%. Thus, fusion proteins of the invention exert much stronger effect compared to rhTRAIL114-281 alone.

Mice Crl:CD1-Foxn1$^{nu}$

HT116 Model

On day 0 mice Crl:CD1-Foxn1$^{nu}$ were grafted subcutaneously (sc) in the right side with $5 \times 10^6$ of HCT116 cells suspended in 0.2 ml HBSS buffer by means of a syringe with a 0.5×25 mm needle (Bogmark). When tumors reached the size of ~50-78 mm$^3$ (day 8), micewco randomized to obtain the average size of tumors in the group of ~63 mm$^3$ and assigned to treatment groups. The treatment groups were administered with the preparations of fusion proteins of the invention of Ex. 5 (10 mg/kg), Ex. 4 (10 mg/kg), Ex. 9 (10 mg/kg), Ex. 1 (10 mg/kg) and rhTRAIL114-281 (10 mg/kg) as a comparison against formulation buffer (50 mM Trizma Base, 150 mM NaCl, 80 mM Saccharose, 250 mM L-arginine, 1 mM glutation, Zn$^{2+}$ 0.1 mM, pH 7.3) as a control. The preparations were administered intravenously (i.v.) daily for five days, followed by (after 2-days break) another five daily administrations. When a therapeutic group reached the average tumor size of ~1000 mm$^3$, mice were sacrificed by disruption of the spinal cord. The control group received rhTRAIL114-281.

Figure 10:
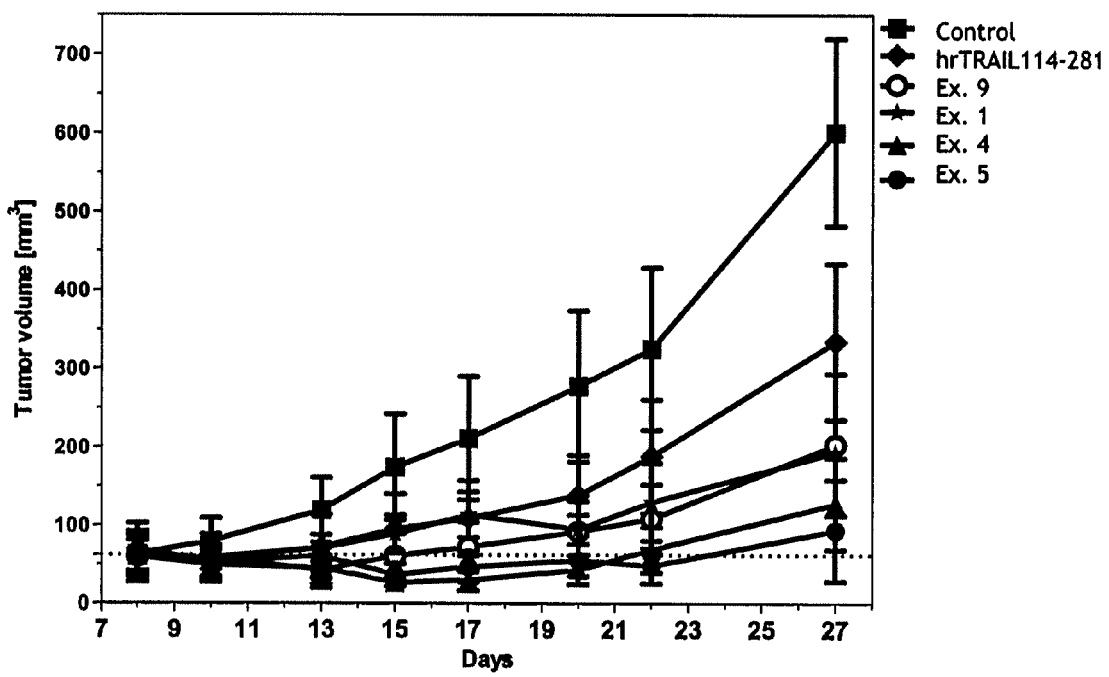
FIG. 10 presents tumor volume changes (% of initial stage) in Crl:CD1-Foxn1nu mice burdened with colon cancer HCT116 treated with fusion proteins of the invention from Ex. 5, Ex. 4, Ex. 9, and Ex. 1 compared to rhTRAIL114-281.
Figure 11:
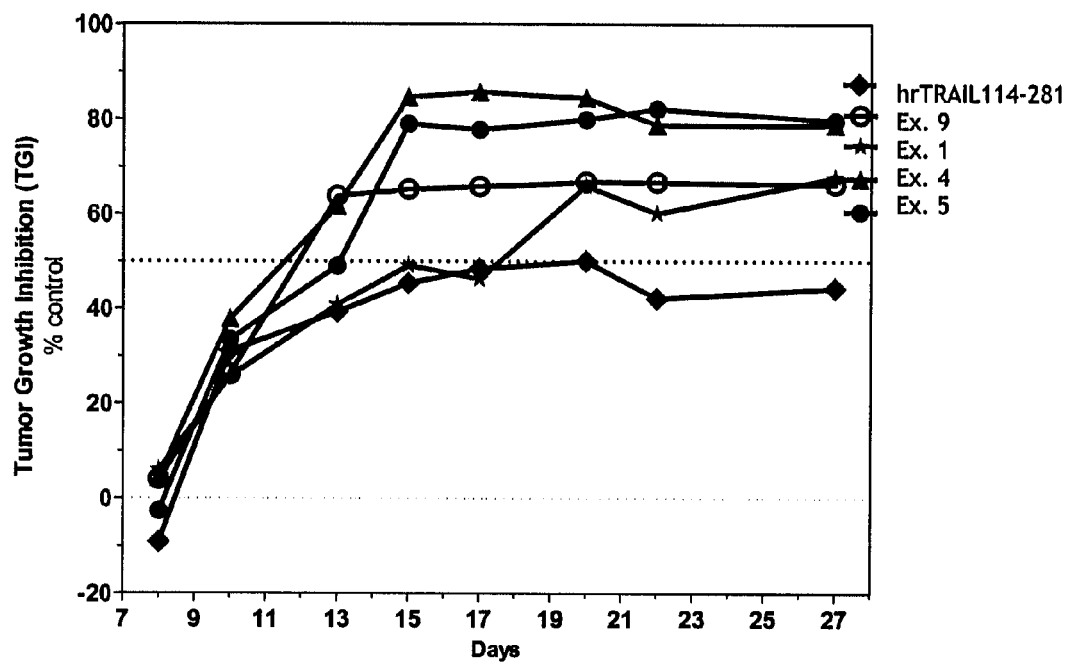
FIG. 11 presents the tumor growth inhibition values (% TGI) in Crl:CD1-Foxn1$^{nu}$ 1 mice burdened with colon cancer HCT116 treated with fusion proteins of the invention from Ex. 5, Ex. 4, Ex. 9, and Ex. 1 compared to rhTRAIL114-281.

The experimental results obtained in mice Crl:CD1-Foxn1$^{nu}$ burdened with HCT116 colon cancer treated with fusion proteins of the invention of Ex. 5, Ex. 4, Ex. 9, Ex. 1 and comparatively with rhTRAIL114-281 are shown in FIG. 10 as a diagram of changes of the tumor volume and in FIG. 11 which shows tumor growth inhibition (% TGI) as the percentage of control.

The results of experiments presented in the graphs in FIGS. 10 and 11 show that administration of the fusion proteins of the invention of Ex. 5, Ex. 4, Ex. 9, and Ex. 1 caused tumor HCT116 growth inhibition, with TGI respectively 80%, 79%, 66% and 68% relative to the control on 27$^{th}$ day of the experiment. For rhTRAIL114-281 used as the comparative reference, a slight inhibitory effect on tumor cell growth was obtained relative to the control, with TGI at the level of 44.3%. Thus, fusion proteins of the invention exert much stronger effect compared to rhTRAIL114-281 alone.

Mice Crl:SHO-Prkdc$^{scid}$Hr$^{hr}$
HT116 Model

On day 0 mice Crl:SHO-Prkdc$^{scid}$Hr$^{hr}$ were grafted subcutaneously (sc) in the right side with 5×10$^6$ of HCT116 cells suspended in 0.2 ml HBSS buffer by means of a syringe with a 0.5×25 mm needle (Bogmark). When tumors reached the size of ~380-430 mm$^3$ (day 14), mice were randomized to obtain the average size of tumors in the group of ~400 mm$^3$ and assigned to treatment groups. The treatment groups were administered with the preparations of fusion proteins of the invention of Ex. 6 (30 mg/kg), Ex. 11 (45 mg/kg) and rhTRAIL114-281 (20 mg/kg) as a comparison against formulation buffer (5 mM NaH$_2$PO$_4$, 95 mM Na$_2$HPO$_4$, 200 mM NaCl, 5 mM glutatione, 0.1 mM ZnCl$_2$, 10% glycerol, 80 mM saccharose, pH 8.0) as a control. The preparations were administered intravenously (i.v.) six times every second day. When a therapeutic group reached the average tumor size of ~1000 mm$^3$, mice were sacrificed by disruption of the spinal cord. The control group received rhTRAIL114-281.

Figure 12:
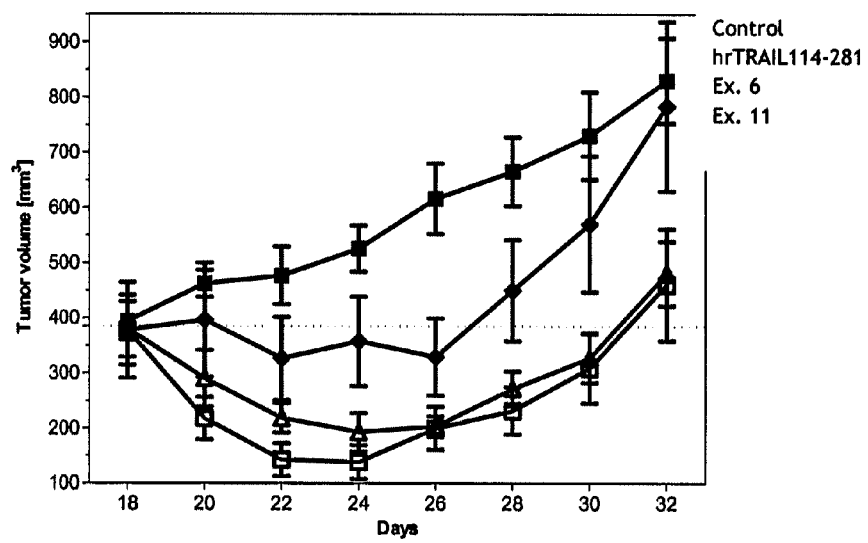
FIG. 12 presents tumor volume changes (% of initial stage) in Crl:SHO-Prkdc$^{scid}$Hr$^{hr}$ mice burdened with colon cancer HCT116 treated with fusion proteins of the invention from Ex. 6 and Ex. 11 compared to rhTRAIL114-281.
Figure 13:
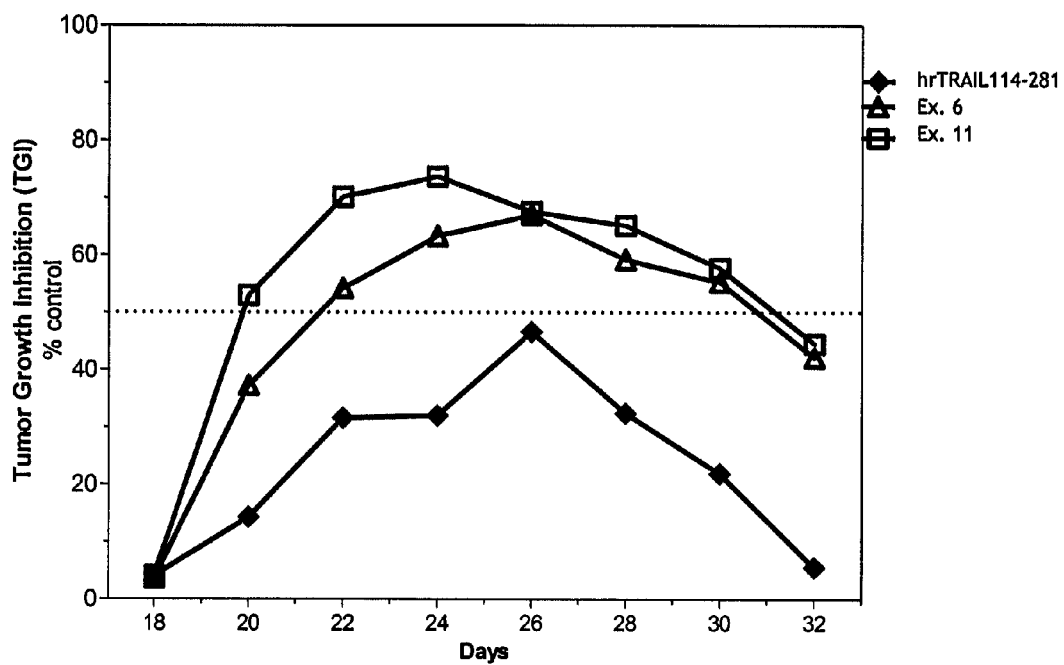
FIG. 13 presents the tumor growth inhibition values (% TGI) in Crl:SHO-Prkdc$^{scid}$Hr$^{hr}$ mice burdened with colon cancer HCT116 treated with fusion proteins of the invention from Ex. 6 and Ex. 11 compared to rhTRAIL114-281.

The experimental results obtained in mice Crl:SHO-Prkdc$^{scid}$Hr$^{hr}$ burdened with HCT116 colon cancer treated with fusion proteins of the invention of Ex. 6 (30 mg/kg), Ex. 11 (45 mg/kg) and comparatively with rhTRAIL114-281 are shown in FIG. 12 as a diagram of changes of the tumor volume and in FIG. 13 which shows tumor growth inhibition (% TGI) as the percentage of control.

The results of experiments presented in the graphs in FIGS. 12 and 13 show that administration of the fusion proteins of the invention of Ex. 6 and Ex. 11 caused tumor HCT116 growth inhibition, with TGI respectively 42% and 44.5% relative to the control on 32$^{nd}$ day of the experiment. For rhTRAIL114-281 used as the comparative reference, a slight inhibitory effect on tumor cell growth was obtained relative to the control, with TGI at the level of 5.6%. Thus, fusion proteins of the invention exert much stronger effect compared to rhTRAIL114-281 alone.

Mice Crl:SHO-Prkdc$^{scid}$Hr$^{hr}$
COLO205 Model

On day 0 mice Crl:SHO-Prkdc$^{scid}$Hr$^{hr}$ were grafted subcutaneously (sc) in the right side with 5×10$^6$ of Colo205 cells suspended in 0.2 ml HBSS buffer by means of a syringe with a 0.5×25 mm needle (Bogmark). When tumors reached the size of ~90-130 mm$^3$ (day 13), mice were randomized to obtain the average size of tumors in the group of ~115 mm$^3$ and assigned to treatment groups. The treatment groups were administered with the preparations of fusion proteins of the invention of Ex. 6 (30 mg/kg), Ex. 19 (30 mg/kg) and rhTRAIL114-281 (30 mg/kg) as a comparison against formulation buffer (5 mM NaH$_2$PO$_4$, 95 mM Na$_2$HPO$_4$, 200 mM NaCl, 5 mM glutatione, 0.1 mM ZnCl$_2$, 10% glycerol, 80 mM saccharose, pH 8.0) as a control. The preparations were administered intravenously (i.v.) six times every second day. When a therapeutic group reached the average tumor size of ~1000 mm$^3$, mice were sacrificed by disruption of the spinal cord. The control group received rhTRAIL114-281.

Figure 14:
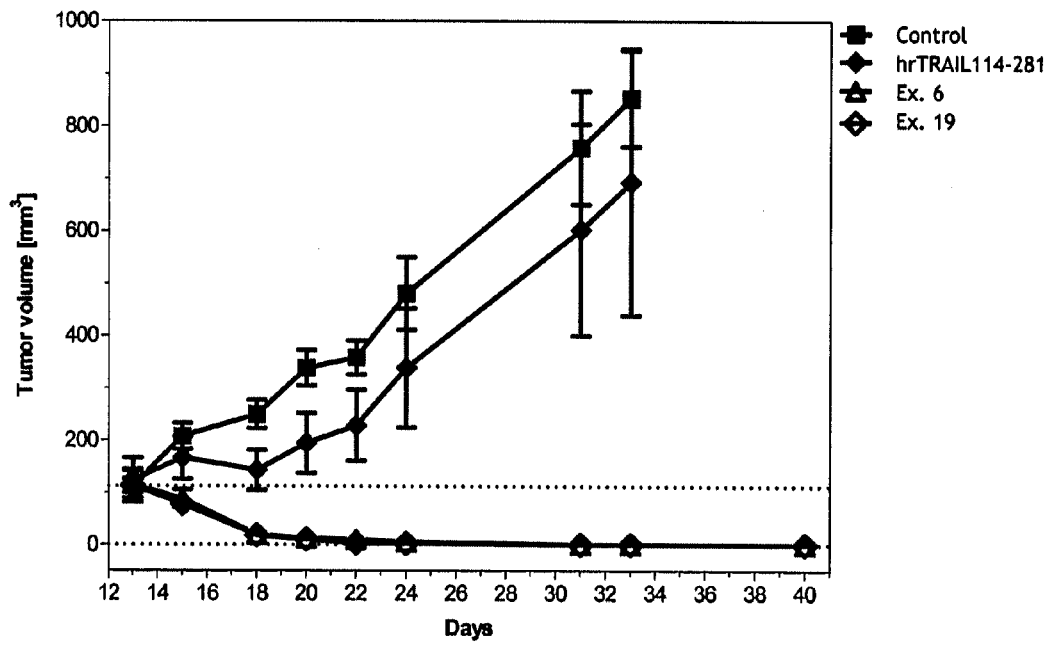
FIG. 14 presents tumor volume changes (% of initial stage) in Crl:SHO-Prkdc$^{scid}$Hr$^{hr}$ mice burdened with colon cancer Colo205 treated with fusion proteins of the invention from Ex. 6 and Ex. 19 compared to rhTRAIL114-281.
Figure 15:
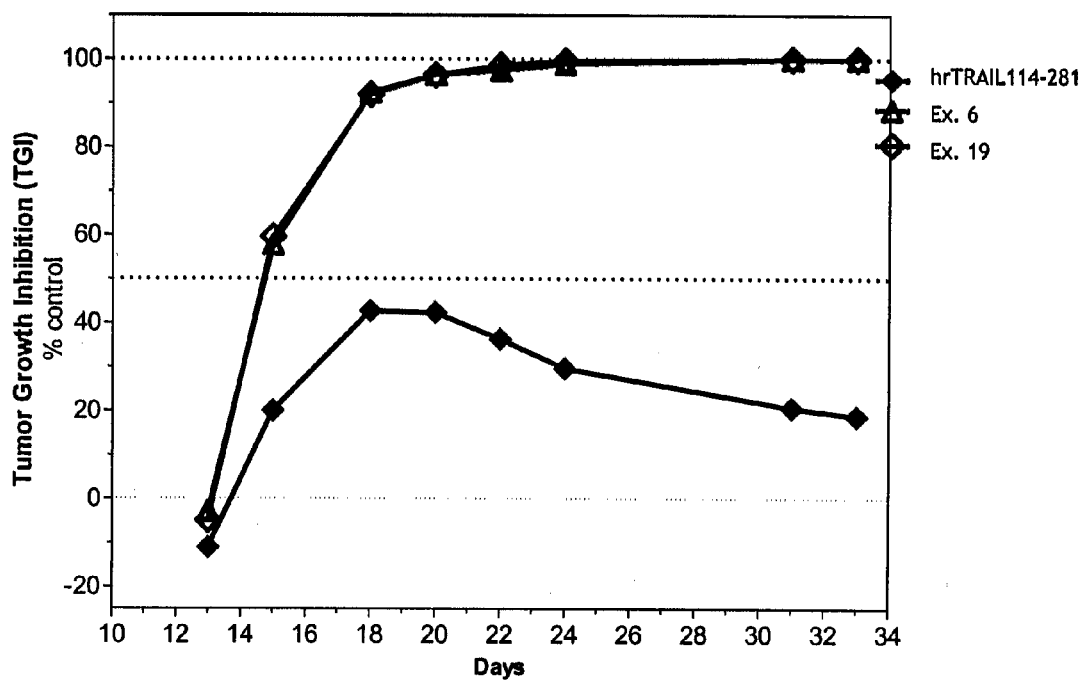
FIG. 15 presents the tumor growth inhibition values (% TGI) in Crl:SHO-Prkdc$^{scid}$Hr$^{hr}$ mice burdened with colon cancer Colo205 treated with fusion proteins of the invention from Ex. 6 and Ex. 19 compared to rhTRAIL114-281.

The experimental results obtained in mice Crl:SHO-Prkdc$^{scid}$Hr$^{hr}$ burdened with Colo205 colon cancer treated with fusion proteins of the invention of Ex. 6 (30 mg/kg), Ex. 19 (45 mg/kg) and comparatively with rhTRAIL114-281 are shown in FIG. 14 as a diagram of changes of the tumor volume and in FIG. 15 which shows tumor growth inhibition (% TGI) as the percentage of control.

The results of experiments presented in the graphs in FIGS. 14 and 15 show that administration of the fusion proteins of the invention of Ex. 6 and Ex. 19 caused tumor Colo205 growth inhibition, with TGI respectively 100% and 100% relative to the control on 33$^{th}$ day of the experiment. For rhTRAIL114-281 used as the comparative reference, a slight inhibitory effect on tumor cell growth was obtained relative to the control, with TGI at the level of 18.8%. Thus, fusion proteins of the invention exert much stronger effect compared to rhTRAIL114-281 alone.

Mice Crl:SHO-Prkdc$^{scid}$Hr$^{hr}$
SW620 Model

On day 0 mice Crl:SHO-Prkdc$^{scid}$Hr$^{hr}$ were grafted subcutaneously (sc) in the right side with 5×10$^6$ of SW620 cells suspended in 0.2 ml HBSS buffer by means of a syringe with a 0.5×25 mm needle (Bogmark). When tumors reached the size of ~290-350 mm$^3$ (day 17), mice were randomized to obtain the average size of tumors in the group of ~320 mm$^3$ and assigned to treatment groups. The treatment groups were administered with the preparations of fusion proteins of the invention of Ex. 6 (30 mg/kg), Ex. 11 (40 mg/kg) and TRAIL114-281 (30 mg/kg) as a comparison against formulation buffer (5 mM NaH$_2$PO$_4$, 95 mM Na$_2$HPO$_4$, 200 mM NaCl, 5 mM glutatione, 0.1 mM ZnCl$_2$, 10% glycerol, 80 mM saccharose, pH 8.0) as a control. The preparations were administered intravenously (i.v.) six times every second day. When a therapeutic group reached the average tumor size of ~1000 mm$^3$, mice were sacrificed by disruption of the spinal cord. The control group received rhTRAIL114-281.

Figure 16:
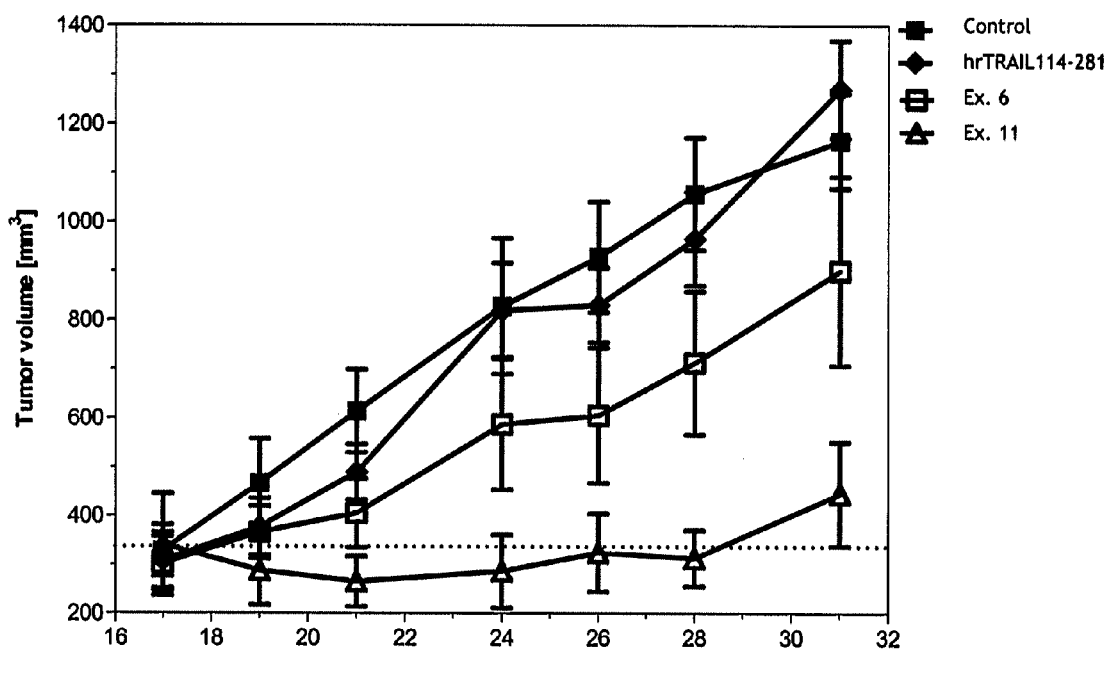
FIG. 16 presents tumor volume changes (% of initial stage) in Crl:SHO-Prkdc$^{scid}$Hr$^{hr}$ mice burdened with colon cancer SW620 treated with fusion proteins of the invention from Ex. 6 and Ex. 11 compared to rhTRAIL114-281.
Figure 17:
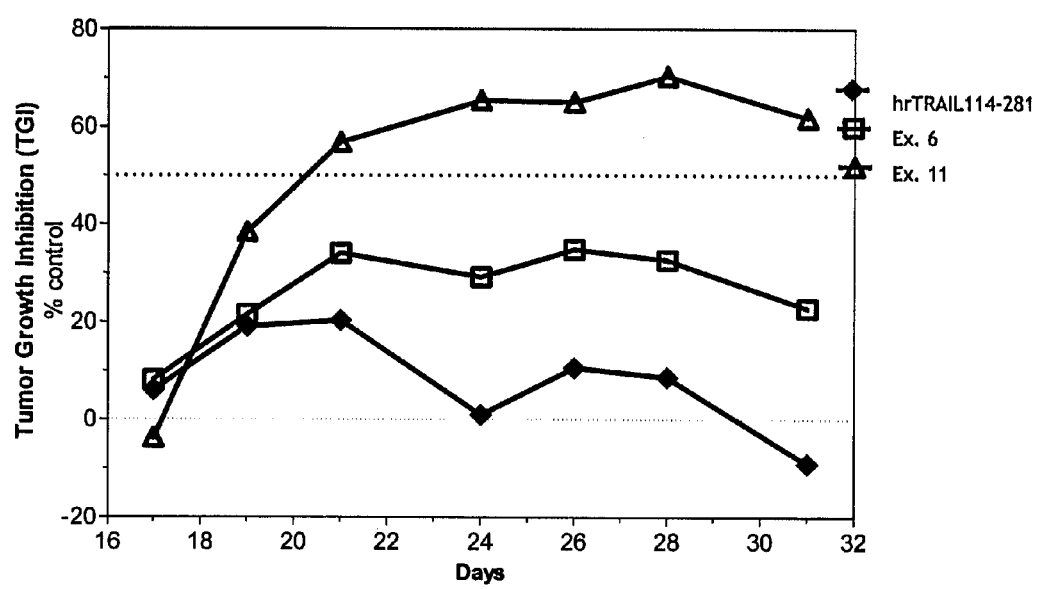
FIG. 17 presents the tumor growth inhibition values (% TGI) in Crl:SHO-Prkdc$^{scid}$Hr$^{hr}$ mice burdened with colon cancer SW620 treated with fusion proteins of the invention from Ex. 6 and Ex. 11 compared to rhTRAIL114-281.

The experimental results obtained in mice Crl:SHO-Prkdc$^{scid}$Hr$^{hr}$ burdened with SW620 colon cancer treated with fusion proteins of the invention of Ex. 6 and Ex. 11 and comparatively with rhTRAIL114-281 are shown in FIG. 16 as a diagram of changes of the tumor volume and in FIG. 17 which shows tumor growth inhibition (% TGI) as the percentage of control.

The results of experiments presented in the graphs in FIGS. 16 and 17 show that administration of the fusion proteins of the invention of Ex. 6 and Ex. 11 caused tumor SW620 growth inhibition, with TGI respectively 62% and 23 relative to the control on 31$^{st}$ day of the experiment. For rhTRAIL114-281 used as the comparative reference, no inhibitory effect on tumor cell growth was obtained relative to the control, with TGI at the level of −9%. Thus, fusion proteins of the invention exert much stronger effect compared to rhTRAIL114-281 alone.

The tested fusion proteins did not cause significant side effects manifested by a decrease in body weight of mice (i.e. less than 10% of the baseline body weight). This shows low systemic toxicity of the protein.

Human Lung Cancer Model
Mice Crl:CD1-Foxn1$^{nu}$ 1

On day 0 mice Crl:CD1-Foxn1$^{nu}$ 1 were grafted subcutaneously (sc) in the right side with 5×10$^6$ of A549 cells suspended in 0.2 ml HBSS buffer by means of a syringe with a 0.5×25 mm needle (Bogmark). When tumors reached the size of ~80-100 mm$^3$ (day 14), mice were randomized to obtain the average size of tumors in the group of ~90 mm$^3$ and assigned to treatment groups. The treatment groups were administered with the preparation of fusion protein of the invention of Ex. 1 (10 mg/kg), and rhTRAIL114-281 (10 mg/kg as a comparison. The preparations were administered intravenously (i.v.) every second day for twelve days. When a therapeutic group reached the average tumor size of ~1000 mm$^3$, mice were sacrificed by disruption of the spinal cord. The control group received rhTRAIL114-281.

Figure 7:
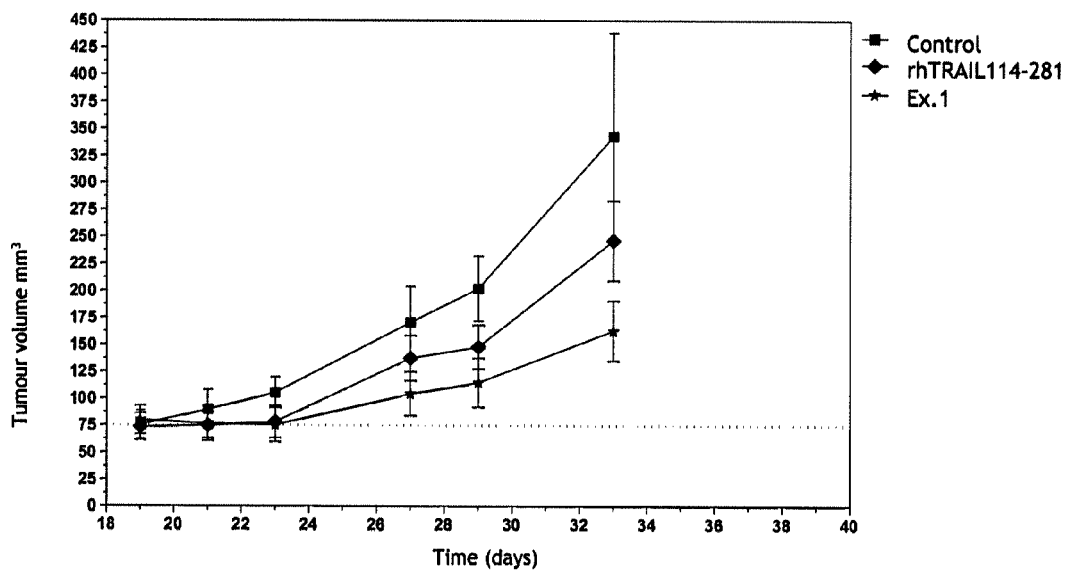
FIG. 7 presents tumor volume changes (% of initial stage) in Crl:CD1-Foxn1nu mice burdened with lung cancer A549 treated with fusion proteins of the invention of Ex. 1 compared to rhTRAIL114-281
Figure 8:
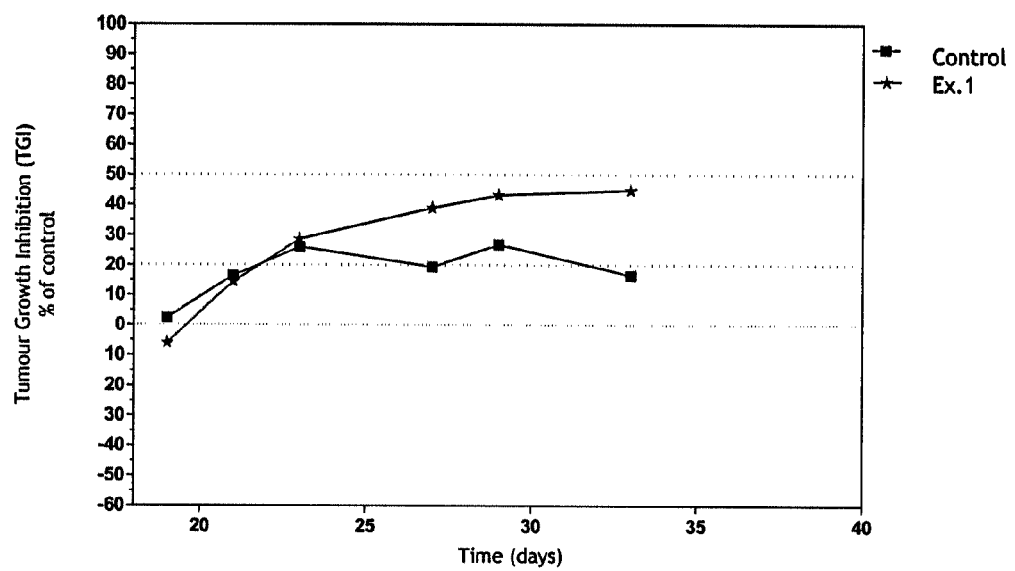
FIG. 8 presents the tumor growth inhibition values (% TGI) in Crl:CD1-Foxn1$^{nu}$ 1 mice burdened with lung cancer A549 treated with fusion proteins of the invention of Ex. 1 compared to rhTRAIL114-281.

The experimental results obtained in mice Crl:CD1-Foxn1$^{nu}$ burdened with A549 lung cancer treated with fusion proteins of the invention of Ex. 1 and comparatively with rhTRAIL114-281 are shown in FIG. 7 as a diagram of changes of the tumor volume and in FIG. 8 which shows tumor growth inhibition (% TGI) as the percentage of control.

The results of experiments presented in the graphs in FIGS. 7 and 8 show that administration of the fusion protein of the invention of Ex. 1 caused tumor A549 growth inhibition, with TGI 44.8% relative to the control on 33$^{th}$ day of the experiment. For rhTRAIL114-281 used as the comparative reference, a slight inhibitory effect on tumor cell growth was obtained relative to the control, with TGI at the level of 16.5%. Thus, fusion proteins of the invention exert much stronger effect compared to TRAIL alone.

Cby.Cg-foxn1(nu)/J

On day 0 mice Cby.Cg-foxn1(nu)/J were grafted subcutaneously (sc) in the right side with 5×10$^6$ of A549 cells suspended in 0.2 ml HBSS buffer by means of a syringe with a 0.5×25 mm needle (Bogmark). When tumors reached the size of ~60-90 mm$^3$ (day 19), mice were randomized to obtain the average size of tumors in the group of ~75 mm$^3$ and assigned to treatment groups. The treatment groups were administered with the preparations of fusion protein of the invention of Ex. 1 (15 mg/kg) and rhTRAIL114-281 (20 mg/kg) as a comparison against water for injection as a control. The preparations were administered intravenously (i.v.) six times every second day. When a therapeutic group reached the average tumor size of 1000 mm$^3$, mice were sacrificed by disruption of the spinal cord. The control group received rhTRAIL114-281.

Figure 18:
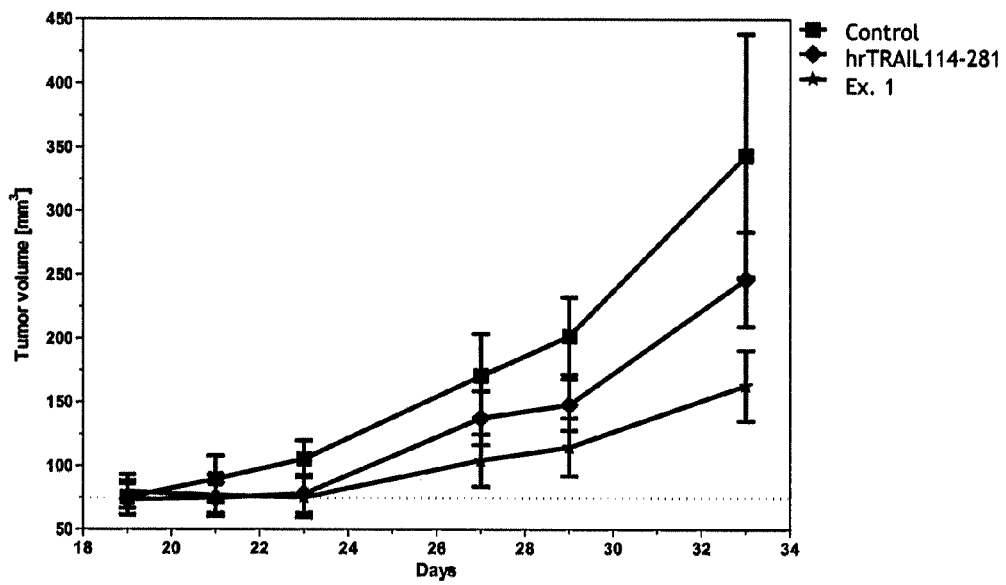
FIG. 18 presents tumor volume changes (% of initial stage) in Cby.Cg-foxn1(nu)/J mice burdened with lung cancer A549 treated with fusion protein of the invention from Ex. 1 compared to rhTRAIL114-281.
Figure 19:
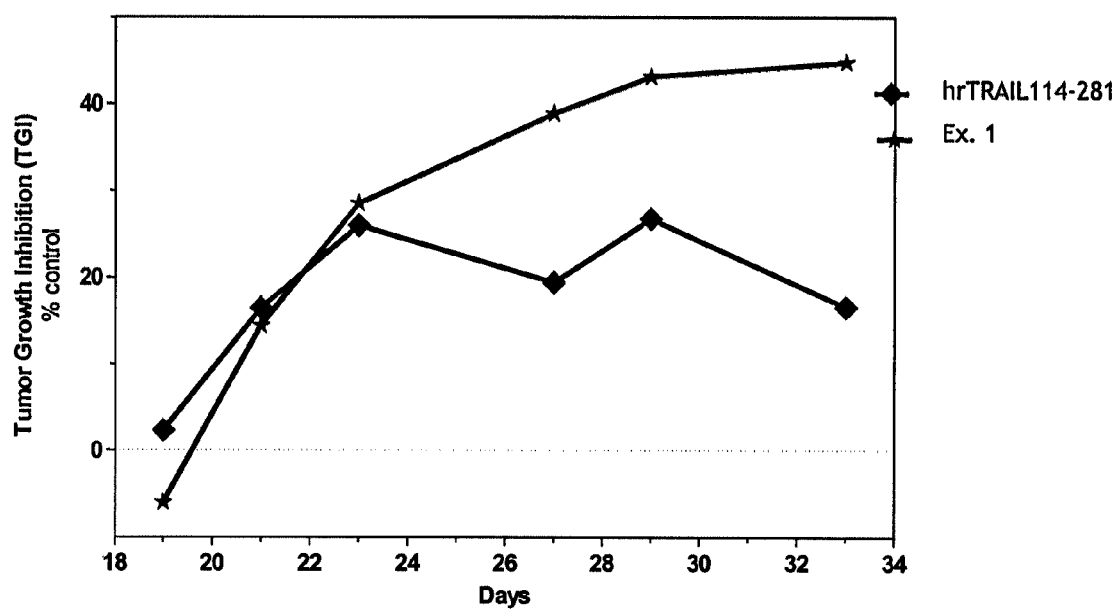
FIG. 19 presents the tumor growth inhibition values (% TGI) in Cby.Cg-foxn1(nu)/J mice burdened with lung cancer A549 treated with fusion protein of the invention from Ex. 1 compared to rhTRAIL114-281.

The experimental results obtained in mice Cby.Cg-foxn1(nu)/J burdened with A549 lung cancer treated with fusion protein of the invention of Ex. 1 and comparatively with rhTRAIL114-281 are shown in FIG. 18 as a diagram of changes of the tumor volume and in FIG. 19 which shows tumor growth inhibition (% TGI) as the percentage of control.

The results of experiments presented in the graphs in FIGS. 18 and 19 show that administration of the fusion protein of the invention Ex. 1 caused tumor A549 growth inhibition, with TGI 44.8% relative to the control on 33$^{th}$ day of the experiment. For rhTRAIL114-281 used as the comparative reference, a slight inhibitory effect on tumor cell growth was obtained relative to the control, with TGI at the level of 16.6%. Thus, fusion proteins of the invention exert much stronger effect compared to rhTRAIL114-281 alone.

Mice: Crl:SHO-Prkdc$^{scid}$Hr$^{hr}$

A. On day 0 mice Crl:SHO-Prkdc$^{scid}$Hr$^{hr}$ were grafted subcutaneously (sc) in the right side with 5×10$^6$ of NCI-H460 cells suspended in 0.2 ml HBSS buffer by means of a syringe with a 0.5×25 mm needle (Bogmark). When tumors reached the size of ~150-170 mm$^3$ (day 13), mice were randomized to obtain the average size of tumors in the group of ~160 mm$^3$ and assigned to treatment groups. The treatment groups were administered with the preparations of fusion protein of the invention of Ex. 6 (30 mg/kg) and rhTRAIL114-281 (30 mg/kg) as a comparison against against formulation buffer (5 mM NaH$_2$PO$_4$, 95 mM Na$_2$HPO$_4$, 200 mM NaCl, 5 mM glutatione, 0.1 mM ZnCl$_2$, 10% glycerol, 80 mM saccharose, pH 8.0) as a control. The preparations were administered intravenously (i.v.) six times every second day. When a therapeutic group reached the average tumor size of ~1000 mm$^3$, mice were sacrificed by disruption of the spinal cord. The control group received rhTRAIL114-281.

Figure 20:
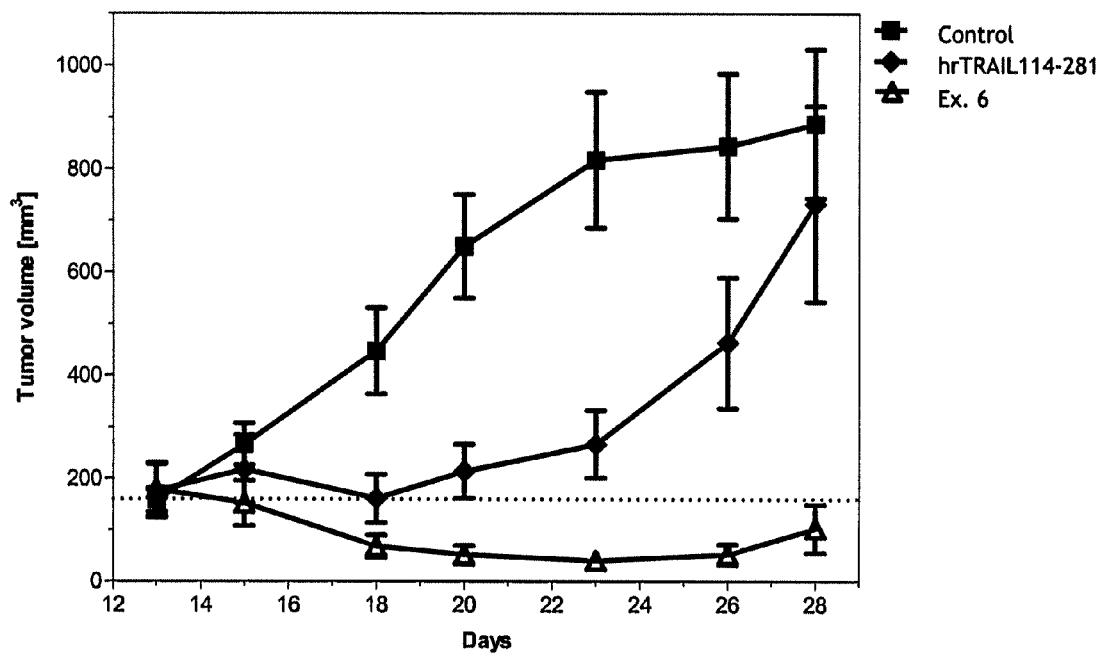
FIG. 20 presents tumor volume changes (% of initial stage) in Crl:SHO-Prkdc$^{scid}$Hr$^{hr}$ mice burdened with lung cancer NCI-H1460 treated with fusion protein of the invention from Ex. 6 compared to rhTRAIL114-281.
Figure 21:
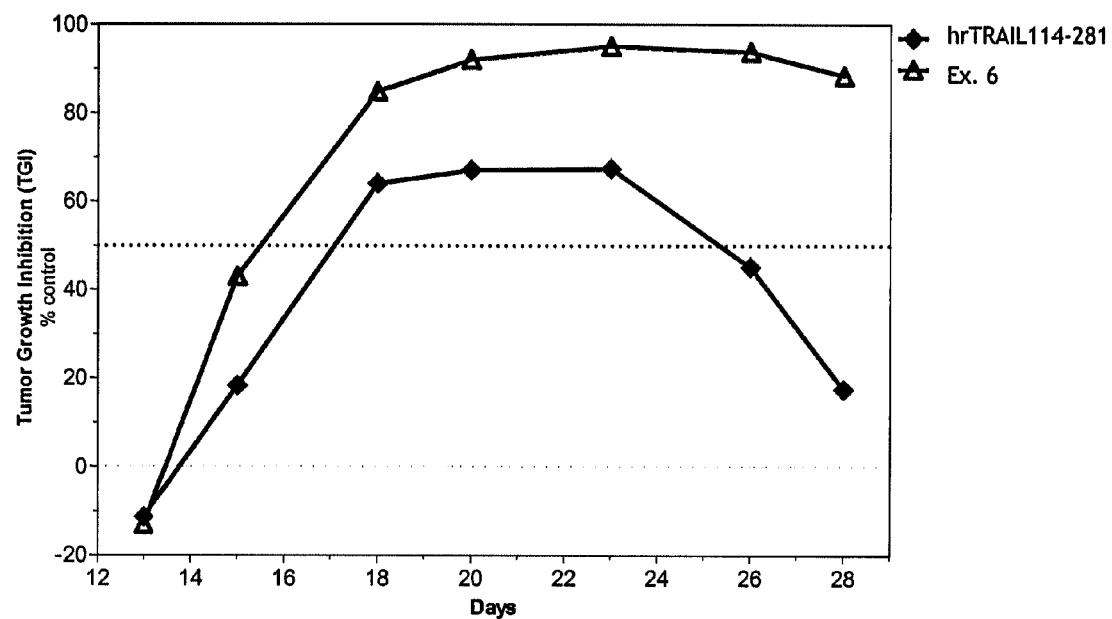
FIG. 21 presents the tumor growth inhibition values (% TGI) in Crl:SHO-Prkdc$^{scid}$Hr$^{hr}$ mice burdened with lung cancer NCI-H460 treated with fusion protein of the invention from Ex. 6 compared to rhTRAIL114-281.

The experimental results obtained in mice Crl:SHO-Prkdc$^{scid}$Hr$^{hr}$ burdened with NCI-H460 lung cancer treated with fusion protein of the invention of Ex. 6 and comparatively with rhTRAIL114-281 are shown in FIG. 20 as a diagram of changes of the tumor volume and in FIG. 21 which shows tumor growth inhibition (% TGI) as the percentage of control.

The results of experiments presented in the graphs in FIGS. 20 and 21 show that administration of the fusion protein of the invention Ex. 6 caused tumor NCI-H460 growth inhibition, with TGI 88.5% relative to the control on 28$^{th}$ day of the experiment. For rhTRAIL114-281 used as the comparative reference, a slight inhibitory effect on tumor cell growth was obtained relative to the control, with TGI at the level of 17.5%. Thus, fusion proteins of the invention exert much stronger effect compared to rhTRAIL114-281 alone.

B. On day 0 mice Crl:SHO-Prkdc$^{scid}$Hr$^{hr}$ were grafted subcutaneously (sc) in the right side with 7×10$^6$ of A549 cells suspended in a mixture of 0.2 ml HBSS:Matrigel in ratio 3:1 by means of a syringe with a 0.5×25 mm needle (Bogmark). When tumors reached the size of ~140-165 mm$^3$ (day 19), mice were randomized to obtain the average size of tumors in the group of ~150 mm$^3$ and assigned to treatment groups. The treatment groups were administered with the preparations of fusion proteins of the invention of Ex. 5 (60 mg/kg), Ex. 6 (50 mg/kg), Ex. 11 (50 mg/kg) and rhTRAIL114-281 (20 mg/kg) as a comparison against against formulation buffer (5 mM NaH$_2$PO$_4$, 95 mM Na$_2$HPO$_4$, 200 mM NaCl, 5 mM glutatione, 0.1 mM ZnCl$_2$, 100 mM L-arginine, 80 mM sacharose, pH 8.0) as a control. The preparations were administered intravenously (i.v.) six times every second day. When a therapeutic group reached the average tumor size of ~1000 mm$^3$, mice were sacrificed by disruption of the spinal cord. The control group received rhTRAIL114-281.

Figure 22:
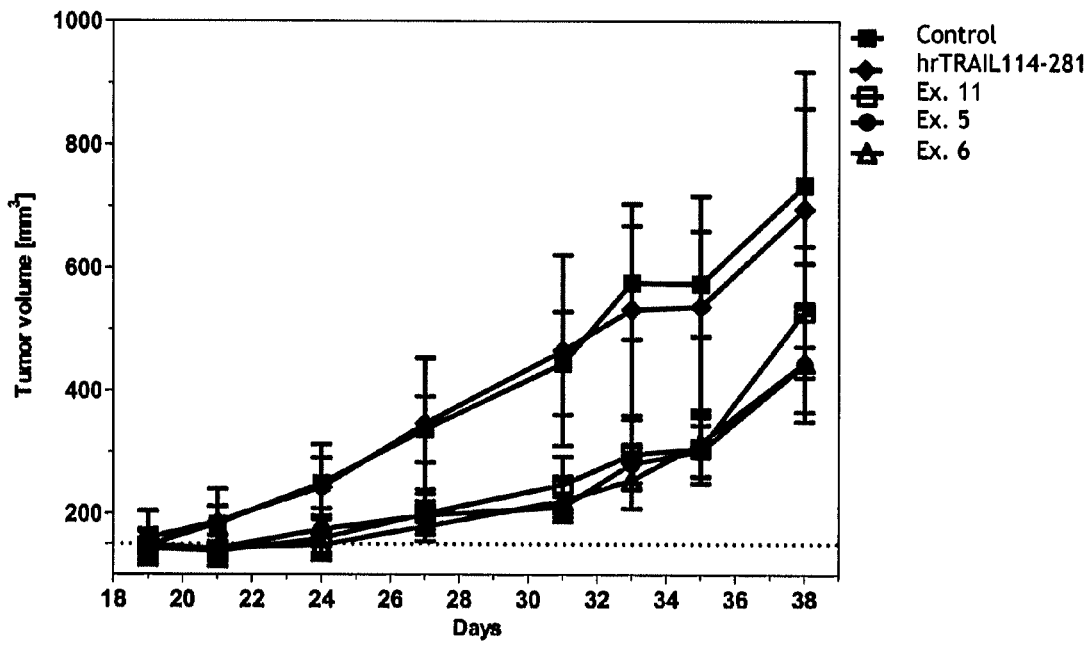
FIG. 22 presents tumor volume changes (% of initial stage) in Crl:SHO-Prkdc$^{scid}$Hr$^{hr}$ mice burdened with lung cancer A549 treated with fusion protein of the invention from Ex. 5, Ex. 6, Ex. 11 compared to rhTRAIL114-281.
Figure 23:
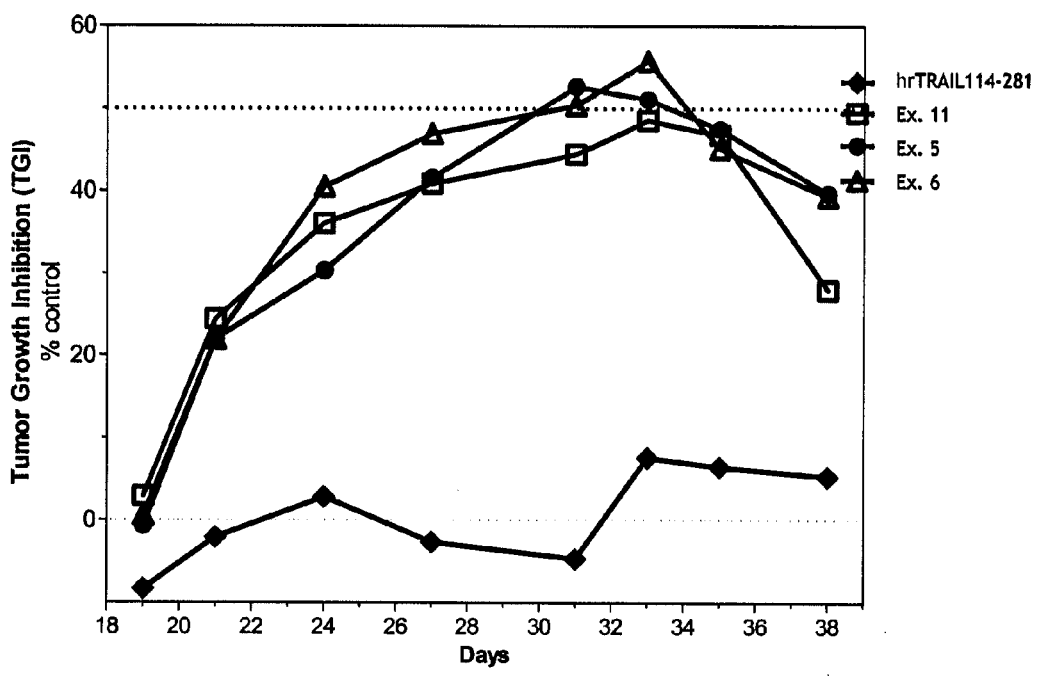
FIG. 23 presents the tumor growth inhibition values (% TGI) in Crl:SHO-Prkdc$^{scid}$Hr$^{hr}$ mice burdened with lung cancer A549 treated with fusion protein of the invention from Ex. 5, Ex. 6, Ex. 11 compared to rhTRAIL114-281.

The experimental results obtained in mice Crl:SHO-Prkdc$^{scid}$Hr$^{hr}$ burdened with A549 lung cancer treated with fusion proteins of the invention of Ex. 5, Ex. 6, 11 and comparatively with rhTRAIL114-281 are shown in FIG. 22 as a diagram of changes of the tumor volume and in FIG. 23 which shows tumor growth inhibition (% TGI) as the percentage of control.

The results of experiments presented in the graphs in FIGS. 22 and 23 show that administration of the fusion proteins of the invention Ex. 5, Ex. 6, and Ex. 11 caused tumor A549 growth inhibition, with TGI respectively 39.3%, 39.3% and 28% relative to the control on 38$^{th}$ day of the experiment. For rhTRAIL114-281 used as the comparative reference, a slight inhibitory effect on tumor cell growth was obtained relative to the control, with TGI at the level of 5.3%. Thus, fusion proteins of the invention exert much stronger effect compared to rhTRAIL114-281 alone.

C. On day 0 mice Crl:SHO-Prkdc$^{scid}$Hr$^{hr}$ were grafted subcutaneously (sc) in the right side with 7×10$^6$ of NCI-H460-Luc2 cells suspended in 0.1 ml HBSS by means of a syringe with a 0.5×25 mm needle (Bogmark). When tumors reached the size of ~100-120 mm³ (day 19), mice were randomized to obtain the average size of tumors in the group of ~110 mm³ and assigned to treatment groups. The treatment groups were administered with the preparations of fusion protein of the invention of Ex. 5 (first administration 40 mg/kg, followed by 30 mg/kg), and rhTRAIL114-281 (20 mg/kg) as a comparison against against formulation buffer (19 mM $NaH_2PO_4$, 81 mM $Na_2HPO_4$, 50 mM NaCl, 5 mM glutation, 0.1 mM $ZnCl_2$, 10% glycerol, pH 7.4) as a control. The preparations were administered intravenously (i.v.) six times every second day. When a therapeutic group reached the average tumor size of ~1000 mm³, mice were sacrificed by disruption of the spinal cord. The control group received rhTRAIL114-281.

Figure 24:
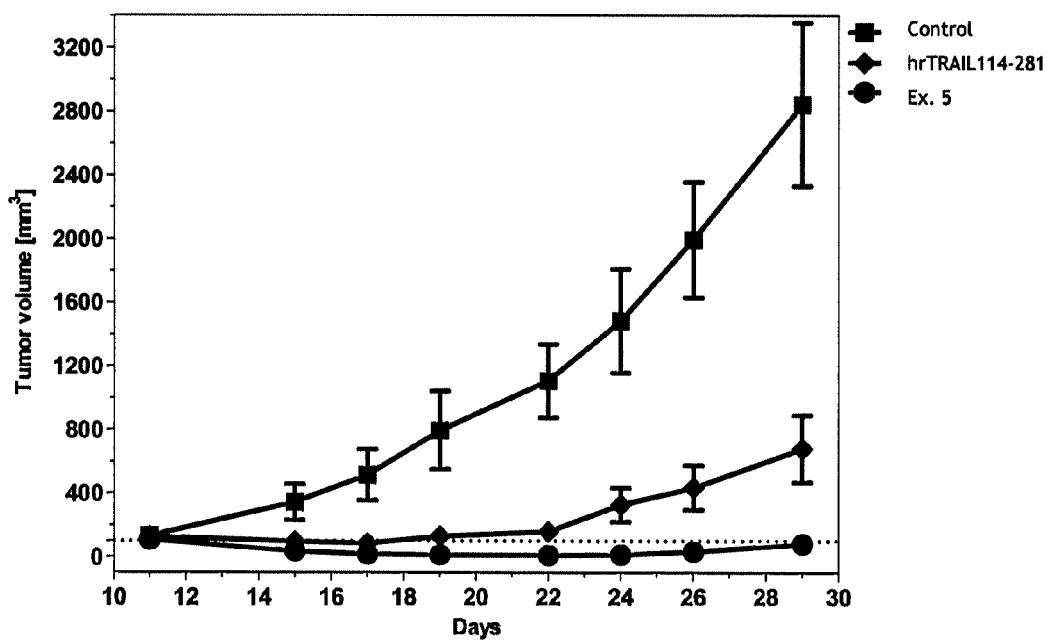
FIG. 24 presents tumor volume changes (% of initial stage) in Crl:SHO-Prkdc$^{scid}$Hr$^{hr}$ mice burdened with lung cancer NCI-H460-Luc2 treated with fusion protein of the invention from Ex. 5 compared to rhTRAIL114-281.
Figure 25:
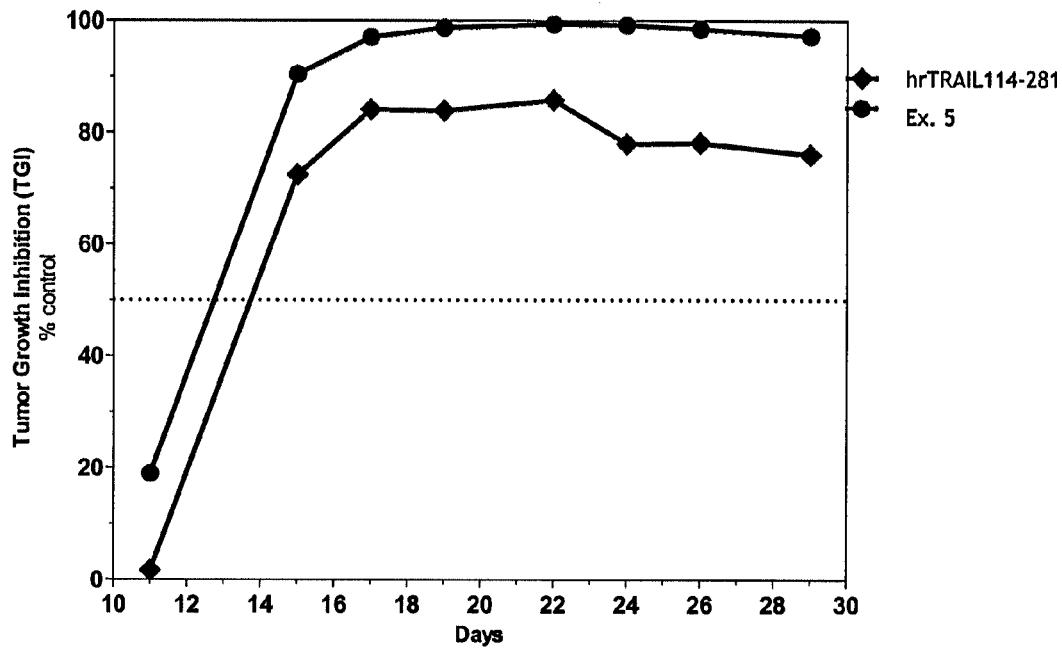
FIG. 25 presents the tumor growth inhibition values (% TGI) in Crl:SHO-Prkdc$^{scid}$Hr$^{hr}$ mice burdened with lung cancer NCI-H460-Luc2 treated with fusion protein of the invention from Ex. 5 compared to rhTRAIL114-281.

The experimental results obtained in mice Crl:SHO-Prkdc$^{scid}$Hr$^{hr}$ burdened with NCI-H460-Luc2 lung cancer treated with fusion protein of the invention of Ex. 5 and comparatively with rhTRAIL114-281 are shown in FIG. 24 as a diagram of changes of the tumor volume and in FIG. 25 which shows tumor growth inhibition (% TGI) as the percentage of control.

The results of experiments presented in the graphs in FIGS. 24 and 25 show that administration of the fusion protein of the invention of Ex. 5 caused tumor NCI-H460-Luc2 growth inhibition, with TGI 97.2% relative to the control on 29$^{th}$ day of the experiment. For rhTRAIL114-281 used as the comparative reference, a slight inhibitory effect on tumor cell growth was obtained relative to the control, with TGI at the level of 76%. Thus, fusion proteins of the invention exert much stronger effect compared to rhTRAIL114-281 alone.

D. On day 0 mice Crl:SHO-Prkdc$^{scid}$Hr$^{hr}$ were grafted subcutaneously (sc) in the right side with 7×10⁶ of A549 cells suspended in 0.1 ml mixture of HBSS:Matrigel by means of a syringe with a 0.5×25 mm needle (Bogmark). When tumors reached the size of 100-120 mm³ (day 17), mice were randomized to obtain the average size of tumors in the group of ~110 mm³ and assigned to treatment groups. The treatment groups were administered with the preparations of fusion proteins of the invention of Ex. 5 (50 mg/kg), Ex. 1 (50 mg/kg), and rhTRAIL114-281 (20 mg/kg) as a comparison against against formulation buffer (19 mM $NaH_2PO_4$, 81 mM $Na_2HPO_4$, 50 mM NaCl, 5 mM glutation, 0.1 mM $ZnCl_2$, 10% glycerol, pH 7.4) as a control. The preparations were administered intravenously (i.v.) six times every second day. When a therapeutic group reached the average tumor size of ~1000 mm³, mice were sacrificed by disruption of the spinal cord. The control group received rhTRAIL114-281.

Figure 26:
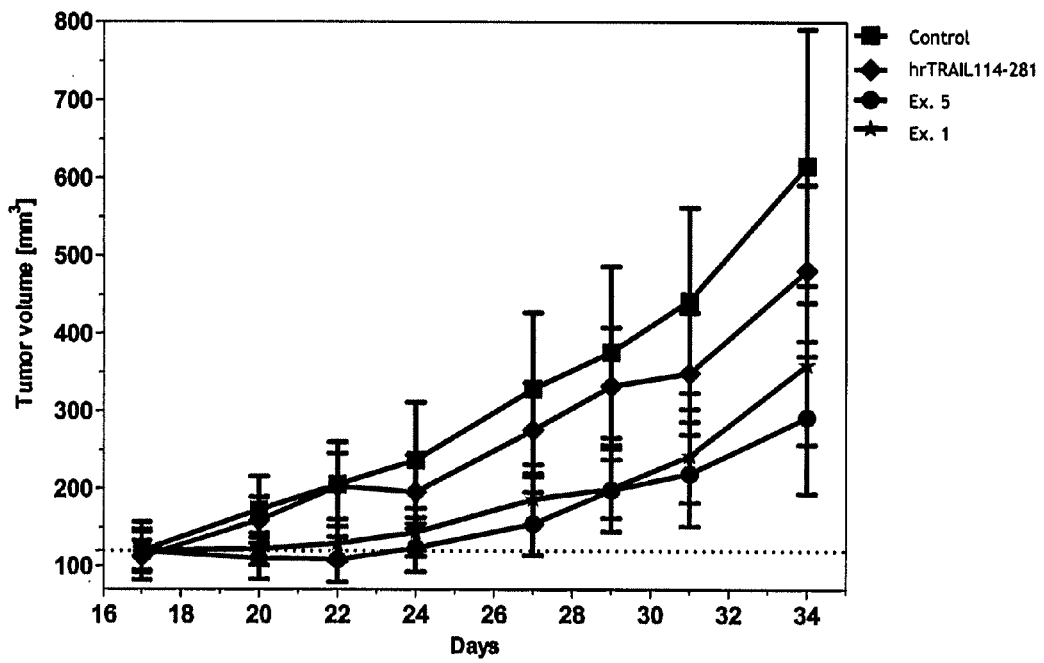
FIG. 26 presents tumor volume changes (% of initial stage) in Crl:SHO-Prkdc$^{scid}$Hr$^{hr}$ mice burdened with lung cancer A549 treated with fusion proteins of the invention from Ex. 5 and Ex. 1 compared to rhTRAIL114-281.
Figure 27:
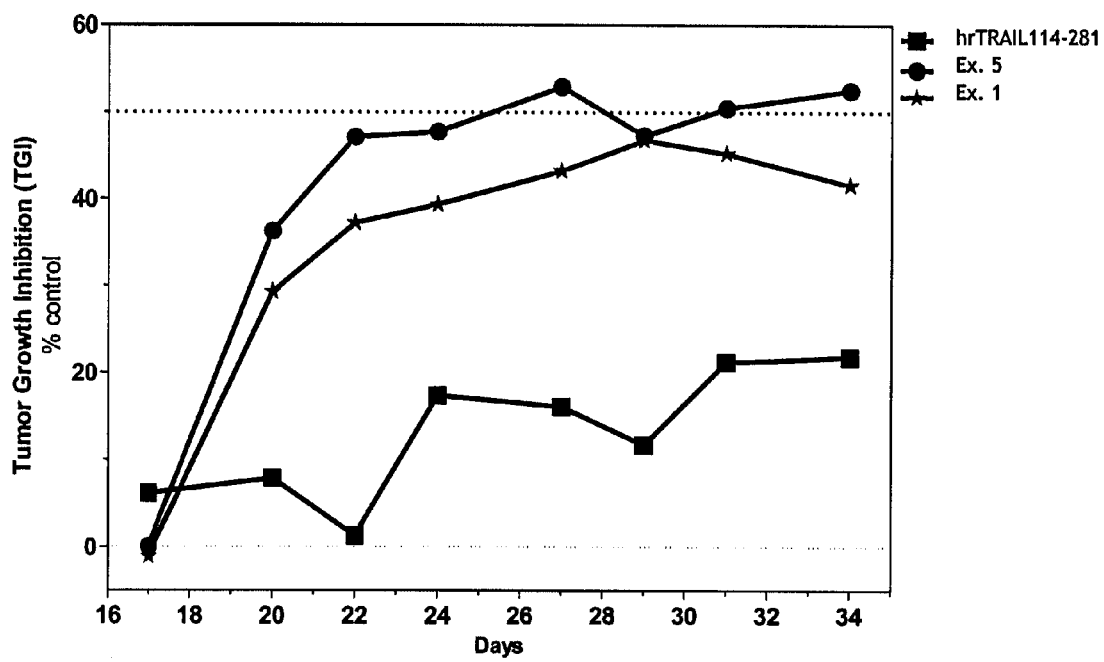
FIG. 27 presents the tumor growth inhibition values (% TGI) in Crl:SHO-Prkdc$^{scid}$Hr$^{hr}$ mice burdened with lung cancer A549 treated with fusion proteins of the invention from Ex. 5 and Ex. 1 compared to rhTRAIL114-281.

The experimental results obtained in mice Crl:SHO-Prkdc$^{scid}$Hr$^{hr}$ burdened with A549 lung cancer treated with fusion proteins of the invention of Ex. 5, Ex. 1 and comparatively with rhTRAIL114-281 are shown in FIG. 26 as a diagram of changes of the tumor volume and in FIG. 27 which shows tumor growth inhibition (% TGI) as the percentage of control.

The results of experiments presented in the graphs in FIGS. 26 and 27 show that administration of the fusion proteins of the invention of Ex. 5 and Ex. 1 caused tumor A549 growth inhibition, with TGI respectively 52.5% and 41.6% relative to the control on 34$^{th}$ day of the experiment. For rhTRAIL114-281 used as the comparative reference, a slight inhibitory effect on tumor cell growth was obtained relative to the control, with TGI at the level of 21.8%. Thus, fusion proteins of the invention exert much stronger effect compared to rhTRAIL114-281 alone.

Liver Cancer Model
Mice Crl:SHO-Prkdc$^{scid}$Hr$^{hr}$

A. On day 0 mice Crl:SHO-Prkdc$^{scid}$Hr$^{hr}$ were grafted subcutaneously (sc) in the right side with 5×10⁶ of PLC/PRF/5 cells suspended in 0.2 ml HBSS buffer by means of a syringe with a 0.5×25 mm needle (Bogmark). When tumors reached the size of 190-220 mm³ (day 31), mice were randomized to obtain the average size of tumors in the group of ~200 mm³ and assigned to treatment groups. The treatment groups were administered with the preparations of fusion protein of the invention of Ex. 6 (40 mg/kg) and Ex. 11 (50 mg/kg), and rhTRAIL114-281 (30 mg/kg) as a comparison against formulation buffer (5 mM $NaH_2PO_4$, 95 mM $Na_2HPO_4$, 200 mM NaCl, 5 mM glutatione, 0.1 mM $ZnCl_2$, 10% glycerol, 80 mM saccharose, pH 8.0) as a control. The preparations were administered intravenously (i.v.) following the schema: 4 administration every third day and 2 administrations every second day. When a therapeutic group reached the average tumor size of ~1000 mm³, mice were sacrificed by disruption of the spinal cord. The control group received rhTRAIL114-281.

Figure 28:
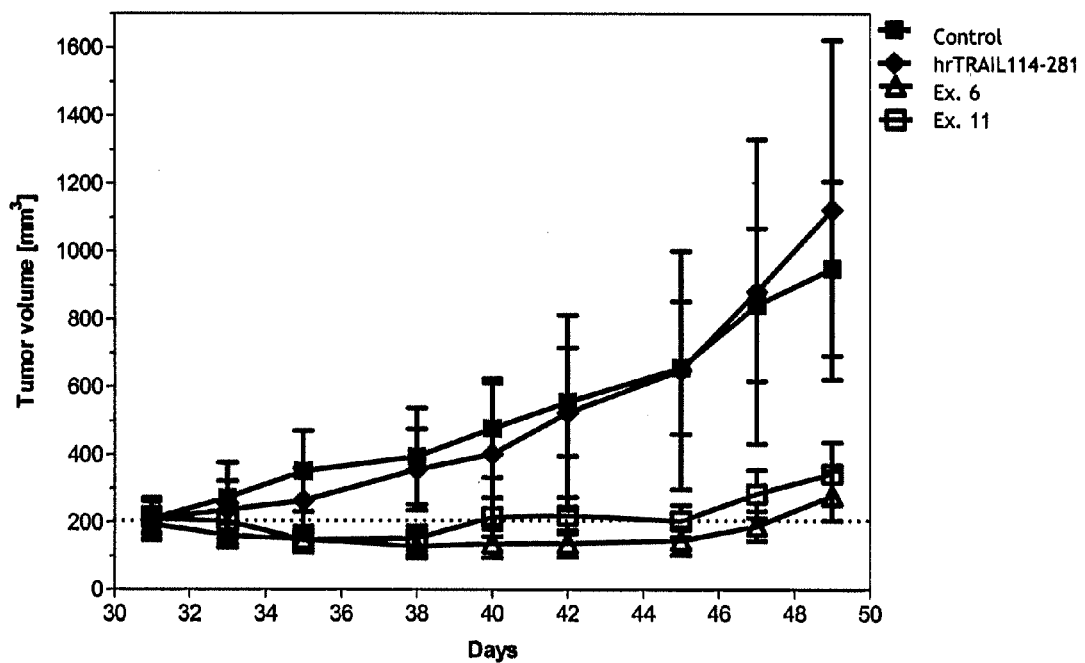
FIG. 28 presents tumor volume changes (% of initial stage) in Crl:SHO-Prkdc$^{scid}$Hr$^{hr}$ mice burdened with liver cancer PLC/PRF/5 treated with fusion proteins of the invention from Ex. 6 and Ex. 11 compared to rhTRAIL114-281.
Figure 29:
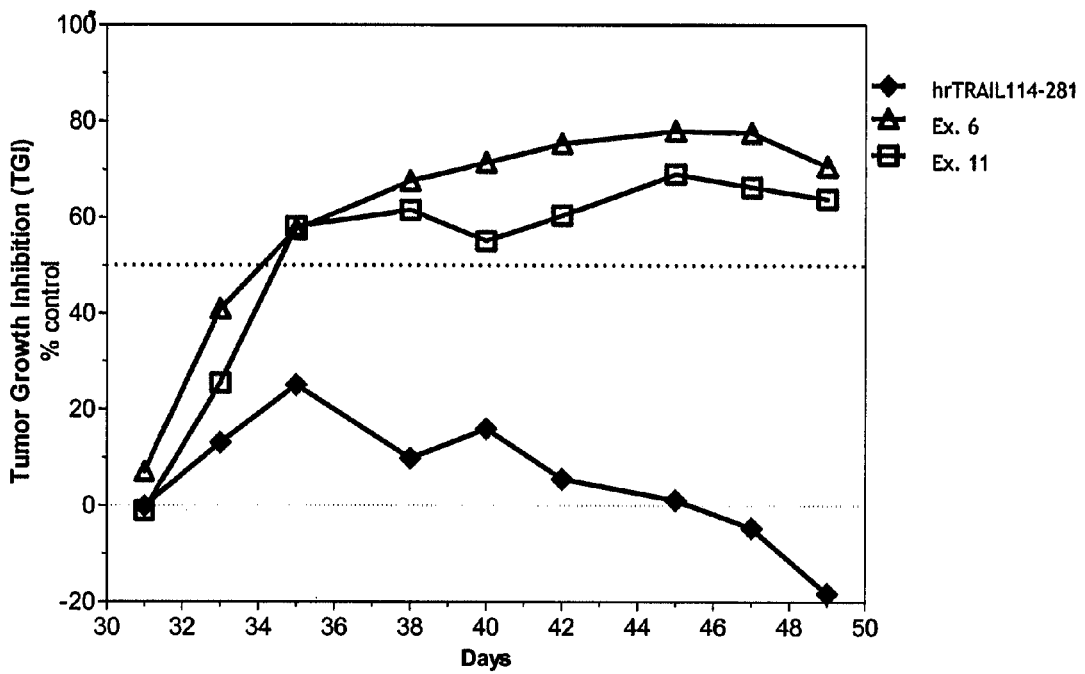
FIG. 29 presents the tumor growth inhibition values (% TGI) in Crl:SHO-Prkdc$^{scid}$Hr$^{hr}$ mice burdened with liver cancer PLC/PRF/5 treated with fusion proteins of the invention from Ex. 6 and Ex. 11 compared to rhTRAIL114-281.

The experimental results obtained in mice Crl:SHO-Prkdc$^{scid}$Hr$^{hr}$ burdened with PLC/PRF/5 liver cancer treated with fusion proteins of the invention of Ex. 6 and Ex. 11 and comparatively with rhTRAIL114-281 are shown in FIG. 28 as a diagram of changes of the tumor volume and in FIG. 29 which shows tumor growth inhibition (% TGI) as the percentage of control.

The results of experiments presented in the graphs in FIGS. 28 and 29 show that administration of the fusion proteins of the invention Ex. 6 and Ex. 11 caused tumor PLC/PRF/5 growth inhibition, with TGI respectively 70.6% and 63.8% relative to the control on 49$^{th}$ day of the experiment. For rhTRAIL114-281 used as the comparative reference, the inhibitory effect on tumor cell growth was not obtained relative to the control, with TGI at the level of ~18%. Thus, fusion proteins of the invention exert much stronger effect compared to rhTRAIL114-281 alone.

Mice Crl:SHO-Prkdc$^{scid}$Hr$^{hr}$

A. On day 0 mice Crl:SHO-Prkdc$^{scid}$Hr$^{hr}$ were grafted subcutaneously (sc) in the right side with 5×10⁶ of HepG2 cells suspended in 0.2 ml HBSS buffer by means of a syringe with a 0.5×25 mm needle (Bogmark). When tumors reached the size of ~190-220 mm³ (day 31), mice were randomized to obtain the average size of tumors in the group of ~200 mm³ and assigned to treatment groups. The treatment groups were administered with the preparations of fusion protein of the invention of Ex. 6 (30 mg/kg), Ex. 19 (30 mg/kg) and rhTRAIL114-281 (30 mg/kg) as a comparison against formulation buffer (5 mM $NaH_2PO_4$, 95 mM $Na_2HPO_4$, 200 mM NaCl, 5 mM glutatione, 0.1 mM $ZnCl_3$, 10% glycerol, 80 mM saccharose, pH 8.0) as a control. The preparations were administered intravenously (i.v.) six times every second day. When a therapeutic group reached the average tumor size of ~1000 mm³, mice were sacrificed by disruption of the spinal cord. The control group received rhTRAIL114-281.

Figure 30:
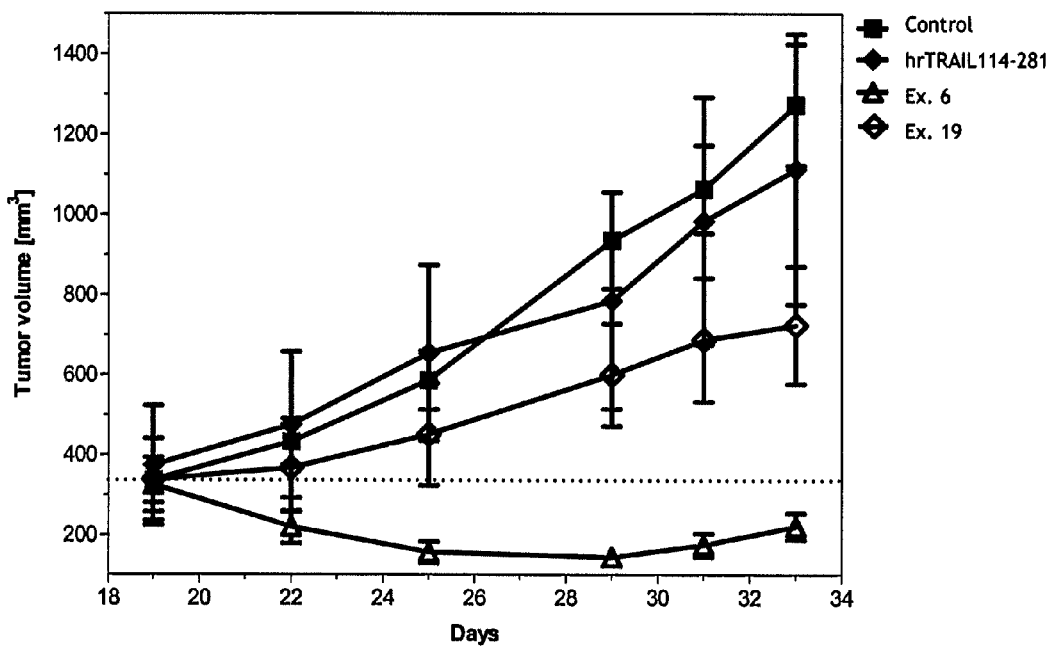
FIG. 30 presents tumor volume changes (% of initial stage) in Ca:SHO-Prkdc$^{scid}$Hr$^{hr}$ mice burdened with HepG2 liver cancer treated with fusion proteins of the invention from Ex. 6 and Ex. 19 compared to rhTRAIL114-281
Figure 31:
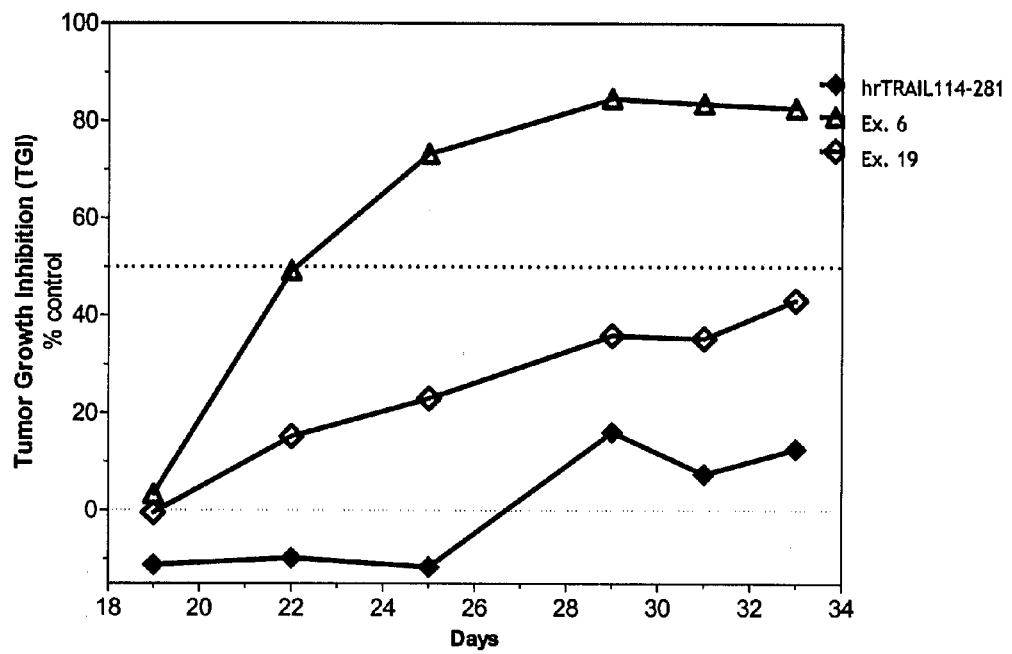
FIG. 31 presents the tumor growth inhibition values (% TGI) in Crl:SHO-Prkdc$^{scid}$Hr$^{hr}$ mice burdened with HepG2 liver cancer treated with fusion proteins of the invention from Ex. 6 and Ex. 19 compared to rhTRAIL114-281.

The experimental results obtained in mice Crl:SHO-Prkdc$^{scid}$Hr$^{hr}$ burdened with HepG2 liver cancer treated with fusion proteins of the invention of Ex. 6, Ex. 19 and comparatively with rhTRAIL114-281 are shown in FIG. 30 as a diagram of changes of the tumor volume and in FIG. 31 which shows tumor growth inhibition (% TGI) as the percentage of control.

The results of experiments presented in the graphs in FIGS. 30 and 31 show that administration of the fusion proteins of the invention Ex. 6 and Ex. 19 caused tumor HepG2 growth inhibition, with TGI respectively 82.6% and 43% relative to the control on 33th day of the experiment. For rhTRAIL114-281 used as the comparative reference, the slight inhibitory effect on tumor cell growth was obtained relative to the control, with TGI at the level of 12.6%. Thus, fusion proteins of the invention exert much stronger effect compared to rhTRAIL114-281 alone.

Pancreas Cancer Model

On day 0 mice Crl:SHO-Prkdc$^{scid}$Hr$^{hr}$ were grafted subcutaneously (sc) in the right side with 7×10$^6$ of PANC1 cells suspended in 0.1 ml of HBSS:Matrigel 3:1 mixture by means of a syringe with a 0.5×25 mm needle (Bogmark). When tumors reached the size of ~87-110 mm$^3$ (day 27), mice were randomized to obtain the average size of tumors in the group of ~95 mm$^3$ and assigned to treatment groups. The treatment groups were administered with the preparation of fusion protein of the invention of Ex. 11 (50 mg/kg) and rhTRAIL114-281 (20 mg/kg) as a comparison against formulation buffer (5 mM NaH$_2$PO$_4$, 95 mM Na$_2$HPO$_4$, 200 mM NaCl, 5 mM glutation, 0.1 mM ZnCl$_2$, 100 mM L-arginine, 80 mM saccharose, pH 8.0) as a control. The preparations were administered intravenously (i.v.) six times every second day. When a therapeutic group reached the average tumor size of ~1000 mm$^3$, mice were sacrificed by disruption of the spinal cord. The control group received rhTRAIL114-281.

Figure 32:
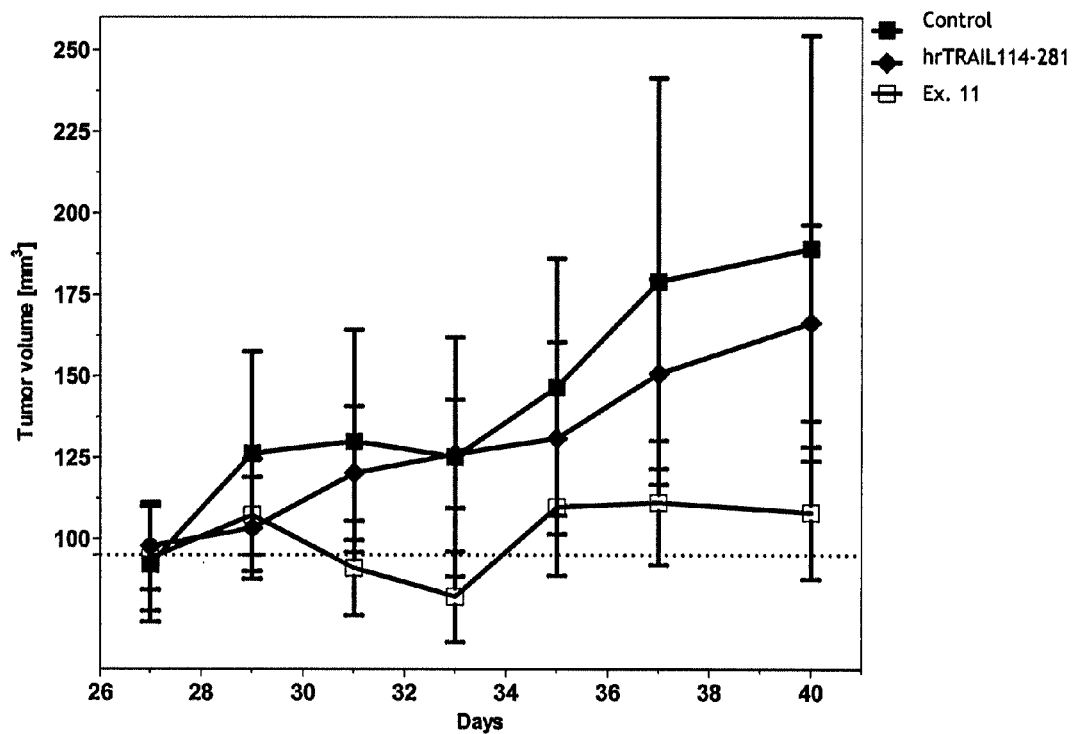
FIG. 32 presents tumor volume changes (% of initial stage) in Crl:SHO-Prkdc$^{scid}$Hr$^{hr}$ mice burdened with PANC-1 pancreas cancer treated with fusion protein of the invention from Ex. 11 compared to rhTRAIL114-281
Figure 33:
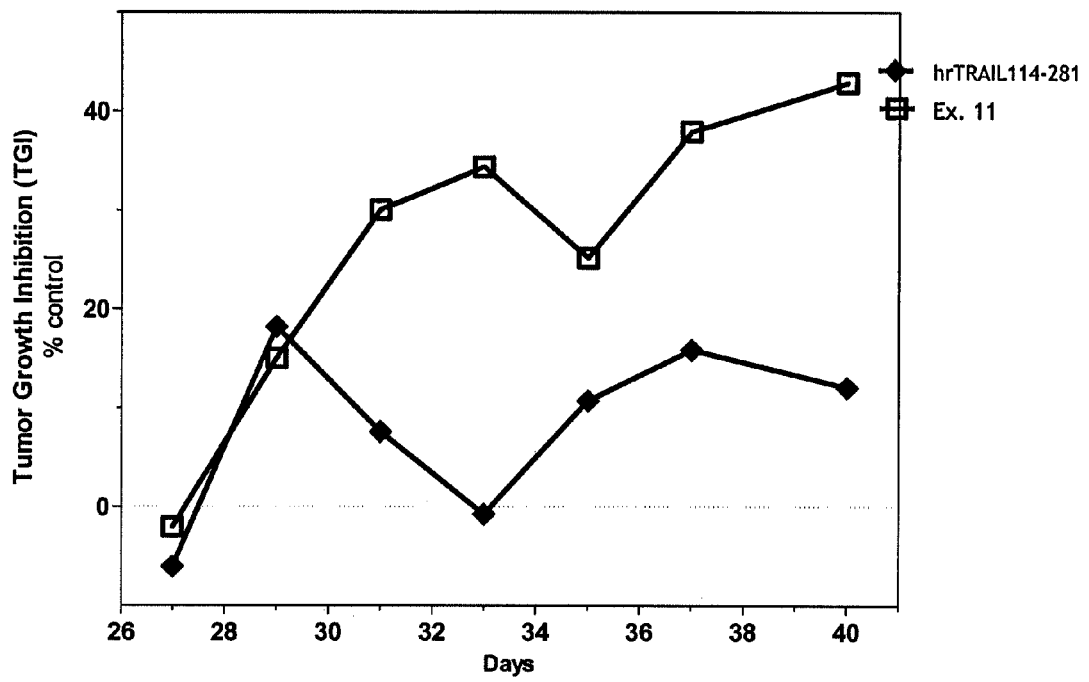
FIG. 33 presents the tumor growth inhibition values (% T61) in Crl:SHO-Prkdc$^{scid}$Hr$^{hr}$ mice burdened with PANC-1 pancreas cancer treated with fusion protein of the invention from Ex. 11 compared to rhTRAIL114-281.

The experimental results obtained in mice Crl:SHO-Prkdc$^{scid}$Hr$^{hr}$ burdened with PANC1 pancreas cancer treated with fusion protein of the invention of Ex. 11 and comparatively with rhTRAIL114-281 are shown in FIG. 32 as a diagram of changes of the tumor volume and in FIG. 33 which shows tumor growth inhibition (% TGI) as the percentage of control.

The results of experiments presented in the graphs in FIGS. 32 and 33 show that administration of the fusion protein of the invention Ex. 11 caused tumor PANC1 growth inhibition, with TGI 43% relative to the control on 40th day of the experiment. For rhTRAIL114-281 used as the comparative reference, the slight inhibitory effect on tumor cell growth was obtained relative to the control, with TGI at the level of 12.0%. Thus, fusion proteins of the invention exert much stronger effect compared to rhTRAIL114-281 alone.

Multidrug-Resistant Human Uterine Sarcoma Model

On day 0 mice Crl:SHO-Prkdc$^{scid}$Hr$^{hr}$ were grafted subcutaneously (sc) in the right side with 7×10$^6$ of MES-SA/Dx5 cells suspended in 0.1 ml of HBSS:Matrigel 10:1 mixture by means of a syringe with a 0.5×25 mm needle (Bogmark). When tumors reached the size of ~167-190 mm$^3$ (day 19), mice were randomized to obtain the average size of tumors in the group of ~180 mm$^3$ and assigned to treatment groups. The treatment groups were administered with the preparations of fusion proteins of the invention of Ex. 6, Ex. 19 (30 mg/kg) and rhTRAIL114-281 (10 mg/kg) as a comparison against formulation buffer (5 mM NaH$_2$PO$_4$, 95 mM Na$_2$HPO$_4$, 200 mM NaCl, 5 mM glutatione, 0.1 mM ZnCl$_2$, 10% glycerol, 80 mM saccharose, pH 8.0) as a control. The preparations were administered intravenously (i.v.) six times every second day. When a therapeutic group reached the average tumor size of ~1000 mm$^3$, mice were sacrificed by disruption of the spinal cord. The control group received rhTRAIL114-281.

Figure 34:
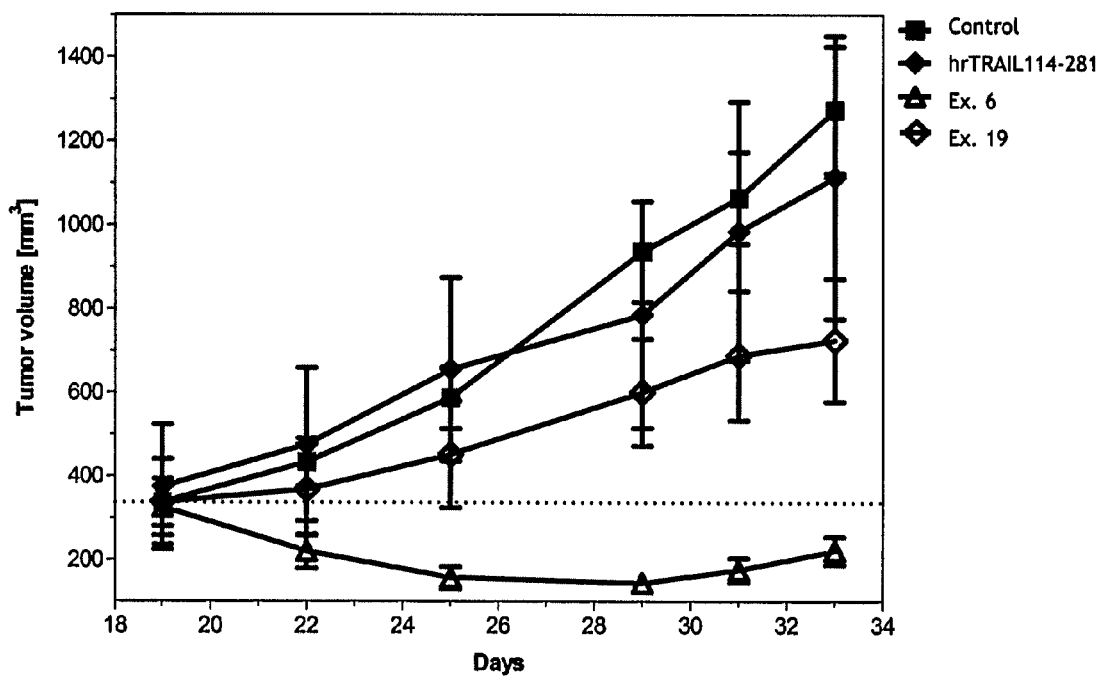
FIG. 34 presents tumor volume changes (% of initial stage) in Crl:SHO-Prkdc$^{scid}$Hr$^{hr}$ mice burdened with multidrug-resistant human uterine sarcoma MES-SA/Dx5 treated with fusion proteins of the invention from Ex. 6 and Ex. 19 compared to rhTRAIL114-281.
Figure 35:
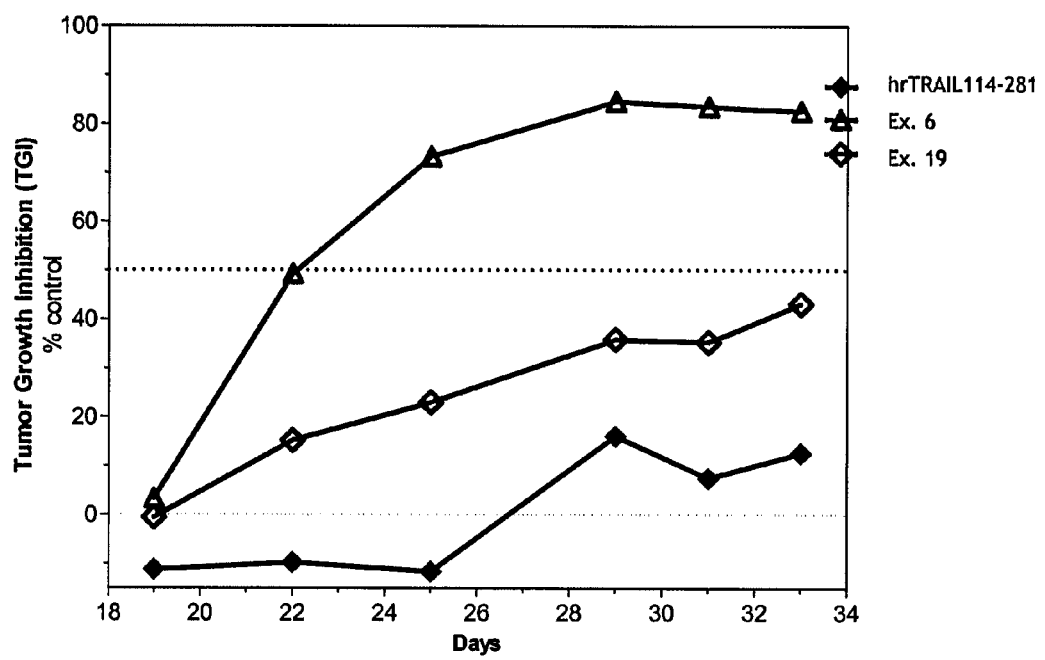
FIG. 35 presents the tumor growth inhibition values (% TGI) in Crl:SHO-Prkdc$^{scid}$Hr$^{hr}$ mice burdened with multidrug-resistant human uterine sarcoma MES-SA/Dx5 treated

The experimental results obtained in mice Crl:SHO-Prkdc$^{scid}$Hr$^{hr}$ burdened with MES-SA/Dx5 uterine sarcoma treated with fusion proteins of the invention of Ex. 18, Ex. 6, Ex. 19 and comparatively with rhTRAIL114-281 are shown in FIG. 34 as a diagram of changes of the tumor volume and in FIG. 35 which shows tumor growth inhibition (% TGI) as the percentage of control. The results of experiments presented in the graphs in FIGS. 34 and 35 show that administration of the fusion proteins of the invention Ex. 6, Ex. 19 caused tumor MES-SA/Dx5 growth inhibition, with TGI respectively 99.7% and 99.7% relative to the control on 33th day of the experiment. For rhTRAIL114-281 used as the comparative reference, the slight inhibitory effect on tumor cell growth was obtained relative to the control, with TGI at the level of 29%. Thus, fusion proteins of the invention exert much stronger effect compared to rhTRAIL114-281 alone.

The tested fusion proteins did not cause significant side effects manifested by a decrease in body weight of mice (i.e. less than 10% of the baseline body weight). This shows low systemic toxicity of the protein.

The invention claimed is:

1. A fusion protein comprising:
   (i) domain (a) comprising a functional fragment of soluble human Tumour Necrosis Factor-Related Apoptosis Inducing Ligand (hTRAIL) protein sequence starting with an amino acid in a position not lower than hTRAIL95 and ending with the amino acid at position hTRAIL281, or a homolog of said functional fragment having at least 70% sequence identity; and
   (ii) domain (b) comprising a sequence of an anti-angiogenic effector peptide, wherein said effector peptide is an inhibitor for growth factor receptor and is selected from the group of growth factor fragments consisting of a Vascular Endothelial Growth Factor (VEGF) fragment having the amino acid sequence set forth as SEQ ID NO: 17, a Platelet-Derived Growth Factor (PDGF) fragment having the amino acid sequence set forth as SEQ ID NO: 22, and an Epidermal Growth Factor (EGF) fragment having the amino acid sequence set forth as SEQ ID NO: 23;
wherein the sequence of domain (b) is attached at C-terminus or N-terminus of domain (a).

2. The fusion protein according to claim 1, wherein domain (a) comprises the functional fragment of soluble hTRAIL protein sequence starting with an amino acid in a range from hTRAIL95 to hTRAIL121, inclusive.

3. The fusion protein according to claim 2, wherein domain (a) is selected from the group consisting of hTRAIL95-281, hTRAIL119-281, hTRAIL120-281 and hTRAIL121-281.

4. The fusion protein according to claim 1, wherein the fusion protein between domain (a) and domain (b) contains domain (c) comprising a protease cleavage site, selected from the group consisting of sequences recognized by metalloprotease MMP, a sequence recognized by urokinase uPA, or a combination thereof.

5. The fusion protein according to claim 4, wherein the sequence recognized by metalloprotease MMP is SEQ ID NO: 24, SEQ ID NO: 55 or SEQ ID NO: 56, and the sequence recognized by urokinase uPA is SEQ ID NO: 25.

6. The fusion protein according to claim 5, wherein the fusion protein between domains (a), (b), or (c) comprises additionally a glycine, glycine-serine or cysteine flexible steric linker or a combination thereof.

7. The fusion protein according to claim 1, having an amino acid sequence selected from the group consisting of SEQ ID NO: 1; SEQ ID NO: 2; SEQ ID NO: 3; SEQ ID NO:4; SEQ ID NO: 5; SEQ ID NO: 6; SEQ ID NO: 9; SEQ ID NO: 10; SEQ ID NO: 11; SEQ ID NO: 14; SEQ ID NO: 15; SEQ ID NO: 46; SEQ ID NO: 47; SEQ ID NO: 48, and SEQ ID NO: 49.

8. A pharmaceutical composition, comprising as an active ingredient the fusion protein as defined in claim 7, in combination with a pharmaceutically acceptable carrier.

9. A pharmaceutical composition, comprising as an active ingredient the fusion protein as defined in claim 1, in combination with a pharmaceutically acceptable carrier.

10. A method of treatment of cancer in a mammal in a need thereof, comprising administering to the mammal an effective amount of the pharmaceutical composition as defined in claim 9.

11. The method of claim 10, wherein the mammal is a human.

12. The fusion protein of claim 1, wherein domain (b) comprises a VEGF fragment having the amino acid sequence set forth as SEQ ID NO: 17.

13. The fusion protein of claim 1, wherein domain (b) comprises a PDGF fragment having the amino acid sequence set forth as SEQ ID NO: 22.

14. The fusion protein of claim 1, wherein domain (b) comprises an EGF fragment having the amino acid sequence set forth as SEQ ID NO: 23.

* * * * *